US010314297B2

(12) United States Patent
Shen

(10) Patent No.: US 10,314,297 B2
(45) Date of Patent: *Jun. 11, 2019

(54) DNA KNOCK-IN SYSTEM

(71) Applicant: Biocytogen Boston Corp, Wakefield, MA (US)

(72) Inventor: Yuelei Shen, Beijing (CN)

(73) Assignee: Biocytogen Boston Corp, Wakefield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/701,385

(22) Filed: Sep. 11, 2017

(65) Prior Publication Data

US 2018/0049412 A1    Feb. 22, 2018

Related U.S. Application Data

(63) Continuation of application No. 15/503,695, filed as application No. PCT/US2015/045134 on Aug. 13, 2015.

(60) Provisional application No. 62/037,551, filed on Aug. 14, 2014.

(51) Int. Cl.
| | | |
|---|---|---|
| *C12N 15/00* | (2006.01) | |
| *C12N 15/85* | (2006.01) | |
| *C12N 15/90* | (2006.01) | |
| *A01K 67/027* | (2006.01) | |
| *C12N 15/10* | (2006.01) | |

(52) U.S. Cl.
CPC ........ *A01K 67/0275* (2013.01); *C12N 15/102* (2013.01); *C12N 15/907* (2013.01); *A01K 2217/072* (2013.01); *A01K 2227/105* (2013.01); *A01K 2267/0393* (2013.01)

(58) Field of Classification Search
CPC .......... A01K 2217/00; A01K 2217/072; A01K 2227/105; C12N 15/00; C12N 15/85; C12N 15/8509; C12N 15/90; C12N 15/902; C12N 15/907
See application file for complete search history.

(56) References Cited

U.S. PATENT DOCUMENTS

| | | | |
|---|---|---|---|
| 6,824,978 B1 | 11/2004 | Cox et al. | |
| 8,546,553 B2 | 10/2013 | Terns et al. | |
| 8,697,359 B1 | 4/2014 | Zhang | |
| 9,522,936 B2* | 12/2016 | Miller ................. | C07K 14/195 |
| 2010/0076057 A1 | 3/2010 | Sontheimer et al. | |
| 2010/0093617 A1 | 4/2010 | Barrangou et al. | |
| 2011/0217739 A1 | 9/2011 | Terns et al. | |
| 2011/0281361 A1* | 11/2011 | DeKelver .......... | C12N 15/8213 |
| | | | 435/463 |
| 2012/0276074 A1* | 11/2012 | Scharenberg .......... | A61K 38/45 |
| | | | 424/94.2 |
| 2013/0011828 A1 | 1/2013 | Barrangou et al. | |
| 2013/0326645 A1 | 12/2013 | Cost et al. | |
| 2013/0330778 A1 | 12/2013 | Zeiner et al. | |
| 2014/0073015 A1 | 3/2014 | Zhao et al. | |
| 2014/0088797 A1 | 3/2014 | Doudna et al. | |
| 2014/0090113 A1 | 3/2014 | Cogen et al. | |
| 2014/0093941 A1 | 4/2014 | Terns et al. | |
| 2014/0179770 A1* | 6/2014 | Zhang .................... | C12N 15/86 |
| | | | 514/44 R |
| 2014/0199767 A1 | 7/2014 | Barrangou et al. | |
| 2016/0053272 A1* | 2/2016 | Wurtzel ................. | C12N 15/66 |
| | | | 435/91.33 |
| 2017/0273284 A1* | 9/2017 | Shen .................... | C12N 15/102 |

FOREIGN PATENT DOCUMENTS

| | | |
|---|---|---|
| CN | 103388006 A | 11/2013 |
| CN | 103725710 A | 4/2014 |
| WO | WO-1994/018313 A1 | 8/1994 |
| WO | WO-1995/09233 A1 | 4/1995 |
| WO | WO-2007/025097 A2 | 3/2007 |
| WO | WO-2010/011961 A2 | 1/2010 |
| WO | WO-2010/075424 A2 | 7/2010 |
| WO | WO-2011/072246 A2 | 6/2011 |
| WO | WO 13/126794 * | 8/2013 |
| WO | WO-2013/126794 A1 | 8/2013 |
| WO | WO-2013/141680 A1 | 9/2013 |
| WO | WO-2013/142578 A1 | 9/2013 |
| WO | WO-2013/163628 A2 | 10/2013 |
| WO | WO-2013/169802 A1 | 11/2013 |
| WO | WO-2013/176772 A1 | 11/2013 |
| WO | WO-2013/181440 A1 | 12/2013 |
| WO | WO-2013/188037 A2 | 12/2013 |
| WO | WO-2013/188522 A2 | 12/2013 |
| WO | WO-2013/188638 A2 | 12/2013 |
| WO | WO-2013/192278 A1 | 12/2013 |
| WO | WO-2014/018423 A2 | 1/2014 |
| WO | WO-2014/022702 A2 | 2/2014 |

(Continued)

OTHER PUBLICATIONS

Meyer et al, PNAS 107(34):15022-15026, 2010.*
Ahrens, C.H. et al. (1997). "The Sequence of the *Orgyia pseudotsugata* Multinucleocapsid Nuclear Polyhedrosis Virus Genome," *Virology* 229(2):381-399.
Ayres, M.D. et al. (Aug. 1, 1994). "The Complete DNA Sequence of *Autographa califomica* Nuclear Polyhedrosis Virus," *Virology* 202:586-605.
Boyer, L.A. et al. (Sep. 23, 2005). "Core Transcriptional Regulatory Circuitry in Human Embryonic Stem Cells," *Cell* 122(6):947-956.
Choo, Y.et al. (Nov. 1994). "Toward a Code for the Interactions of Zinc Fingers with DNA: Selection of Randomized Fingers Displayed on Phage," *Proc. Natl. Acad. Sci. USA* 91:11163-11167.

(Continued)

*Primary Examiner* — Kevin K Hill
(74) *Attorney, Agent, or Firm* — Morrison & Foerster LLP

(57) ABSTRACT

The present disclosure relates to an efficient genome editing technique. In one aspect, the technique can greatly improve the efficiency of homologous recombination during intracellular targeting, including gene targeting. Using this technique, genetically modified cell lines, rat, mouse, zebrafish, and fertilized eggs of other species can be quickly and efficiently generated.

20 Claims, 24 Drawing Sheets
Specification includes a Sequence Listing.

(56) References Cited

FOREIGN PATENT DOCUMENTS

| WO | WO-2014/039872 A1 | 3/2014 |
| WO | WO-2014/065596 A1 | 5/2014 |
| WO | WO-2016/025759 A1 | 2/2016 |

OTHER PUBLICATIONS

Cong, L. et al. (Feb. 15, 2013). "Multiplex Genome Engineering Using CRISPR/Cas Systems," *Science* 339(6121):819-823.
Curiel, D.T. et al. (1992). "High-Efficiency Gene Transfer Mediated by Adenovirus Coupled to DNA-Polylysine Complexes," *Hum. Gene Ther.* 3:147-154.
Goldstein, J.N. et al. (1998). "The Exonuclease Activity of HSV-1 UL12 is Required for in Vivo Function," *Virology*, 244:442-457.
Groenen, P.M.A. et al. (1993). "Nature of DNA Polymorphism in the Direct Repeat Cluster of *Mycobacterium tuberculosis*; Application for Strain Differentiation by a Novel Typing Method," *Mol. Microbiol.* 10(5):1057-1065.
Hanin, M. et al. (2001). "Gene Targeting in *Arabidopsis*," *The Plant J.* 28(6):671-677.
Hockemeyer, D. et al. (Feb. 1, 2012). "Genetic Engineering of Human ES and iPS Cells Using TALE Nucleases," *Nat. Biotechnol.* 29(8):731-734.
Hoe, N. et al. (Mar.-Apr. 1999). "Rapid Molecular Genetic Subtyping of Serotype M1 Group A *Streptococcus* Strains," *Emerg. Infect. Dis.* 5(2):254-263.
Iacovitti, L. et al. (Dec. 2, 2014). "The hTH-GFP Reporter Rat Model for the Study of Parkinson's Disease," *PLoS One* 9(12):e113151, 19 pages.
International Preliminary Report on Patentabiltiy for PCT/US2015/45134, dated Feb. 14, 2017, filed Aug. 13, 2015, 8 Pages.
International Search Report for PCT/US2015/45134, dated Nov. 27, 2015, filed Aug. 13, 2015, 4 Pages.
Irion, U. et al. (2014, e-pub. Nov. 19, 2014). "Precise and Efficient Genome Editing in Zebrafish Using the CRISPR/Cas9 System," *Development* 141:1-4, 6 pages.
Ishino, Y. et al. (Dec. 1987). "Nucleotide Sequence of the iap Gene, Responsible for Alkaline Phosphatase Isozyme Conversion in *Escherichia coli*, and Identification of the Gene Product," *J. Bacteriol.* 169(12):5429-5433.
Jamieson, A.C. et al. (Apr. 15, 1994). "In Vitro Selection of Zinc Fingers with Altered DNA-Binding Specificity," *Biochemistry* 33(19):5689-5695.
Jansen, R. et al. (2002). "Identification of a Novel Family of Sequence Repeats Among Prokaryotes," *OMICS J. Integ. Biol.* 6(1):23-33.
Jansen, R. et al. (2002). "Identification of Genes that are Associated with DNA Repeats in Prokaryotes," *Mol. Microbiol.* 43(6):1565-1575.
Jasin, M. (Jun. 1996). "Genetic Manipulation of Genomes with Rare-Cutting Endonucleases," *Trends in Genetics:TIG* 12(6):224-228.
Jinek, M. et al. (Aug. 17, 2012). "A Programmable Dual-RNA-Guided DNA Endonuclease in Adaptive Bacterial Immunity," *Science* 337:816-821.
Kovall, R. et al. (Sep. 19, 1997). "Toroidal Structure of λ-Exonuclease," *Science* 277(5333):1824-1827.

Mali, P. et al. (Feb. 15, 2013). "RNA-Guided Human Genome Engineering via Cas9," *Science* 339(6121):823-826.
Martinez, R. et al. (1996). "The Product of a 1.9-kb mRNA Which Overlaps the HSV-1 Alkaline Nuclease Gene (UL12) Cannot Relieve the Growth Defects of a Null Mutant," *Virology*, 215:152-164.
Masepohl, B. et al. (1996). "Long Tandemly Repeated Repetitive (LTRR) Sequences in the Filamentous Cyanobacterium *Anabaena* sp. PCC 7120," *Biochim. Biophys. Acta* 1307:26-30.
Mojica, F.J.M. et al. (1995). "Long Stretches of Short Tandem Repeats are Present in the Largest Replicons of the Archaea *Haloterax mediterranei* and *Haloferax volcanil* and Could be Involved in Replicon Partitioning," *Mol. Microbiol.* 17(1):85-93.
Mojica, F.J.M. et al. (2000). "MicroCorrespondence-Biological Significance of a Family of Regularly Spaced Repeats in the Genomes of Archaea, Bacteria and Mitochondria," *Mol. Microbiol.* 36(1):244-246.
Nakata, A. et al. (Jun. 1989). "Unusual Nucleotide Arrangement with Repeated Sequences in the *Escherichia coli* K-12 Chromosome," *J. Bacteriol* 171(6):3553-3556.
Rebar, E.J. et al. (Feb. 4, 1994). "Zinc Finger Phage: Affinity Selection of Fingers with New DNA-Binding Specificities," *Science* 263:671-673.
Sander, J.D. et al. (Apr. 2014). "CRISPR-Cas Systems for Genome Editing, Regulation and Targeting," *Nature Biotechnology* 32(4):347-355.
Van Embden, J.D.A. et al. (May 2000). "Genetic Variation and Evolutionary Origin of the Direct Repeat Locus of *Mycobacterium tuberculosis* Complex Bacteria," *J. Bacteriol.* 182(9):2393-2401.
Wiedenheft, B. et al. (Feb. 16, 2012). "RNA-Guided Genetic Silencing Systems in Bacteria and Archaea," *Nature* 482:331-338.
Williams, R.S. et al. (Apr. 1991). "Introduction of Foreign Genes Into Tissues of Living Mice by DNA-Coated Microprojectiles," *Proc. Natl. Acad. Sci. USA* 88:2726-2730.
Wilson, J.M. et al. (Jan. 15, 1992). "Hepatocyte-directed Gene Transfer in Vivo Leads to Transient Improvement of Hypercholesterolemia in Low Density Lipoprotein Receptor-Deficient Rabbits," *J. Biol. Chem.* 267(2):963-967.
Written Opinion of the International Searching Authority for PCT/US2015/45134, dated Nov. 27, 2015, filed Aug. 13, 2015, 7 Pages.
Wu, G.Y. et al. (Apr. 5, 1987). "Receptor-Mediated in Vitro Gene Transformation by a Soluble DNA Carrier System," *J. Biol. Chem.* 262(10):4429-4432.
Wu, G.Y. and Wu, C.H. (Oct. 15, 1988). "Receptor-Mediated Gene Delivery and Expression in Vivo," *J. Biol. Chem.* 263(29):14621-14624.
Wu, Y. et al. (Dec. 5, 2013) "Correction of a Genetic Disease in Mouse via Use of CRISPR-Cas9," *Cell Stem Cell* 13:659-662.
Yang, H. et al. (Sep. 12, 2013). "One-Step Generation of Mice Carrying Reporter and Conditional Alleles by CRISPR/CAS Mediated Genome Engineering," *Cell* 154(6):1370-1379.
Yu, J. et al. (Dec. 21, 2007) "Induced Pluripotent Stem Cell Lines Derived from Human Somatic Cells," *Science* 318:1917-1920.
Cristea, S. et al. (2013, e-pub. Oct. 5, 2012). "In vivo Cleavage of Transgene Donors Promotes Nuclease-Mediated Targeted Integration," *Biotechnol. & Bioeng.* 110(3):871-880.
Gaj, T. et al. (Jul. 2013, e-pub. May 9, 2013). "ZFN, Talen, and CRISPR/Cas-Based Methods for Genome Engineering," *Trends Biotechnol.* 31(7):397-405.

\* cited by examiner

FIG. 2
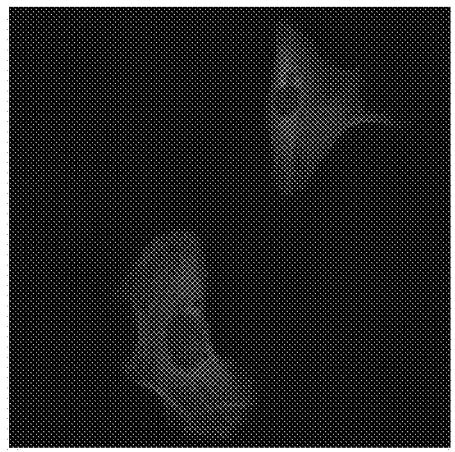
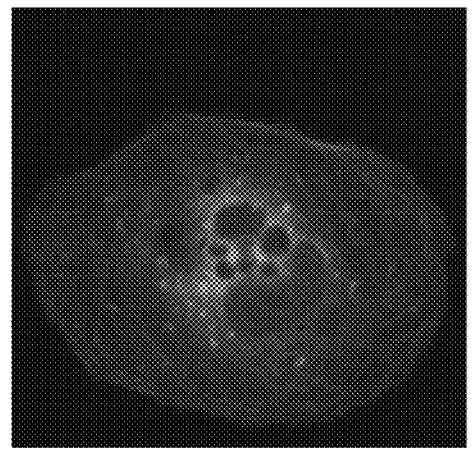

FIG. 5
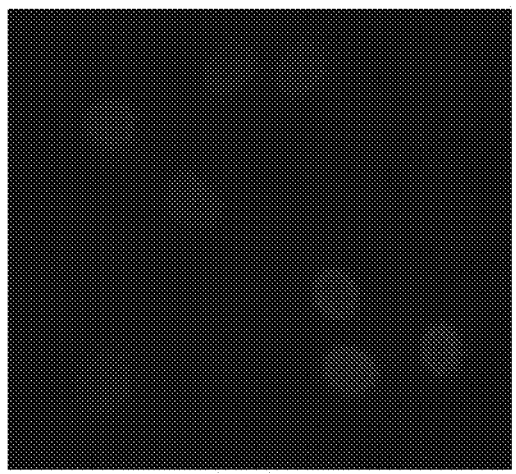 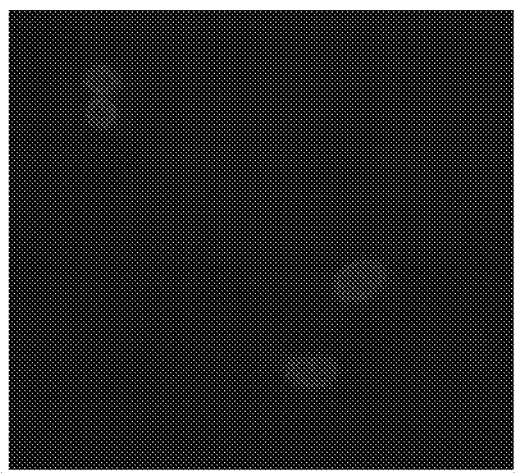

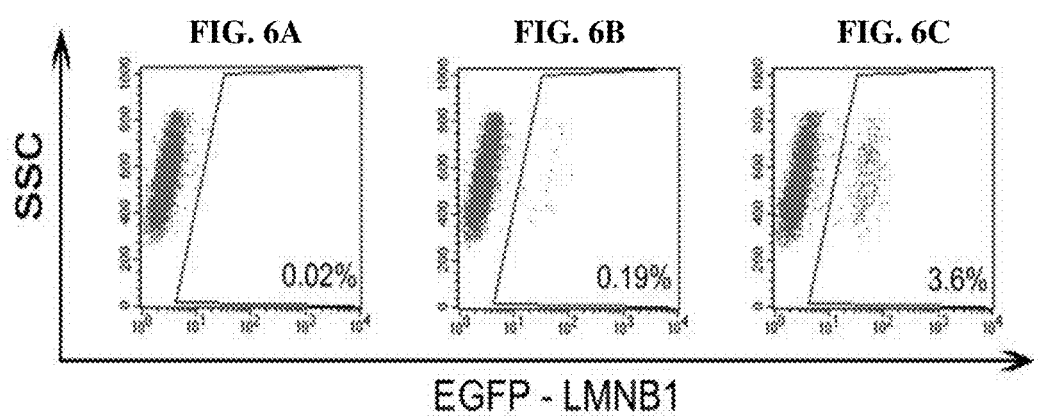

FIG. 7A ACTB allele
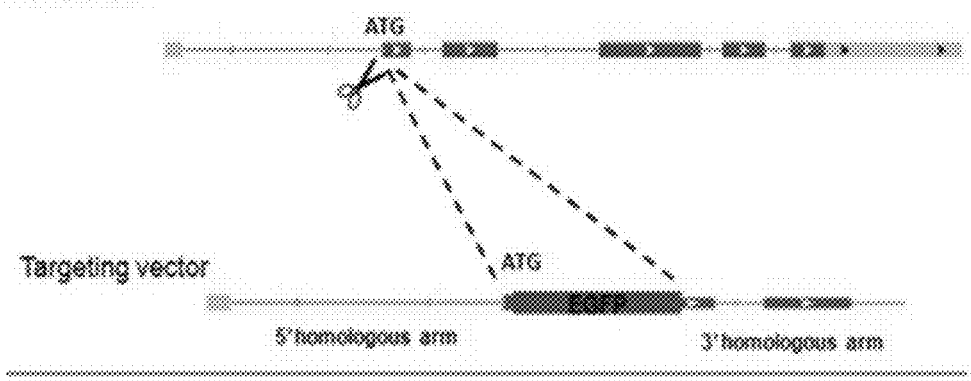
FIG. 7B LMNB1 allele
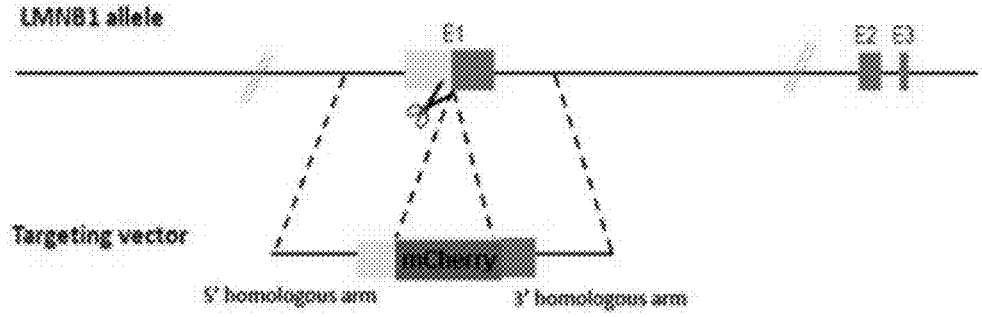

southern blot strategy

|        | Probe  | WT      | Targeted |
|--------|--------|---------|----------|
| EcoRV  | 5'-p   | 15.8 kb | 9.2 kb   |
| EcoRV  | 3'-p   | 15.8 kb | 7.3 kb   |
| EcoRV  | dsRed  | -       | 9.2 kb   |

FIG. 16A  5'-junction PCR (TH-5'-F / TH-5'-R)
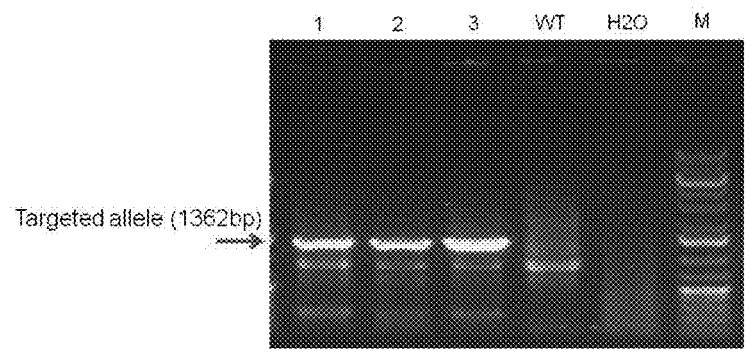
FIG. 16B  3'-junction PCR (TH-3'-F / TH-3'-R)
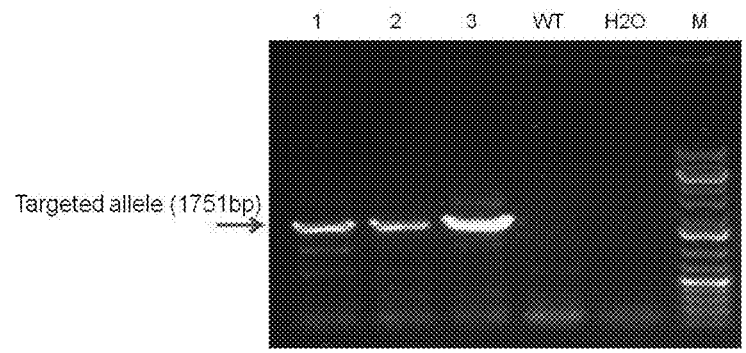

FIG. 22A          5'-junction PCR (OCT4-5'-F / OCT4-5'-R)
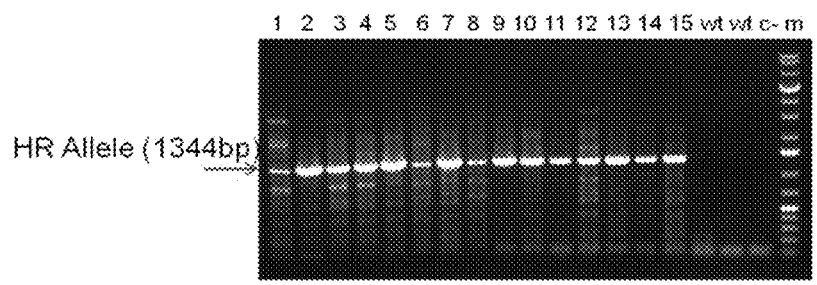
FIG. 22B          3'-junction PCR (OCT4-3'-F / OCT4-3'-R)
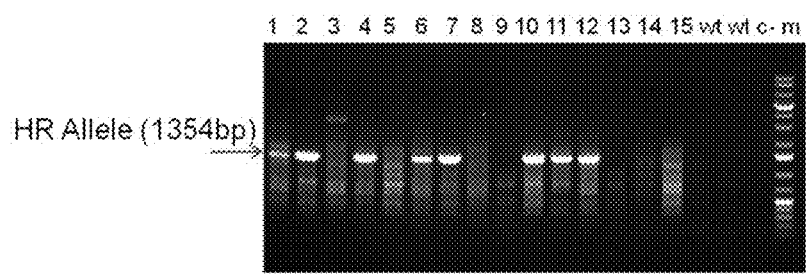
FIG. 22C          Full length PCR (OCT4-5'-F / OCT4-3'-R)
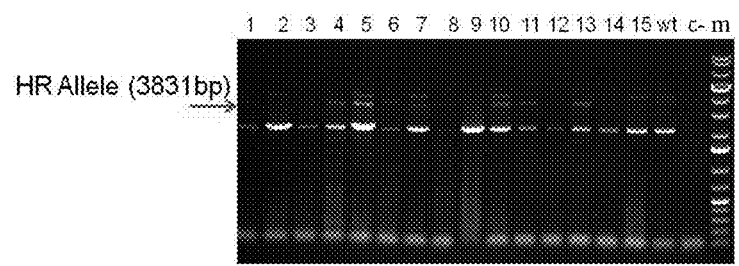

SEQUENCE LISTING

<160> NUMBER OF SEQ ID NOS: 45

<210> SEQ ID NO 1
<211> LENGTH: 2247
<212> TYPE: DNA
<213> ORGANISM: Human herpesvirus 1

<400> SEQUENCE: 1

```
tactgtcgtc ggtggcgctg cctcccgagc ttaagcctct cctggtgctg gtgtcccgcc        60
tgtgtcacac caacccgtgc gcgcggcacg cgctgtcgtg agaatcagcg ttcacccggc       120
ggcgcgctca accaccgctc ccccacgtc gtctcggaaa tggagtccac ggtaggccca       180
gcatgtccgc cgggacgcac cgtgactaag cgtccctggg ccctggccga ggacacccct       240
cgtggccccg acagccccc caagcgcccc cgccctaaca gtcttccgct gacaaccacc       300
ttccgtcccc tgccccccc accccagacg acatcagctg tggacccgag ctcccattcg       360
cccgttaacc ccccacgtga tcagcacgcc accgacaccg cagacgaaaa gccccgggcc       420
gcgtcgccgg cactttctga cgcctcaggg cctccgaccc cagacattcc gctatctcct       480
gggggcaccc acgcccgcga cccggacgcc gatcccgact ccccggacct tgactctatg       540
tggtcggcgt cggtgatccc caacgcgctg ccctcccata tactagccga gacgttcgag       600
cgccacctgc gcgggttgct gcgcggccgtc gcgcccctc tggccatcgg tccctctgg        660
gcccgcctgg attatctgtg ttccctggcc gtggtcctcg aggaggcggg tatggtggac       720
cgcggactcg tcggcacct atggcgcctg acgcgccgcg ggcccccggc cgccgcggac       780
gccgtggcgc ccggcccct catggggttt tacgaggcgg ccacgcaaaa ccaggccgac       840
tgccagctat gggccctgct ccggcggggc ctcacgaccg catccaccct ccgctggggc       900
ccccagggtc cgtgtttctc gccccagtgg ctgaagcaca acgccagcct gcggccggat       960
gtacagtctt cggcggtgat gttcgggcgg gtgaacgagc cgacgcccg aagcctgctg      1020
tttcgctact gcgtgggccg cgcggacgac ggcggcgagg ccggcgccga cacgcggcgc      1080
tttatcttcc acgaacccag cgacctcgcc gaagagaacg tgcatacgtg tggggtcctc      1140
atggacggtc acacggggat ggtcggggcg tccctggata ttctcgtctg tcctcgggac      1200
attcacggct acctggcccc agtccccaag accccctgg ccttttacga ggtcaaatgc      1260
cgggccaagt acgctttcga ccccatggac cccagcgacc ccacggcctc cgcgtacgag      1320
gacttgatgg cacaccggtc cccggaggcg ttccgggcat ttatccggtc gatcccgaag      1380
cccagcgtgc gatacttcgc gcccgggcgc gtccccggcc cggaggaggc tctcgtcacg      1440
caagaccagg cctggtcaga ggcccacgcc tcgggcgaaa aaaggcggtg ctccgccgcg      1500
gatcgggcct tggtggagtt aaatagcggc gttgtctcgg aggtgcttct gtttggcgcc      1560
cccgacctcg gacgccacac catctcccc gtgtcctgga ctccgggga tctggtccgc      1620
cgcgagcccg tcttcgcgaa ccccgtcac ccgaacttta agcagatctt ggtgcagggc      1680
tacgtgctcg acagccactt ccccgactgc ccccccacc cgcatctggt gacgtttatc      1740
ggcaggcacc gcaccagcgc ggaggagggc gtaacgttcc gcctggagga cggcgccggg      1800
gctctcgggg ccgcaggacc cagcaaggcg tccattctcc cgaaccaggc cgttccgatc      1860
gccctgatca ttaccccgt ccgcatcgat ccggagatct ataaggccat ccagcgaagc      1920
agccgcctg cattcgacga cacgctcgcc gagctatggg cctctcgttc tccggggccc      1980
ggccctgctg ctgccgaaac aacgtcctca tcaccgacga cggggaggtc gtctcgctga      2040
ccgcccacga ctttgacgtc gtggatatcg agtccgaaga ggaaggtaat ttctacgtgc      2100
```

```
cccggatat gcgcggggtt acgcgggccc cggggagaca gcgcctgcgt tcatcggacc   2160 cccctcgcg ccacactcac cggcggaccc ccggaggcgc ctgccccgcc acccagtttc   2220 cacccccat gtccgatagc gaataaa                                       2247
```

<210> SEQ ID NO 2
<211> LENGTH: 626
<212> TYPE: PRT
<213> ORGANISM: Human herpesvirus 1

<400> SEQUENCE: 2

```
Met Glu Ser Thr Val Gly Pro Ala Cys Pro Pro Gly Arg Thr Val Thr
1               5                   10                  15

Lys Arg Pro Trp Ala Leu Ala Glu Asp Thr Pro Arg Gly Pro Asp Ser
            20                  25                  30

Pro Pro Lys Arg Pro Arg Pro Asn Ser Leu Pro Leu Thr Thr Thr Phe
        35                  40                  45

Arg Pro Leu Pro Pro Pro Gln Thr Thr Ser Ala Val Asp Pro Ser
    50                  55                  60

Ser His Ser Pro Val Asn Pro Pro Arg Asp Gln His Ala Thr Asp Thr
65                  70                  75                  80

Ala Asp Glu Lys Pro Arg Ala Ala Ser Pro Ala Leu Ser Asp Ala Ser
                85                  90                  95

Gly Pro Pro Thr Pro Asp Ile Pro Leu Ser Pro Gly Gly Thr His Ala
            100                 105                 110

Arg Asp Pro Asp Ala Asp Pro Asp Ser Pro Asp Leu Asp Ser Met Trp
        115                 120                 125

Ser Ala Ser Val Ile Pro Asn Ala Leu Pro Ser His Ile Leu Ala Glu
    130                 135                 140

Thr Phe Glu Arg His Leu Arg Gly Leu Leu Arg Gly Val Arg Ala Pro
145                 150                 155                 160

Leu Ala Ile Gly Pro Leu Trp Ala Arg Leu Asp Tyr Leu Cys Ser Leu
                165                 170                 175

Ala Val Val Leu Glu Glu Ala Gly Met Val Asp Arg Gly Leu Gly Arg
            180                 185                 190

His Leu Trp Arg Leu Thr Arg Arg Gly Pro Pro Ala Ala Ala Asp Ala
        195                 200                 205

Val Ala Pro Arg Pro Leu Met Gly Phe Tyr Glu Ala Ala Thr Gln Asn
    210                 215                 220

Gln Ala Asp Cys Gln Leu Trp Ala Leu Leu Arg Arg Gly Leu Thr Thr
225                 230                 235                 240

Ala Ser Thr Leu Arg Trp Gly Pro Gln Gly Pro Cys Phe Ser Pro Gln
                245                 250                 255

Trp Leu Lys His Asn Ala Ser Leu Arg Pro Asp Val Gln Ser Ser Ala
            260                 265                 270

Val Met Phe Gly Arg Val Asn Glu Pro Thr Ala Arg Ser Leu Leu Phe
        275                 280                 285

Arg Tyr Cys Val Gly Arg Ala Asp Asp Gly Gly Glu Ala Gly Ala Asp
    290                 295                 300

Thr Arg Arg Phe Ile Phe His Glu Pro Ser Asp Leu Ala Glu Glu Asn
305                 310                 315                 320

Val His Thr Cys Gly Val Leu Met Asp Gly His Thr Gly Met Val Gly
                325                 330                 335

Ala Ser Leu Asp Ile Leu Val Cys Pro Arg Asp Ile His Gly Tyr Leu
```

```
                    340                 345                 350
Ala Pro Val Pro Lys Thr Pro Leu Ala Phe Tyr Glu Val Lys Cys Arg
                355                 360                 365
Ala Lys Tyr Ala Phe Asp Pro Met Asp Pro Ser Asp Pro Thr Ala Ser
            370                 375                 380
Ala Tyr Glu Asp Leu Met Ala His Arg Ser Pro Glu Ala Phe Arg Ala
385                 390                 395                 400
Phe Ile Arg Ser Ile Pro Lys Pro Ser Val Arg Tyr Phe Ala Pro Gly
                405                 410                 415
Arg Val Pro Gly Pro Glu Glu Ala Leu Val Thr Gln Asp Gln Ala Trp
            420                 425                 430
Ser Glu Ala His Ala Ser Gly Glu Lys Arg Arg Cys Ser Ala Ala Asp
                435                 440                 445
Arg Ala Leu Val Glu Leu Asn Ser Gly Val Val Ser Glu Val Leu Leu
            450                 455                 460
Phe Gly Ala Pro Asp Leu Gly Arg His Thr Ile Ser Pro Val Ser Trp
465                 470                 475                 480
Ser Ser Gly Asp Leu Val Arg Arg Glu Pro Val Phe Ala Asn Pro Arg
                485                 490                 495
His Pro Asn Phe Lys Gln Ile Leu Val Gln Gly Tyr Val Leu Asp Ser
                500                 505                 510
His Phe Pro Asp Cys Pro Pro His Pro His Leu Val Thr Phe Ile Gly
            515                 520                 525
Arg His Arg Thr Ser Ala Glu Glu Gly Val Thr Phe Arg Leu Glu Asp
            530                 535                 540
Gly Ala Gly Ala Leu Gly Ala Ala Gly Pro Ser Lys Ala Ser Ile Leu
545                 550                 555                 560
Pro Asn Gln Ala Val Pro Ile Ala Leu Ile Ile Thr Pro Val Arg Ile
                565                 570                 575
Asp Pro Glu Ile Tyr Lys Ala Ile Gln Arg Ser Ser Arg Leu Ala Phe
            580                 585                 590
Asp Asp Thr Leu Ala Glu Leu Trp Ala Ser Arg Ser Pro Gly Pro Gly
                595                 600                 605
Pro Ala Ala Ala Glu Thr Thr Ser Ser Ser Pro Thr Thr Gly Arg Ser
            610                 615                 620
Ser Arg
625

<210> SEQ ID NO 3
<211> LENGTH: 23
<212> TYPE: DNA
<213> ORGANISM: Artificial Sequence
<220> FEATURE:
<223> OTHER INFORMATION: Synthetic Construct

<400> SEQUENCE: 3
ggcagaaatg gctccgatcg agg                                           23

<210> SEQ ID NO 4
<211> LENGTH: 23
<212> TYPE: DNA
<213> ORGANISM: Artificial Sequence
<220> FEATURE:
<223> OTHER INFORMATION: Synthetic Construct

<400> SEQUENCE: 4
gggcgggatt gatagcgcgc ggg                                           23
```

<210> SEQ ID NO 5
<211> LENGTH: 23
<212> TYPE: DNA
<213> ORGANISM: Artificial Sequence
<220> FEATURE:
<223> OTHER INFORMATION: Synthetic Construct

<400> SEQUENCE: 5
ggcagtcggg aacatctcgt ggg                                                23

<210> SEQ ID NO 6
<211> LENGTH: 23
<212> TYPE: DNA
<213> ORGANISM: Artificial Sequence
<220> FEATURE:
<223> OTHER INFORMATION: Synthetic Construct

<400> SEQUENCE: 6
gggcgcagta attcttagag cgg                                                23

<210> SEQ ID NO 7
<211> LENGTH: 23
<212> TYPE: DNA
<213> ORGANISM: Artificial Sequence
<220> FEATURE:
<223> OTHER INFORMATION: Synthetic Construct

<400> SEQUENCE: 7
ggctaataac ttaatcgtgg agg                                                23

<210> SEQ ID NO 8
<211> LENGTH: 23
<212> TYPE: DNA
<213> ORGANISM: Artificial Sequence
<220> FEATURE:
<223> OTHER INFORMATION: Synthetic Construct

<400> SEQUENCE: 8
ggttaagcct tattggtggt cgg                                                23

<210> SEQ ID NO 9
<211> LENGTH: 23
<212> TYPE: DNA
<213> ORGANISM: Artificial Sequence
<220> FEATURE:
<223> OTHER INFORMATION: Synthetic Construct

<400> SEQUENCE: 9
ggaggcctgc ttgcaagcat tgg                                                23

<210> SEQ ID NO 10
<211> LENGTH: 23
<212> TYPE: DNA
<213> ORGANISM: Artificial Sequence
<220> FEATURE:
<223> OTHER INFORMATION: Synthetic Construct

<400> SEQUENCE: 10
ggttaggccc taagcgaata cgg                                                23

<210> SEQ ID NO 11
<211> LENGTH: 23
<212> TYPE: DNA
<213> ORGANISM: Artificial Sequence
<220> FEATURE:

<223> OTHER INFORMATION: Synthetic Construct

<400> SEQUENCE: 11
ggagccgagt tgacggttag cgg                                              23

<210> SEQ ID NO 12
<211> LENGTH: 23
<212> TYPE: DNA
<213> ORGANISM: Artificial Sequence
<220> FEATURE:
<223> OTHER INFORMATION: Synthetic Construct

<400> SEQUENCE: 12
ggggttcctt cacgagcgtc cgg                                              23

<210> SEQ ID NO 13
<211> LENGTH: 23
<212> TYPE: DNA
<213> ORGANISM: Artificial Sequence
<220> FEATURE:
<223> OTHER INFORMATION: Synthetic Construct

<400> SEQUENCE: 13
ggtacaatgt aacgttgcgc ggg                                              23

<210> SEQ ID NO 14
<211> LENGTH: 23
<212> TYPE: DNA
<213> ORGANISM: Artificial Sequence
<220> FEATURE:
<223> OTHER INFORMATION: Synthetic Construct

<400> SEQUENCE: 14
ggtattcaag tcactaatgt cgg                                              23

<210> SEQ ID NO 15
<211> LENGTH: 23
<212> TYPE: DNA
<213> ORGANISM: Artificial Sequence
<220> FEATURE:
<223> OTHER INFORMATION: Synthetic Construct

<400> SEQUENCE: 15
ggaacccctt ccgttccgtc ggg                                              23

<210> SEQ ID NO 16
<211> LENGTH: 23
<212> TYPE: DNA
<213> ORGANISM: Artificial Sequence
<220> FEATURE:
<223> OTHER INFORMATION: Synthetic Construct

<400> SEQUENCE: 16
ggtattcact cctaaagcgt cgg                                              23

<210> SEQ ID NO 17
<211> LENGTH: 23
<212> TYPE: DNA
<213> ORGANISM: Artificial Sequence
<220> FEATURE:
<223> OTHER INFORMATION: Synthetic Construct

<400> SEQUENCE: 17
gggatggaac actagactgc ggg                                              23

```
<210> SEQ ID NO 18
<211> LENGTH: 23
<212> TYPE: DNA
<213> ORGANISM: Artificial Sequence
<220> FEATURE:
<223> OTHER INFORMATION: Synthetic Construct

<400> SEQUENCE: 18
ggttaatccc tcatgaccgt cgg                                               23

<210> SEQ ID NO 19
<211> LENGTH: 23
<212> TYPE: DNA
<213> ORGANISM: Artificial Sequence
<220> FEATURE:
<223> OTHER INFORMATION: Synthetic Construct

<400> SEQUENCE: 19
ggagcttcag tgtcggtcgt tgg                                               23

<210> SEQ ID NO 20
<211> LENGTH: 23
<212> TYPE: DNA
<213> ORGANISM: Artificial Sequence
<220> FEATURE:
<223> OTHER INFORMATION: Synthetic Construct

<400> SEQUENCE: 20
ggttacgtgc catatacgtt cgg                                               23

<210> SEQ ID NO 21
<211> LENGTH: 23
<212> TYPE: DNA
<213> ORGANISM: Artificial Sequence
<220> FEATURE:
<223> OTHER INFORMATION: Synthetic Construct

<400> SEQUENCE: 21
cgcggcgata tcatcatcca tgg                                               23

<210> SEQ ID NO 22
<211> LENGTH: 4272
<212> TYPE: DNA
<213> ORGANISM: Artificial Sequence
<220> FEATURE:
<223> OTHER INFORMATION: Synthetic Construct

<400> SEQUENCE: 22
atggactata aggaccacga cggagactac aaggatcatg atattgatta caaagacgat      60
gacgataaga tggccccaaa gaagaagcgg aaggtcggta tccacggagt cccagcagcc     120
gacaagaagt acagcatcgg cctggacatc ggcaccaact ctgtgggctg ggccgtgatc     180
accgacgagt acaaggtgcc cagcaagaaa ttcaaggtgc tgggcaacac cgaccggcac     240
agcatcaaga gaacctgat cggagccctg ctgttcgaca cggcgaaac agccgaggcc      300 acccggctga agagaaccgc cagaagaaga tacaccagac ggaagaaccg gatctgctat     360
ctgcaagaga tcttcagcaa cgagatggcc aaggtggacg acagcttctt ccacagactg     420
gaagagtcct tcctggtgga agaggataag aagcacgagc ggcaccccat cttcggcaac     480
atcgtggacg aggtggccta ccacgagaag taccccacca tctaccacct gagaaagaaa     540
ctggtggaca gcaccgacaa ggccgacctg cggctgatct atctggccct ggcccacatg     600
atcaagttcc ggggccactt cctgatcgag ggcgacctga accccgacaa cagcgacgtg     660
```

```
gacaagctgt tcatccagct ggtgcagacc tacaaccagc tgttcgagga aaaccccatc    720
aacgccagcg gcgtggacgc caaggccatc ctgtctgcca gactgagcaa gagcagacgg    780
ctggaaaatc tgatcgccca gctgcccggc gagaagaaga atggcctgtt cggaaacctg    840
attgccctga gcctgggcct gacccccaac ttcaagagca acttcgacct ggccgaggat    900
gccaaactgc agctgagcaa ggacacctac gacgacgacc tggacaacct gctggcccag    960
atcggcgacc agtacgccga cctgtttctg gccgccaaga acctgtccga cgccatcctg   1020
ctgagcgaca tcctgagagt gaacaccgag atcaccaagg ccccctgag cgcctctatg   1080 atcaagagat acgacgagca ccaccaggac ctgaccctgc tgaaagctct cgtgcggcag   1140
cagctgcctg agaagtacaa agagattttc ttcgaccaga gcaagaacgg ctacgccggc   1200
tacattgacg gcgagccag ccaggaagag ttctacaagt tcatcaagcc catcctggaa   1260
aagatggacg gcaccgagga actgctcgtg aagctgaaca gagaggacct gctgcggaag   1320
cagcggacct tcgacaacgg cagcatcccc caccagatcc acctgggaga gctgcacgcc   1380
attctgcggc ggcaggaaga tttttaccca ttcctgaagg acaaccggga aaagatcgag   1440
aagatcctga ccttccgcat cccctactac gtgggccctc tggccagggg aaacagcaga   1500
ttcgcctgga tgaccagaaa gagcgaggaa accatcaccc cctggaactt cgaggaagtg   1560
gtggacaagg gcgcttccgc ccagagcttc atcgagcgga tgaccaactt cgataagaac   1620
ctgcccaacg agaaggtgct gcccaagcac agcctgctgt acgagtactt caccgtgtat   1680
aacgagctga ccaaagtgaa atacgtgacc gagggaatga gaaagcccgc cttcctgagc   1740
ggcgagcaga aaaaggccat cgtggacctg ctgttcaaga ccaaccggaa agtgaccgtg   1800
aagcagctga aagaggacta cttcaagaaa atcgagtgct tcgactccgt ggaaatctcc   1860
ggcgtggaag atcggttcaa cgcctccctg ggcacatacc acgatctgct gaaaattatc   1920
aaggacaagg acttcctgga caatgaggaa aacgaggaca ttctggaaga tatcgtgctg   1980
accctgacac tgtttgagga cagagagatg atcgaggaac ggctgaaaac ctatgcccac   2040
ctgttcgacg acaaagtgat gaagcagctg aagcggcgga gatacaccgg ctggggcagg   2100
ctgagccgga agctgatcaa cggcatccgg gacaagcagt ccggcaagac aatcctggat   2160
ttcctgaagt ccgacggctt cgccaacaga aacttcatgc agctgatcca cgacgacagc   2220
ctgaccttta aagaggacat ccagaaagcc caggtgtccg gccagggcga tagcctgcac   2280
gagcacattg ccaatctggc cggcagcccc gccattaaga agggcatcct gcagacagtg   2340
aaggtggtgg acgagctcgt gaaagtgatg ggccggcaca gcccgagaa catcgtgatc   2400 gaaatggcca gagagaacca gaccacccag aagggacaga agaacagccg cgagagaatg   2460
aagcggatcg aagagggcat caaagagctg ggcagccaga tcctgaaaga acaccccgtg   2520
gaaaacaccc agctgcagaa cgagaagctg tacctgtact acctgcagaa tgggcgggat   2580
atgtacgtgg accaggaact ggacatcaac cggctgtccg actacgatgt ggaccatatc   2640
gtgcctcaga gctttctgaa ggacgactcc atcgacaaca aggtgctgac cagaagcgac   2700
aagaaccggg gcaagagcga caacgtgccc tccgaagagg tcgtgaagaa gatgaagaac   2760
tactggcggc agctgctgaa cgccaagctg attacccaga gaaagttcga caatctgacc   2820
aaggccgaga aggcggcct gagcgaactg gataaggccg gcttcatcaa gagacagctg   2880
gtggaaaccc ggcagatcac aaagcacgtg gcacagatcc tggactcccg gatgaacact   2940
aagtacgacg agaatgacaa gctgatccgg gaagtgaaag tgatcaccct gaagtccaag   3000
ctggtgtccg atttccggaa ggatttccag ttttacaaag tgcgcgagat caacaactac   3060
```

| | | |
|---|---|---|
| caccacgccc acgacgccta cctgaacgcc gtcgtgggaa ccgccctgat caaaaagtac | 3120 | |
| cctaagctgg aaagcgagtt cgtgtacggc gactacaagg tgtacgacgt gcggaagatg | 3180 | |
| atcgccaaga gcgagcagga atcggcaag gctaccgcca agtacttctt ctacagcaac | 3240 | |
| atcatgaact ttttcaagac cgagattacc ctggccaacg gcgagatccg gaagcggcct | 3300 | |
| ctgatcgaga caaacggcga accggggag atcgtgtggg ataagggccg ggattttgcc | 3360 | |
| accgtgcgga aagtgctgag catgccccaa gtgaatatcg tgaaaaagac cgaggtgcag | 3420 | |
| acaggcggct tcagcaaaga gtctatcctg cccaagagga cagcgataa gctgatcgcc | 3480 | |
| agaaagaagg actgggaccc taagaagtac ggcggcttcg acagcccac cgtggcctat | 3540 | |
| tctgtgctgg tggtggccaa agtggaaaag ggcaagtcca agaaactgaa gagtgtgaaa | 3600 | |
| gagctgctgg ggatcaccat catggaaaga agcagcttcg agaagaatcc catcgacttt | 3660 | |
| ctggaagcca agggctacaa agaagtgaaa aaggacctga tcatcaagct gcctaagtac | 3720 | |
| tccctgttcg agctggaaaa cggccggaag agaatgctgg cctctgccgg cgaactgcag | 3780 | |
| aagggaaacg aactggccct gcctccaaa tatgtgaact tcctgtacct ggccagccac | 3840 | |
| tatgagaagc tgaagggctc ccccgaggat aatgagcaga acagctgtt tgtgaacag | 3900 | |
| cacaagcact acctggacga gatcatcgag cagatcagcg agttctccaa gagagtgatc | 3960 | |
| ctggccgacg ctaatctgga caaagtgctg tccgcctaca acaagcaccg ggataagccc | 4020 | |
| atcagagagc aggccgagaa tatcatccac ctgtttaccc tgaccaatct gggagcccct | 4080 | |
| gccgccttca gtactttga caccaccatc gaccggaaga gtacaccag caccaaagag | 4140 | |
| gtgctggacg ccaccctgat ccaccagagc atcaccggcc tgtacgagac acggatcgac | 4200 | |
| ctgtctcagc tgggaggcga caaaaggccg gcggccacga aaaggccgg ccaggcaaaa | 4260 | |
| aagaaaaagt aa | 4272 | |

<210> SEQ ID NO 23
<211> LENGTH: 1968
<212> TYPE: DNA
<213> ORGANISM: Artificial Sequence
<220> FEATURE:
<223> OTHER INFORMATION: Synthetic Construct

<400> SEQUENCE: 23

| | | |
|---|---|---|
| atgccaaaga agaagcggaa ggtcgagtcc acgggaggcc agcatgtcc gccgggacgc | 60 | |
| accgtgacta agcgttcctg ggccctggcc gaggacaccc ctcgtggccc cgacagcccc | 120 | |
| cccaagcgcc cccgccctaa cagtcttccg ctgacaacca ccttccgtcc cctgcccccc | 180 | |
| ccaccccaga cgacgtcagc tgtggaccca agctcccatt cgcccgataa ccccccacgt | 240 | |
| gatcagcacg ccaccgacac cgcagacgaa aagccccggg ccgcgtcgcc ggcactttct | 300 | |
| gacgcctcag gcctccgac cccagacatt ccgctatctc ctggggggcac ccacgcccgc | 360 | |
| gacccggacg ccgatcccga ctccccggac cttgactcta tgtggtcggc gtcggtgatc | 420 | |
| cccaacgcgc tgccctccca tatactagcc gagacgttcg agcgccacct gcgcgggttg | 480 | |
| ctgcgcggcg tccgcgcccc cctggccatc ggtcccctct gggcccgcct ggattatctg | 540 | |
| tgttccctgg ccgtggtcct cgaggaggcg ggtatggtgg accgcggact cggccggcac | 600 | |
| ctatggcgcc tgacgcgccg cgggcccccg ccgccgcgg acgccgtggc gccccggccc | 660 | |
| ctcatggggt tttacgaggc ggccacgcaa aaccaggccg actgcagct atgggccctg | 720 | |
| ctccggcggg gcctcacgac cgcatccacc ctccgctggg gccccaggg tccgtgtttc | 780 | |

| | |
|---|---|
| tcgccccagt ggctgaagca caacgccagc ctgcggccgg atgtacagtc ttcggcggtg | 840 |
| atgttcgggc gggtgaacga gccgacggcc cgaagcctgc tgtttcgcta ctgcgtgggc | 900 |
| cgcgcggacg acggcggcga ggccggcgcc gacacgcggc gctttatctt ccacgaaccc | 960 |
| ggcgacctcg ccgaagagaa cgtgcatacg tgtggggtcc tcatggacgg tcacacgggg | 1020 |
| atggtcgggg cgtccctgga tattctcgtc tgtcctcggg acactcacgg ctacctggcc | 1080 |
| ccagtcccca agaccccct ggccttttac gaggtcaaat gccgggccaa gtacgctttc | 1140 |
| gaccccatgg accccagcga ccccacggcc tccgcgtacg aggacttgat ggcacaccgg | 1200 |
| tccccggagg cgttccgggc atttatccgg tcgatcccga agcccagcgt gcgatacttc | 1260 |
| gcgcccgggc gcgtccccgg cccggaggag gctctcgtca cgcaagacca ggcctggtca | 1320 |
| gaggcccacg cctcgggcga aaaaaggcgg tgctccgccg cggatcgggc cttggtggag | 1380 |
| ttaaatagcg gcgttgtctc ggaggtgctt ctgtttggcg ccccgacct cggacgccaa | 1440 |
| accatctccc ccgtgtcctg gagctccggg gatctggtcc gccgcgagcc cgtcttcgcg | 1500 |
| aaccccgtc acccgaactt taagcagatc ttggtgcagg gctacgtgct cgacagccac | 1560 |
| ttccccgact gccccccca cccgcatctg gtgacgttta cggcaggca ccgcaccagc | 1620 |
| gcggaggagg gcgtaacgtt ccgcctggag gacggcgccg gggctctcgg ggccgcagga | 1680 |
| cccagcaagg cgtccattct cccgaaccag gccgttccga tcgccctgat cattacccc | 1740 |
| gtccgcatcg atccggagat ctataaggcc atccagcgaa gcagccgcct ggcgttcgac | 1800 |
| gacacgctcg ccgagctatg ggcctctcgt tctccggggc ccggccctgc tgctgccgaa | 1860 |
| acaacgtcct catcaccgac gacggggagg tcgtctcgcg actataagga ccacgacgga | 1920 |
| gactacaagg atcatgatat tgattacaaa gacgatgacg ataagtga | 1968 |

<210> SEQ ID NO 24
<211> LENGTH: 23
<212> TYPE: DNA
<213> ORGANISM: Artificial Sequence
<220> FEATURE:
<223> OTHER INFORMATION: Synthetic Construct

<400> SEQUENCE: 24
gctgtctccg ccgcccgcca tgg    23

<210> SEQ ID NO 25
<211> LENGTH: 23
<212> TYPE: DNA
<213> ORGANISM: Artificial Sequence
<220> FEATURE:
<223> OTHER INFORMATION: Synthetic Construct

<400> SEQUENCE: 25
gggggtcgcg gtcgccatgg cgg    23

<210> SEQ ID NO 26
<211> LENGTH: 24
<212> TYPE: DNA
<213> ORGANISM: Artificial Sequence
<220> FEATURE:
<223> OTHER INFORMATION: Synthetic Construct

<400> SEQUENCE: 26
gaaaagccac aatctcatat gagg    24

<210> SEQ ID NO 27
<211> LENGTH: 23

```
<212> TYPE: DNA
<213> ORGANISM: Artificial Sequence
<220> FEATURE:
<223> OTHER INFORMATION: Synthetic Construct

<400> SEQUENCE: 27
ggtattcact cctaaagcgt cgg                                         23

<210> SEQ ID NO 28
<211> LENGTH: 23
<212> TYPE: DNA
<213> ORGANISM: Artificial Sequence
<220> FEATURE:
<223> OTHER INFORMATION: Synthetic Construct

<400> SEQUENCE: 28
ccgacgcttt aggagtgaat acc                                         23

<210> SEQ ID NO 29
<211> LENGTH: 23
<212> TYPE: DNA
<213> ORGANISM: Artificial Sequence
<220> FEATURE:
<223> OTHER INFORMATION: Synthetic Construct

<400> SEQUENCE: 29
ccgacgcttt aggagtgaat acc                                         23

<210> SEQ ID NO 30
<211> LENGTH: 341
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 250, 251, 252, 253, 254, 255, 256, 257, 258, 259
<223> OTHER INFORMATION: n = A,T,C or G

<400> SEQUENCE: 30
gagggcctat ttcccatgat tccttcatat ttgcatatac gatacaaggc tgttagagag   60
ataattggaa ttaatttgac tgtaaacaca aagatattag tacaaaatac gtgacgtaga  120
aagtaataat ttcttgggta gttttgcagtt ttaaaattat gttttaaaat ggactatcat 180
atgcttaccg taacttgaaa gtatttcgat ttcttggctt tatatatctt gtggaaagga  240
cgaaacaccn nnnnnnnng ttttagagct agaaatagca agttaaaata aggctagtcc   300
gttatcaact tgaaaaagtg gcaccgagtc ggtgcttttt t                      341

<210> SEQ ID NO 31
<211> LENGTH: 109
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 20, 21, 22, 23, 24, 25, 26, 27, 28, 29
<223> OTHER INFORMATION: n = A,T,C or G

<400> SEQUENCE: 31
taatacgact cactataggn nnnnnnnng ttttagagct agaaatagca agttaaaata    60
aggctagtcc gttatcaact tgaaaaagtg gcaccgagtc ggtgctttt              109

<210> SEQ ID NO 32
```

<210> SEQ ID NO 32
<211> LENGTH: 27
<212> TYPE: DNA
<213> ORGANISM: Artificial Sequence
<220> FEATURE:
<223> OTHER INFORMATION: Synthetic Construct

<400> SEQUENCE: 32
agtggagtca gtgatgccat tggcctc          27

<210> SEQ ID NO 33
<211> LENGTH: 26
<212> TYPE: DNA
<213> ORGANISM: Artificial Sequence
<220> FEATURE:
<223> OTHER INFORMATION: Synthetic Construct

<400> SEQUENCE: 33
gcctttggtg ctcttcatct tgttgg           26

<210> SEQ ID NO 34
<211> LENGTH: 26
<212> TYPE: DNA
<213> ORGANISM: Artificial Sequence
<220> FEATURE:
<223> OTHER INFORMATION: Synthetic Construct

<400> SEQUENCE: 34
tacccgtgat attgctgaag agcttg           26

<210> SEQ ID NO 35
<211> LENGTH: 25
<212> TYPE: DNA
<213> ORGANISM: Artificial Sequence
<220> FEATURE:
<223> OTHER INFORMATION: Synthetic Construct

<400> SEQUENCE: 35
tttggtagtg ggcaccagct atctg            25

<210> SEQ ID NO 36
<211> LENGTH: 27
<212> TYPE: DNA
<213> ORGANISM: Artificial Sequence
<220> FEATURE:
<223> OTHER INFORMATION: Synthetic Construct

<400> SEQUENCE: 36
ggtattcagc caaacgacca tctgccg          27

<210> SEQ ID NO 37
<211> LENGTH: 23
<212> TYPE: DNA
<213> ORGANISM: Artificial Sequence
<220> FEATURE:
<223> OTHER INFORMATION: Synthetic Construct

<400> SEQUENCE: 37
agtcgtgctg cttcatgtgg tcg              23

<210> SEQ ID NO 38
<211> LENGTH: 26
<212> TYPE: DNA
<213> ORGANISM: Artificial Sequence
<220> FEATURE:
<223> OTHER INFORMATION: Synthetic Construct

<400> SEQUENCE: 38
tgacacgtgc tacgagattt cgattc                                          26

<210> SEQ ID NO 39
<211> LENGTH: 27
<212> TYPE: DNA
<213> ORGANISM: Artificial Sequence
<220> FEATURE:
<223> OTHER INFORMATION: Synthetic Construct

<400> SEQUENCE: 39
acaggcttca cctgtactgt cagggca                                         27

<210> SEQ ID NO 40
<211> LENGTH: 46
<212> TYPE: DNA
<213> ORGANISM: Artificial Sequence
<220> FEATURE:
<223> OTHER INFORMATION: Synthetic Construct

<400> SEQUENCE: 40
cagacgtacc agtcagtcta cttcgtgtct gagagcttca gtgacg                    46

<210> SEQ ID NO 41
<211> LENGTH: 46
<212> TYPE: DNA
<213> ORGANISM: Artificial Sequence
<220> FEATURE:
<223> OTHER INFORMATION: Synthetic Construct

<400> SEQUENCE: 41
ctcctctcaa ggaggcaccc atgtcctctc cagctgccgg gcctca                    46

<210> SEQ ID NO 42
<211> LENGTH: 45
<212> TYPE: DNA
<213> ORGANISM: Artificial Sequence
<220> FEATURE:
<223> OTHER INFORMATION: Synthetic Construct

<400> SEQUENCE: 42
gatacccggg gaccttccct ttcttggcct aatttccatt gcttc                     45

<210> SEQ ID NO 43
<211> LENGTH: 46
<212> TYPE: DNA
<213> ORGANISM: Artificial Sequence
<220> FEATURE:
<223> OTHER INFORMATION: Synthetic Construct

<400> SEQUENCE: 43
gtgggttaag cggtttgatt cacactgaac caggccagcc cagttg                    46

<210> SEQ ID NO 44
<211> LENGTH: 24
<212> TYPE: DNA
<213> ORGANISM: Artificial Sequence
<220> FEATURE:
<223> OTHER INFORMATION: Synthetic Construct

<400> SEQUENCE: 44
ggacgccgtg cacctagcca atgg                                            24

<210> SEQ ID NO 45
<211> LENGTH: 23
<212> TYPE: DNA

```
<213> ORGANISM: Artificial Sequence
<220> FEATURE:
<223> OTHER INFORMATION: Synthetic Construct

<400> SEQUENCE: 45
tctcccatgc attcaaactg agg                                              23
```

DNA KNOCK-IN SYSTEM

CROSS-REFERENCE TO RELATED APPLICATIONS

This application is a continuation of U.S. patent application Ser. No. 15/503,695, filed on Feb. 13, 2017, which is a U.S. National Phase Application under 35 U.S.C. § 371 of International Application No. PCT/US2015/045134, filed on Aug. 13, 2015, which claims priority benefit to U.S. Provisional Patent Application No. 62/037,551, filed on Aug. 14, 2014, the contents of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 735782000101SEQLIST.TXT, date recorded: Sep. 11, 2017, size: 24 KB).

TECHNICAL FIELD

The present invention relates to an enhanced DNA knock-in (EKI) system and uses thereof.

BACKGROUND

Recent developments in DNA manipulation allows for effective introduction of exogenous genes into the chromosome of a host cell (gene knock-in). This allows the insertion of a protein coding cDNA sequence at a particular locus in an organism's genome, for example, insertion of a mutation or exogenous gene at a particular locus on a chromosome. For example, a point mutation can be introduced into a target gene by knock-in to model human genetic disorders. In addition, exogenous genes such as reporter genes (EGFP, mRFP, mCherry, tdTomato etc.) can be introduced by homologous recombination into a particular locus of the target gene, and can be used to track expression of the target gene and study its expression profiles by expression of the reporter gene.

In many circumstances, gene knock-in involves homologous recombination mechanisms in an organism. Under natural circumstances, the probability of homologous recombination between an exogenous targeting vector and the genome of a cell is very low, about $1/10^5$ to $1/10^6$. Spontaneous gene targeting typically occurs at a very low frequency in mammalian cells with an efficiency of 1 in a million cells. The presence of a double-strand break is often recombinogenic and increases the homologous recombination frequency by several thousand folds. See Jasin, 1996, "Genetic manipulation of genomes with rare-cutting endonucleases," Trends in genetics: TIG 12(6): 224-228. In plants, the generation of a double-strand break in DNA is known to increase the frequency of homologous recombination from a background level of about $10^{-3}$-$10^{-4}$ by a factor of approximately 100-fold. See Hanin et al., 2001, "Gene targeting in Arabidopsis," Plant J. 28:671-77. Generation of genetically modified mice via homologous recombination was made possible by the establishment of murine embryonic stem cell lines. For example, targeting vectors can be constructed using bacterial artificial chromosome (BAC), and introduced into murine embryonic stem cells via transfection (e.g., electroporation). Positive embryonic stem cell clones are selected and injected into mouse blastocysts microscopic cell mass, and then implanted into a surrogate mouse to produce genetically engineered chimeric mouse. However, methods for establishing embryonic stem cell lines from other species have not been as successful and widely used.

Recently developed techniques, including ZFNs (zinc finger nucleases), TALENs (transcription activator-like effector nucleases), CRISPR (clustered regularly interspaced short palindromic repeats)/Cas9, and other site-specific nuclease technologies, made it possible to create double-strand DNA breaks at desired locus sites. These controlled double-strand breaks can promote homologous recombination at such specific locus sites. This process relies on targeting specific sequences of nucleic acid molecules, such as chromosomes, with endonucleases that recognize and bind to such sequences and induce a double-strand break in the nucleic acid molecule. The double-strand break is repaired either by an error-prone nonhomologous end-joining (NHEJ) or by homologous recombination (HR).

Homologous recombination that occurs during DNA repair tends to result in non-crossover products, in effect restoring the damaged DNA molecule as it existed before the double-strand break, or generating a recombinant molecule by incorporating sequence(s) of a template. The latter has been used in gene targeting, protein engineering, and gene therapy. If the template for homologous recombination is provided in trans (e.g., by introducing an exogenous template into a cell), the double-strand break in the cell can be repaired using the provided template. In gene targeting, the initial double-strand break increases the frequency of targeting by several orders of magnitude, compared to conventional homologous recombination-based gene targeting. In principle, this method could be used to insert any sequence at the site of repair so long as it is flanked by appropriate regions homologous to the sequences near the double-strand break. Although this method has had success in various species such as mice and rats, the efficiency and success rate of homologous recombination remain low, preventing the method from being widely used. For instance, the method remains costly and technically challenging for both scientific and commercial use.

The disclosures of all publications, patents, patent applications and published patent applications referred to herein are hereby incorporated herein by reference in their entirety.

BRIEF SUMMARY OF THE INVENTION

In one embodiment, disclosed herein is a method of inserting a donor sequence at a predetermined insertion site on a chromosome in an eukaryotic cell, comprising: (a) introducing into the cell a sequence-specific nuclease that cleaves the chromosome at the insertion site; (b) introducing into the cell a donor construct; and (c) introducing into the cell an exonuclease. In one aspect, the donor construct is a linear nucleic acid or cleaved within the cell to produce a linear nucleic acid. In another aspect, the linear nucleic acid comprises a 5' homology arm, the donor sequence, and a 3' homology arm. In certain aspects, the 5' homology arm is homologous to a sequence upstream of the nuclease cleavage site on the chromosome, and the 3' homology arm is homologous to a sequence downstream of the cleavage site on the chromosome. In some embodiments, the 5' homology arm and the 3' homology arm are proximal to the 5' and 3' ends of the linear nucleic acid, respectively. In other embodiments, the donor sequence is inserted into the chromosome at the insertion site through homologous recombination.

In some embodiments, the sequence-specific nuclease used herein is a zinc finger nuclease (ZFN). In some embodiments, the sequence-specific nuclease used herein is a transcription activator-like effector nuclease (TALEN). In some embodiments, the sequence-specific nuclease used herein is an RNA-guided nuclease. In one aspect, the RNA-guided nuclease is Cas, for example, Cas9.

In any of the preceding embodiments involving an RNA-guided nuclease, the method can further comprise introducing into the cell a guide RNA (gRNA) recognizing the insertion site.

In any of the preceding embodiments, the sequence-specific nuclease can be introduced into the cell as a protein, mRNA, or cDNA.

In some embodiments, the sequence homology between the 5' homology arm and the sequence 5' to the insertion site is at least about 80%. In some embodiments, the sequence homology between the 3' homology arm and the sequence 3' to the insertion site is at least about 80%. In any of the preceding embodiments, the 5' homology arm and the 3' homology arm can be at least about 200 base pair (bp).

In any of the preceding embodiments, the exonuclease can be a 5' to 3' exonuclease. In one aspect, the exonuclease is a herpes simplex virus type 1 (HSV-1) exonuclease. In one embodiment, the exonuclease is UL12.

In any of the preceding embodiments, the donor construct can be a linear nucleic acid. In some embodiments, the donor construct is circular when introduced into the cell and cleaved within the cell to produce a linear nucleic acid. In one aspect, the donor construct further comprises a 5' flanking sequence upstream of the 5' homology arm and a 3' flanking sequence downstream of the 3' homology arm. In one embodiment, the 5' flanking sequence or the 3' flanking sequence is about 1 to about 500 bp.

In some embodiments, a method disclosed herein further comprises introducing into the cell a second sequence-specific nuclease that cleaves the donor construct at one or both of the flanking sequences, thereby producing the linear nucleic acid. In certain embodiments, the sequence-specific nuclease is an RNA-guided nuclease, and the method further comprises introducing into the cell a second guide RNA recognizing one or both of the flanking sequences.

In any of the preceding embodiments, the eukaryotic cell can be a mammalian cell. In some embodiments, the mammalian cell is a zygote or a pluripotent stem cell.

In some aspects, disclosed herein is a method of generating a genetically modified animal, which comprises a donor sequence inserted at a predetermined insertion site on the chromosome of the animal. In one embodiment, the method comprises: (a) introducing into a cell a sequence-specific nuclease that cleaves the chromosome at the insertion site; (b) introducing into the cell a donor construct; (c) introducing into the cell an exonuclease; and (d) introducing the cell into a carrier animal to produce the genetically modified animal. In one embodiment, the donor construct is a linear nucleic acid or cleaved within the cell to produce a linear nucleic acid. In one aspect, the linear nucleic acid comprises a 5' homology arm, the donor sequence, and a 3' homology arm. In one aspect, the 5' homology arm is homologous to a sequence upstream of the nuclease cleavage site on the chromosome. In one aspect, the 3' homology arm is homologous to a sequence downstream of the cleavage site on the chromosome. In some embodiments, the 5' homology arm and the 3' homology arm are proximal to the 5' and 3' ends of the linear nucleic acid, respectively. In some embodiments, the donor sequence is inserted into the chromosome at the insertion site through homologous recombination.

In one aspect, the genetically modified animal is a rodent. In other aspects, the cell is a zygote or a pluripotent stem cell.

In some aspects, provided herein is a genetically modified animal generated by the method of any of the methods described above.

In other aspects, provided herein is a kit for inserting a donor sequence at an insertion site on a chromosome in an eukaryotic cell, comprising: (a) a sequence-specific nuclease that cleaves the chromosome at the insertion site; (b) a donor construct; and (c) an exonuclease. In one embodiment, the donor construct is a linear nucleic acid or can be cleaved within a cell to produce a linear nucleic acid. In one aspect, the linear nucleic acid comprises a 5' homology arm, the donor sequence, and a 3' homology arm. In one aspect, the 5' homology arm is homologous to a sequence upstream of the nuclease cleavage site on the chromosome. In one aspect, the 3' homology arm is homologous to a sequence downstream of the cleavage site on the chromosome. In one aspect, the 5' homology arm and the 3' homology arm are proximal to the 5' and 3' ends of the linear nucleic acid, respectively. In some embodiments, the sequence-specific nuclease is an RNA-guided nuclease. In other embodiments, the kit further comprises a guide RNA (gRNA) recognizing the insertion site.

In some embodiments, the donor construct is circular. In one aspect, the donor construct further comprises a 5' flanking sequence upstream of the 5' homology arm and a 3' flanking sequence downstream of the 3' homology arm. In another aspect, the 5' flanking sequence or the 3' flanking sequence is about 1 to about 500 bp. In any of the preceding embodiments, the sequence-specific nuclease can be an RNA-guided nuclease, and the kit can further comprise a second guide RNA recognizing one or both of the flanking sequences. In any of the preceding embodiments, the exonuclease can be a 5' to 3' exonuclease. In one aspect, the exonuclease is a herpes simplex virus type 1 (HSV-1) exonuclease. In another aspect, the exonuclease is UL12. In one embodiment, the UL12 is fused to a nuclear localization sequence (NLS).

In some embodiments, the present disclosure provides a method of producing a linear nucleic acid in an eukaryotic cell, in which the linear nucleic acid comprises a 5' homology arm, a donor sequence, and a 3' homology arm; the 5' homology arm is homologous to a sequence upstream of the nuclease cleavage site on the chromosome and the 3' homology arm is homologous to a sequence downstream of the cleavage site on the chromosome; and the 5' homology arm and the 3' homology arm are proximal to the 5' and 3' ends of the linear nucleic acid, respectively. In one aspect, the method comprises: (a) introducing into the cell a circular donor construct comprising the linear nucleic acid and further comprising a 5' flanking sequences upstream of the 5' homology arm and a 3' flanking sequence downstream of the 3' homology arm; and (b) introducing into the cell a sequence-specific nuclease, wherein the sequence-specific nuclease cleaves the circular donor construct at the 5' flanking sequence and the 3' flanking sequence, thereby producing the linear nucleic acid. In one aspect, the sequence-specific nuclease is ZFN. In another aspect, the sequence-specific nuclease is TALEN. In yet another aspect, the sequence-specific nuclease is an RNA-guided nuclease. In one embodiment, the RNA-guided nuclease is Cas. In some embodiments, the RNA-guided nuclease is Cas9. In any of the preceding embodiments, the method can further comprise introducing into the cell a guide RNA recognizing the 5' flanking sequence and/or the 3' flanking sequence.

BRIEF DESCRIPTION OF THE FIGURES

FIG. 2 shows fluorescent microscopic images indicating the expression of the EGFP-ACTB fusion protein in U2OS cells after knocking in using the enhanced knock-in ("EKI") system.

FIGS. 3A, 3B AND 3C depict flow cytometry results showing that the knock-in efficiency of EGFP-ACTB in U2OS cells was significantly increased using the EKI system, compared to conventional CRISPR/Cas9-mediated knock-in. FIG. 3A shows the result of a control experiment, FIG. 3B shows the result of conventional CRISPR/Cas9-mediated knock-in, and FIG. 3C shows the result of the EKI system-mediated knock-in.

FIG. 5 shows fluorescent microscopic images indicating the expression of the EGFP-LMNB1 fusion protein in C6 cells after knocking in using the EKI system.

FIGS. 6A, 6B AND 6C depict flow cytometry results showing that the knock-in efficiency of EGFP-LMNB1 in C6 cells was significantly increased using the EKI system, compared to conventional CRISPR/Cas9-mediated knock-in. FIG. 6A shows the result of a control experiment, FIG. 6B shows the result of conventional CRISPR/Cas9-mediated knock-in, and FIG. 6C shows the result of the EKI system-mediated knock-in.

FIGS. 7A AND 7B depict a targeting scheme for double knock-in of EGFP-ACTB and mCherry-LMNB1 in the U2OS cell line. FIG. 7A depicts the targeting scheme for knocking in EGFP-ACTB, and FIG. 7B depicts the targeting scheme for knocking in mCherry-LMNB1.

FIG. 12A shows the southern blot strategy, and FIG. 12B shows the southern blot results using the 5' probe, 3' probe, and dsRed probe. The two F1 rats (#19 and #21) tested with southern blots were the offspring of the #22 F0 rat in FIG. 10 and FIG. 11. WT: wild-type rat. PC: positive control.

FIGS. 16A AND 16B depict genotyping results of TH-GFP knock-in in H9 cells. FIG. 16A depicts the 5'-junction PCR reaction results, and FIG. 16B depicts the 3'-junction PCR reaction results. WT: wild-type H9 cells.

FIGS. 22A, 22B AND 22C depict genotyping results of OCT4-EGFP knock-in in H9 cells. FIG. 22A depicts the 5'-junction PCR reaction results, FIG. 22B depicts the 3'-junction PCR reaction results, and FIG. 22C depicts the full length PCR reaction results. wt: wild-type H9 cells. c-: $H_2O$ as negative control.

DETAILED DESCRIPTION OF THE INVENTION

Figure 1:
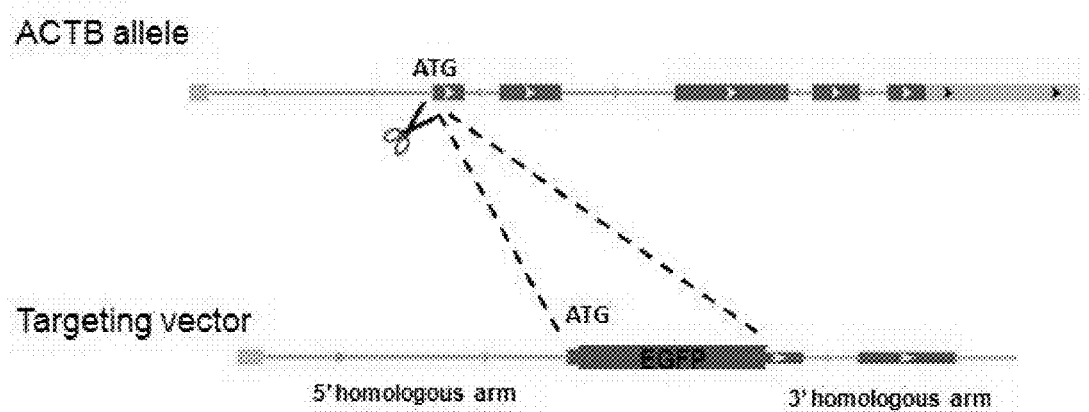
FIG. 1 depicts a targeting scheme for knocking in EGFP-ACTB in the U2OS cell line.

The present invention provides a novel DNA knock-in method which allows for the introduction of one or more exogenous sequences into a specific target site on the cellular chromosome with significantly higher efficiency compared to traditional DNA knock-in methods using sequence-specific nucleases such as CRISPR/Cas9 or TALEN-based gene knock-in systems. In addition to the use of a sequence-specific nuclease, the method of the present application further utilizes an exonuclease (such as a 5' to 3' exonuclease, for example UL12) in conjunction with a donor construct which is either a linear nucleic acid or can be cleaved within the cell to produce a linear nucleic acid. The DNA knock-in system allows donor sequences to be inserted at any desired target site with high efficiency, making it feasible for many uses such as creation of transgenic animals expressing exogenous genes, modifying (e.g., mutating) a genomic locus, and gene editing, for example by adding an exogenous non-coding sequence (such as sequence tags or regulatory elements) into the genome. The cells and animals produced using methods provided herein can find various applications, for example as cellular therapeutics, as disease models, as research tools, and as humanized animal useful for various purposes.

Thus, the present application in one aspect provides methods of inserting a donor sequence at a predetermined insertion site on a chromosome of an eukaryotic cell.

In another aspect, there are provided methods of generating a linear nucleic acid in a cell.

In another aspect, there is provided a kit for use in any one of the methods described herein.

In another aspect, there is provided a method of generating a genetically modified animal by using the gene knock-in system described herein.

Reference to "about" a value or parameter herein includes (and describes) variations that are directed to that value or parameter per se. For example, description referring to "about X" includes description of "X".

As used herein and in the appended claims, the singular forms "a", "or", and "the" include plural referents unless the context clearly dictates otherwise.

The compositions and methods of the present invention may comprise, consist of, or consist essentially of the essential elements and limitations of the invention described herein, as well as any additional or optional ingredients, components, or limitations described herein or otherwise useful in a nutritional or pharmaceutical application.

Methods of the Present Invention

The present invention provides methods of inserting a donor sequence at a predetermined insertion site on a chromosome in an eukaryotic cell. In some embodiments the method comprises: a) introducing into the cell a sequence-specific nuclease that cleaves the chromosome at the insertion site; b) introducing into the cell a donor construct; and c) introducing into the cell an exonuclease; wherein the donor construct is a linear nucleic acid or cleaved within the cell to produce a linear nucleic acid, wherein the linear nucleic acid comprises a 5' homology arm, the donor sequence, and a 3' homology arm, wherein the 5' homology arm is homologous to a sequence upstream of the nuclease cleavage site on the chromosome and wherein the 3' homology arm is homologous to a sequence downstream of the nuclease cleavage site on the chromosome; wherein the 5' homology arm and the 3' homology arm are proximal to the 5' and 3' ends of the linear nucleic acid, respectively, and wherein the donor sequence is inserted into the chromosome at the insertion site through homologous recombination.

In some embodiments, the sequence-specific nuclease, the exonuclease, and the donor construct are introduced into the cell simultaneously. In some embodiments, at least one of the three components is introduced into the cell at a different time from the other component(s). For example, the donor construct may be introduced into the cell first, and the sequence-specific nuclease and the exonuclease are subsequently introduced. In some embodiments, the sequence-specific nuclease is introduced into the cell first, and the donor construct and the exonuclease are subsequently introduced. In some embodiments, all three components are introduced at a different time point relative to each other. For example, the three components can be administered in a sequence, one after another at a specific order.

In some embodiments, the sequence-specific nuclease and/or the exonuclease are introduced into the cell as a cDNA. In some embodiments, the sequence-specific nuclease and/or the exonuclease are introduced into the cell as an mRNA. In some embodiments, the sequence-specific nuclease and/or the exonuclease are introduced into the cell as a protein.

For example, in some embodiments, there is provided a method of inserting a donor sequence at a predetermined insertion site on a chromosome in an eukaryotic cell, the method comprising: a) introducing into the cell a nucleic acid sequence encoding a sequence-specific nuclease that cleaves the chromosome at the insertion site; b) introducing into the cell a donor construct; and c) introducing into the cell a nucleic acid sequence encoding an exonuclease; wherein the donor construct is a linear nucleic acid or cleaved within the cell to produce a linear nucleic acid, wherein the linear nucleic acid comprises a 5' homology arm, the donor sequence, and a 3' homology arm, wherein the 5' homology arm is homologous to a sequence upstream of the nuclease cleavage site on the chromosome and wherein the 3' homology arm is homologous to a sequence downstream of the nuclease cleavage site on the chromosome; wherein the 5' homology arm and the 3' homology arm are proximal to the 5' and 3' ends of the linear nucleic acid, respectively, and wherein the donor sequence is inserted into the chromosome at the insertion site through homologous recombination. In some embodiments, the nucleic acid encoding the sequence-specific nuclease and/or the nucleic acid encoding the exonuclease is mRNA. In some embodiments, the nucleic acid encoding the sequence-specific nuclease and/or the nucleic acid encoding the exonuclease is cDNA. In some embodiments, the nucleic acid encoding the sequence-specific nuclease and/or the nucleic acid encoding the exonuclease is introduced into the cell by transfection (including for example transfection through electroporation). In some embodiments, the nucleic acid encoding the sequence-specific nuclease and/or the nucleic acid encoding the exonuclease is introduced into the cell by injection.

In some embodiments, there is provided a method of inserting a donor sequence at a predetermined insertion site on a chromosome in an eukaryotic cell, the method comprising: a) introducing into the cell a vector comprising a nucleic acid sequence encoding a sequence-specific nuclease that cleaves the chromosome at the insertion site; b) introducing into the cell a donor construct; and c) introducing into the cell a vector comprising a nucleic acid sequence encoding an exonuclease; wherein the donor construct is a linear nucleic acid or cleaved within the cell to produce a linear nucleic acid, wherein the linear nucleic acid comprises a 5' homology arm, the donor sequence, and a 3' homology arm, wherein the 5' homology arm is homologous to a sequence upstream of the nuclease cleavage site on the chromosome and wherein the 3' homology arm is homologous to a sequence downstream of the nuclease cleavage site on the chromosome; wherein the 5' homology arm and the 3' homology arm are proximal to the 5' and 3' ends of the linear nucleic acid, respectively, and wherein the donor sequence is inserted into the chromosome at the insertion site through homologous recombination. In some embodiments, the vector comprising the nucleic acid encoding the sequence-specific nuclease and/or the vector comprising the nucleic acid encoding the exonuclease is introduced into the cell by transfection (including for example transfection through electroporation).

In some embodiments, there is provided a method of inserting a donor sequence at a predetermined insertion site on a chromosome in an eukaryotic cell, the method comprising: a) introducing into the cell a vector comprising a nucleic acid sequence encoding a sequence-specific nuclease that cleaves the chromosome at the insertion site and a nucleic acid sequence encoding an exonuclease; b) introducing into the cell a donor construct; wherein the donor construct is a linear nucleic acid or cleaved within the cell to produce a linear nucleic acid, wherein the linear nucleic acid comprises a 5' homology arm, the donor sequence, and a 3' homology arm, wherein the 5' homology arm is homologous to a sequence upstream of the nuclease cleavage site on the chromosome and wherein the 3' homology arm is homologous to a sequence downstream of the nuclease cleavage site on the chromosome; wherein the 5' homology arm and the 3' homology arm are proximal to the 5' and 3' ends of the linear nucleic acid, respectively, and wherein the donor sequence is inserted into the chromosome at the insertion site through homologous recombination. In some embodiments, the vector comprising the nucleic acid encoding the sequence-specific nuclease and the nucleic acid encoding the exonuclease is introduced into the cell by transfection (including for example transfection through electroporation).

In some embodiments, there is provided a method of inserting a donor sequence at a predetermined insertion site on a chromosome in an eukaryotic cell (such as a zygotic cell), the method comprising: a) introducing (such as injecting) into the cell an mRNA sequence encoding a sequence-specific nuclease that cleaves the chromosome at the insertion site; b) introducing (such as injecting) into the cell a donor construct; and c) introducing (such as injecting) into the cell an mRNA sequence encoding an exonuclease; wherein the donor construct is a linear nucleic acid or cleaved within the cell to produce a linear nucleic acid, wherein the linear nucleic acid comprises a 5' homology arm, the donor sequence, and a 3' homology arm, wherein the 5' homology arm is homologous to a sequence upstream of the nuclease cleavage site on the chromosome and wherein the 3' homology arm is homologous to a sequence downstream of the nuclease cleavage site on the chromosome; wherein the 5' homology arm and the 3' homology arm are proximal to the 5' and 3' ends of the linear nucleic acid, respectively, and wherein the donor sequence is inserted into the chromosome at the insertion site through homologous recombination. In some embodiments, the introduction (such as injection) is carried out in vitro. In some embodiments, the introduction (such as injection) is carried out in vivo. In some embodiments, the method further comprises transcribing in vitro a nucleic acid encoding the sequence-specific nuclease into mRNA. In some embodiments, the method further comprises transcribing in vitro a nucleic acid encoding the exonuclease into mRNA.

For example, in some embodiments, there is provided a method of inserting a donor sequence at a predetermined insertion site on a chromosome in an immune cell (such as T cells), the method comprising: a) introducing into the cell a nucleic acid sequence encoding a sequence-specific nuclease that cleaves the chromosome at the insertion site; b) introducing into the cell a donor construct; and c) introducing into the cell a nucleic acid sequence encoding an exonuclease; wherein the donor construct is a linear nucleic acid or cleaved within the cell to produce a linear nucleic acid, wherein the linear nucleic acid comprises a 5' homology arm, the donor sequence, and a 3' homology arm, wherein the 5' homology arm is homologous to a sequence upstream of the nuclease cleavage site on the chromosome and wherein the 3' homology arm is homologous to a sequence downstream of the nuclease cleavage site on the chromosome; wherein the 5' homology arm and the 3' homology arm are proximal to the 5' and 3' ends of the linear nucleic acid, respectively, and wherein the donor sequence is inserted into the chromosome at the insertion site through homologous recombination. In some embodiments, the nucleic acid encoding the sequence-specific nuclease and/or the nucleic acid encoding the exonuclease is mRNA. In some embodiments, the nucleic acid encoding the sequence-specific nuclease and/or the nucleic acid encoding the exonuclease is cDNA. In some embodiments, the nucleic acid encoding the sequence-specific nuclease and/or the nucleic acid encoding the exonuclease is introduced into the cell by transfection (including for example transfection through electroporation). In some embodiments, the nucleic acid encoding the sequence-specific nuclease and/or the nucleic acid encoding the exonuclease is introduced into the cell by injection.

In some embodiments, there is provided a method of inserting a donor sequence at a predetermined insertion site on a chromosome in an immune cell (such as T cells), the method comprising: a) introducing into the cell a vector comprising a nucleic acid sequence encoding a sequence-specific nuclease that cleaves the chromosome at the insertion site; b) introducing into the cell a donor construct; and c) introducing into the cell a vector comprising a nucleic acid sequence encoding an exonuclease; wherein the donor construct is a linear nucleic acid or cleaved within the cell to produce a linear nucleic acid, wherein the linear nucleic acid comprises a 5' homology arm, the donor sequence, and a 3' homology arm, wherein the 5' homology arm is homologous to a sequence upstream of the nuclease cleavage site on the chromosome and wherein the 3' homology arm is homologous to a sequence downstream of the nuclease cleavage site on the chromosome; wherein the 5' homology arm and the 3' homology arm are proximal to the 5' and 3' ends of the linear nucleic acid, respectively, and wherein the donor sequence is inserted into the chromosome at the insertion site through homologous recombination. In some embodiments, the vector comprising the nucleic acid encoding the sequence-specific nuclease and/or the vector comprising the nucleic acid encoding the exonuclease is introduced into the cell by transfection (including for example transfection through electroporation).

In some embodiments, there is provided a method of inserting a donor sequence at a predetermined insertion site on a chromosome in an immune cell (such as T cells), the method comprising: a) introducing into the cell a vector comprising a nucleic acid sequence encoding a sequence-specific nuclease that cleaves the chromosome at the insertion site and a nucleic acid sequence encoding an exonuclease; b) introducing into the cell a donor construct; wherein the donor construct is a linear nucleic acid or cleaved within the cell to produce a linear nucleic acid, wherein the linear nucleic acid comprises a 5' homology arm, the donor sequence, and a 3' homology arm, wherein the 5' homology arm is homologous to a sequence upstream of the nuclease cleavage site on the chromosome and wherein the 3' homology arm is homologous to a sequence downstream of the nuclease cleavage site on the chromosome; wherein the 5' homology arm and the 3' homology arm are proximal to the 5' and 3' ends of the linear nucleic acid, respectively, and wherein the donor sequence is inserted into the chromosome at the insertion site through homologous recombination. In some embodiments, the vector comprising the nucleic acid encoding the sequence-specific nuclease and the nucleic acid encoding the exonuclease is introduced into the cell by transfection (including for example transfection through electroporation).

In some embodiments, there is provided a method of inserting a donor sequence at a predetermined insertion site on a chromosome in an immune cell (such as T cells), the method comprising: a) introducing (such as injecting) into the cell an mRNA sequence encoding a sequence-specific nuclease that cleaves the chromosome at the insertion site; b) introducing (such as injecting) into the cell a donor construct; and c) introducing (such as injecting) into the cell an mRNA sequence encoding an exonuclease; wherein the donor construct is a linear nucleic acid or cleaved within the cell to produce a linear nucleic acid, wherein the linear nucleic acid comprises a 5' homology arm, the donor sequence, and a 3' homology arm, wherein the 5' homology arm is homologous to a sequence upstream of the nuclease cleavage site on the chromosome and wherein the 3' homology arm is homologous to a sequence downstream of the nuclease cleavage site on the chromosome; wherein the 5' homology arm and the 3' homology arm are proximal to the 5' and 3' ends of the linear nucleic acid, respectively, and wherein the donor sequence is inserted into the chromosome at the insertion site through homologous recombination. In some embodiments, the introduction (such as injection) is carried out in vitro. In some embodiments, the introduction (such as injection) is carried out in vivo. In some embodiments, the method further comprises transcribing in vitro a nucleic acid encoding the sequence-specific nuclease into mRNA. In some embodiments, the method further comprises transcribing in vitro a nucleic acid encoding the exonuclease into mRNA.

The cells described herein can be any eukaryotic cell, e.g., an isolated cell of an animal, such as a totipotent, pluripotent, or adult stem cell, a zygote, or a somatic cell. In some embodiments, the cell is from a primary cell culture. In some embodiments, cells for use in the methods are human cells. In some embodiments, cells for use in the methods are yeast cells. In some embodiments, the cell is from a domesticated animal (e.g., cow, sheep, cat, dog, and horse). In some embodiments, the cell is from a primate (e.g., non-human primate such as monkey). In some embodiments, the cell is from a rabbit. In some embodiments, the cell is from a fish (such as zebrafish). In some embodiments, the cell is from a rodent (e.g., mouse, rat, hamster, guinea pig). In some embodiments, the cell is from a non-vertebrate (e.g., *Drosophila melanogaster* and *Caenorhabditis elegans*).

The cells described herein can be immune cells, which include, but are not limited to, granulocytes (such as basophils, eosinophils, and neutrophils), mast cells, monocytes, dendritic cells (DC), natural killer (NK) cells, B cells, and T cells (such as CD8+ T cells, and CD4+ T cells). In some embodiments, the cell is a CD4+ T cell (e.g., T helper cells TH1, TH2, TH17, and regulatory T cells).

The methods and compositions described herein can be used to insert a donor sequence into one or more genomic locus in the cell. In certain embodiments, the methods and compositions described herein can be used to target more than one genomic locus within a cell, e.g., for double DNA knock-in. In certain embodiments, the methods and compositions described herein are used to target two, three, four, five, six, seven, eight, nine, ten, or more than ten genomic loci within a cell. In some aspects, the double or multiple knock-in can be carried out simultaneously or sequentially. For example, the reagents for targeting the two or more genomic loci within the same cell are mixed and introduced into the cell at substantially the same time. In other embodiments, reagents that target each of the multiple genomic loci can be introduced into the cell in a sequence, one after another at a specific order. In yet other embodiments, a first genomic locus is targeted and cells with successful knock-in are selected, enriched, and/or separated, and are subjected to targeting a second genomic locus.

Double or multiple knock-in can be accomplished, for example, by using two or more different sequence-specific nucleases, each recognizing a sequence at one of the predetermined insertion sites. These sequence-specific nucleases can be introduced into a cell simultaneously or sequentially. Thus, for example, in some embodiments, there is provided a method of inserting two or more donor sequences, each at a predetermined insertion sites on a chromosome in an eukaryotic cell, comprising: a) introducing into the cell one or more sequence-specific nucleases that cleave the chromosome at the predetermined insertion sites; b) introducing into the cell two or more donor constructs; and c) introducing into the cell an exonuclease, wherein each of the donor construct is a linear nucleic acid or cleaved within the cell to produce a linear nucleic acid, wherein the linear nucleic acid comprises a 5' homology arm, the donor sequence, and a 3' homology arm, wherein the 5' homology arm is homologous to a sequence upstream of the corresponding nuclease cleavage site on the chromosome, and wherein the 3' homology arm is homologous to a sequence downstream of the corresponding nuclease cleavage site on the chromosome, wherein the 5' homology arm and the 3' homology arm are proximal to the 5' and 3' ends of the linear nucleic acid, respectively, and wherein the two or more donor sequences are inserted into the chromosome at the predetermined insertion sites through homologous recombination. In some embodiments, there is provided a method of inserting two donor sequences, each at a predetermined insertion site on a chromosome in an eukaryotic cell, comprising: a) introducing into the cell a first sequence-specific nuclease that cleaves the chromosome at a first predetermined insertion site; b) introducing into the cell a first donor construct; c) introducing into the cell a second sequence-specific nuclease that cleaves the chromosome at a second predetermined insertion site; and d) introducing into the cell a second donor construct; and e) introducing into the cell an exonuclease, wherein each of the donor construct is a linear nucleic acid or cleaved within the cell to produce a linear nucleic acid, wherein the linear nucleic acid comprises a 5' homology arm, the donor sequence, and a 3' homology arm, wherein the 5' homology arm is homologous to a sequence upstream of the corresponding nuclease cleavage site on the chromosome, and wherein the 3' homology arm is homologous to a sequence downstream of the corresponding nuclease cleavage site on the chromosome, wherein the 5' homology arm and the 3' homology arm are proximal to the 5' and 3' ends of the linear nucleic acid, respectively, and wherein the two donor sequences are inserted into the chromosome at the predetermined insertion sites through homologous recombination.

The sequence-specific nuclease (and exonuclease described herein) can be introduced into the cell in form of a protein or in form of a nucleic acid encoding the sequence-specific nuclease (and exonuclease described herein), such as an mRNA or a cDNA. Nucleic acids can be delivered as part of a larger construct, such as a plasmid or viral vector, or directly, e.g., by electroporation, lipid vesicles, viral transporters, microinjection, and biolistics. For example, the sequence-specific nuclease (and exonuclease described herein) can be introduced into the cell by a variety of means known in the art, including transfection, calcium phosphate-DNA co-precipitation, DEAE-dextran-mediated transfection, polybrene-mediated transfection, electroporation, microinjection, transduction, cell fusion, liposome fusion, lipofection, protoplast fusion, retroviral infection, use of a gene gun, use of a DNA vector transporter, and biolistics (e.g., particle bombardment) (See e.g., Wu et al., 1992, J. Biol. Chem., 267:963-967; Wu and Wu, 1988, J. Biol. Chem., 263:14621-14624; and Williams et al., 1991, Proc. Natl. Acad. Sci. USA 88:2726-2730). Receptor-mediated DNA delivery approaches can also be used (Curiel et al., 1992, Hum. Gene Ther., 3:147-154; and Wu and Wu, 1987, J. Biol. Chem., 262:4429-4432).

The donor construct can be introduced into the cell in the form of a linear nucleic acid or cleaved within the cell to produce a linear nucleic acid. It can be delivered by any method appropriate for introducing nucleic acids into a cell.

For example, the donor construct can be introduced into the cell by a variety of means known in the art, including transfection, calcium phosphate-DNA co-precipitation, DEAE-dextran-mediated transfection, polybrene-mediated transfection, electroporation, microinjection, transduction, cell fusion, liposome fusion, lipofection, protoplast fusion, retroviral infection, use of a gene gun, use of a DNA vector transporter, and biolistics (e.g., particle bombardment) (See e.g., Wu et al., 1992, J. Biol. Chem., 267:963-967; Wu and Wu, 1988, J. Biol. Chem., 263:14621-14624; and Williams et al., 1991, Proc. Natl. Acad. Sci. USA 88:2726-2730). Receptor-mediated DNA delivery approaches can also be used (Curiel et al., 1992, Hum. Gene Ther., 3:147-154; and Wu and Wu, 1987, J. Biol. Chem., 262:4429-4432).

In one embodiment, a target cell can be transfected with a nucleic acid containing a specific gene that leads to the expression of a gene product in the target cell, for example, a sequence-specific nuclease or exonuclease described herein. In another embodiment, a functional protein, e.g., a sequence-specific nuclease or exonuclease, is delivered into a target cell, using membrane-disrupting, pore-forming methods or reagents, such as micro-injection and electroporation, or other reagents such as liposomes as a carrier to deliver the protein across the cell membrane. Using a variety of assays known in the art, introduction of nucleic acids or proteins in the target cell can be confirmed and their effects on cellular physiology and/or gene expression can be studied.

In some aspects, delivery of the sequence-specific nuclease, donor construct, and/or exonuclease described herein into a target cell is nonspecific, e.g., anything can enter or exit the cell once the membrane is disrupted. In other aspects, the delivery of nucleic acids and/or proteins into a target cell is specific. For example, the sequence-specific nuclease, donor construct, and/or exonuclease described herein can be delivered into a cell using protein-transduction domains (PTDs) and/or membrane-translocating peptides that mediate protein delivery into cells. These PTDs or signal peptide sequences are naturally occurring polypeptides of 15 to 30 amino acids, which normally mediate protein secretion in the cells. They are composed of a positively charged amino terminus, a central hydrophobic core and a carboxyl-terminal cleavage site recognized by a signal peptidase. In certain embodiments, polypeptides, protein domains, and full-length protein, including antibodies, can be introduced into cells using solution-based protein transfection protocols. In one aspect, the protein to be introduced into cells is pre-complexed with a carrier reagent. In another embodiment, a fusion protein between the protein to be introduced and another moiety is used. For example, the fusion protein contains a protein (e.g., a sequence-specific nuclease and/or exonuclease) or a protein domain of interest, fused covalently with a protein or peptide that exhibits properties for spontaneous intracellular penetration. Examples of such membrane-transducing peptides include Trojan peptides, human immunodeficiency virus (HIV)-1 transcriptional activator (TAT) protein or its functional domain peptides, and other peptides containing protein-transduction domains (PTDs) derived from translocation proteins such as *Drosophila* homeotic transcription factor Antennapedia (Antp) and herpes simplex virus DNA-binding protein, VP22, and the like. Some commercially available peptides, for example, penetratin 1, Pep-1 (Chariot reagent, Active Motif Inc., Calif.) and HIV GP41 fragment (519-541), can be used.

In some embodiments, the exonuclease described herein is an alkaline exonuclease. In some embodiments, the exonuclease is a pH dependent alkaline exonuclease. In some embodiments, the exonuclease interacts with single-strand DNA binding protein and promotes strand exchange. In some embodiments, the exonuclease is also an endonuclease. In some embodiments, the exonuclease is a 5' to 3' exonuclease. In some embodiments, the exonuclease is a herpes simplex virus-type 1 (HSV-1) exonuclease. In some embodiments, the exonuclease is UL-12, e.g., UL-12 protein (SEQ ID NO: 2, accession number NP_044613.1) encoded by SEQ ID NO: 1 (accession number NC_001806.1, Gene ID: 2703382) as described in U.S. Pat. No. 7,135,324 B2, the disclosure of which is incorporated herein in its entirety for all purposes. In some embodiments, the exonuclease is a UL-12 homolog from Epstaine-Barr virus, bovine herpesvirus type 1, pseudoorabies virus, and human cytomegalovirus (HCMV).

In herpes simplex virus, the HSV-1 alkaline nuclease UL-12 and the HSV-1 single-strand DNA binding polypeptide (encoded by the ICP 8 gene and hereinafter referred to as "ICP8"; also known in the art as UL-29) work together to effect DNA strand exchange. As used herein, UL-12 refers to HSV-1 UL-12 as well as its homologs, orthologs, and paralogs. "Homolog" is a generic term used in the art to indicate a polynucleotide or polypeptide sequence possessing a high degree of sequence relatedness to a subject sequence. Such relatedness may be quantified by determining the degree of identity and/or similarity between the sequences being compared. Falling within this generic term are the terms "ortholog", meaning a polynucleotide or polypeptide that is the functional equivalent of a polynucleotide or polypeptide in another species, and "paralog" meaning a functionally similar sequence when considered within the same species. Paralogs present in the same species or orthologs of the UL-12 gene in other species can readily be identified without undue experimentation, by molecular biological techniques well known in the art.

Goldstein and Weller (1998, Virology, 244(2):442-57) examined the regions of HSV-1 UL-12 that are highly conserved among herpesvirus homologs and identified seven conserved amino acids regions. The seven regions of homology among herpesviruses were originally reported in Martinez et al., 1996, Virology, 215:152-64. Baculoviruses also encode a homolog of this protein (Ahrens et al., 1997, Virology, 229(2):381-99; Ayres et al., 1994, 202:586-605); however, only motifs I-IV are present in these homologs.

The seven conserved motifs of HSV-1 UL-12 are as follows: Motif I (from amino acid residue 218 to residue 244 of SEQ ID NO: 2), Motif II (from amino acid residue 325 to residue 340 of SEQ ID NO: 2), Motif III (from amino acid residue 362 to residue 377 of SEQ ID NO: 2), Motif IV (from amino acid residue 415 to residue 445 of SEQ ID NO: 2), Motif V (from amino acid residue 455 to residue 465 of SEQ ID NO: 2), Motif VI (from amino acid residue 491 to residue 514 of SEQ ID NO: 2), and Motif VII (from amino acid residue 565 to residue 576 of SEQ ID NO: 2). See Goldstein and Weller, 1998, Virology, 244(2):442-57, the disclosure of which is incorporated herein in its entirety for all purposes. Motif II is one of the most highly conserved regions. Within this motif, the C-terminal 5 amino acids (336-GASLD-340) represent the most conserved cluster. Asp340 is an absolutely conserved amino acid, and aspartic acid residues are required for metal binding in some endo- and exonucleases (Kovall and Matthews, 1997, Science, 277:1824-7). Within Motif II, Gly336 and Ser338 are absolutely conserved among 16 herpesvirus homologs. Goldstein and Weller demonstrated that the D340E mutant and G336A/S338A mutant of UL-12 lack exonuclease activity and therefore lack in vivo function.

In some embodiments, the exonuclease has a sequence that is at least about any of 70%, 80%, 90%, 95%, 98%, or 99% homologous to SEQ ID NO: 1. In some embodiments, the exonuclease comprises at least 1 (such as any of 2, 3, 4, 5, 6, or 7) conserved motif of UL12.

In some embodiments, the exonuclease is of eukaryotic or viral origin. In some aspects, the exonuclease is EXOI (eukaryotic) or exo (phage). In other embodiments, exonucleases such as ExoIII or bacteriophage T7 gene 6 exonuclease are used. In some embodiments, the exonuclease is Mre11, MRE11A, or MRE11B, for example of human origin.

Concomitant with, or sequential to, introduction of the exonuclease and/or donor construct, a sequence-specific nuclease is introduced into the cell. The term "sequence-specific endonuclease" or "sequence-specific nuclease," as used herein, refers to a protein that recognizes and binds to a polynucleotide at a specific nucleic acid sequence and catalyzes a single- or double-strand break in the polynucleotide. In certain embodiments, the sequence-specific nuclease cleaves the chromosome only once, i.e., a single double-strand break is introduced at the insertion site during the methods described herein.

Examples of sequence-specific nucleases include zinc finger nucleases (ZFNs). ZFNs are recombinant proteins composed of DNA-binding zinc finger protein domains and effector nuclease domains. Zinc finger protein domains are ubiquitous protein domains, e.g., associated with transcription factors, that recognize and bind to specific DNA sequences. One of the "finger" domains can be composed of about thirty amino acids that include invariant histidine residues in complex with zinc. While over 10,000 zinc finger sequences have been identified thus far, the repertoire of zinc finger proteins has been further expanded by targeted amino acid substitutions in the zinc finger domains to create new zinc finger proteins designed to recognize a specific nucleotide sequence of interest. For example, phage display libraries have been used to screen zinc finger combinatorial libraries for desired sequence specificity (Rebar et al., Science 263:671-673 (1994); Jameson et al, Biochemistry 33:5689-5695 (1994); Choo et al., PNAS 91: 11163-11167 (1994), each of which is incorporated herein as if set forth in its entirety). Zinc finger proteins with the desired sequence specificity can then be linked to an effector nuclease domain, e.g., as described in U.S. Pat. No. 6,824,978, such as FokI, described in PCT Application Publication Nos. WO1995/09233 and WO1994018313, each of which is incorporated herein by reference as if set forth in its entirety.

Another example of sequence-specific nucleases includes transcription activator-like effector endonucleases (TALEN), which comprise a TAL effector domain that binds to a specific nucleotide sequence and an endonuclease domain that catalyzes a double-strand break at the target site. Examples of TALENs and methods of making and using are described by PCT Patent Application Publication Nos. WO2011072246 and WO 2013163628, and U.S. Application Publication No. US 20140073015 A1, incorporated herein by reference as if set forth in their entireties.

In one aspect, a transcription activator-like effector (TALE) modulates host gene functions by binding specific sequences within gene promoters. "Transcription activator-like effector nucleases" or "TALENs" as used interchangeably herein refers to engineered fusion proteins of the catalytic domain of a nuclease, such as endonuclease Fok1, and a designed TALE DNA-binding domain that may be targeted to a custom DNA sequence. A "TALEN monomer" refers to an engineered fusion protein with a catalytic nuclease domain and a designed TALE DNA-binding domain. Two TALEN monomers may be designed to target and cleave a target region. In general, TALEs include tandem-like and nearly identical monomers (i.e., repeat domains), flanked by N-terminal and C-terminal sequences. In some embodiments, each monomer contains 34 amino acids, and the sequence of each monomer is highly conserved. Only two amino acids per repeat (i.e., residues 12th and 13th) are hypervariable, and are also known as repeat variable di-residues (RVDs). The RVDs determine the nucleotide-binding specificity of each TALE repeat domain. RVDs or RVD modules typically include 33-35 amino acids, of the TALE DNA-binding domain. RVD modules may be combined to produce an RVD array. The "RVD array length" as used herein refers to the number of RVD modules that corresponds to the length of the nucleotide sequence within the target region that is recognized by the TALEN, i.e., the binding region.

TALENs may be used to introduce site-specific double-strand breaks at targeted genomic loci. Site-specific double-strand breaks are created when two independent TALENs bind to nearby DNA sequences, thereby permitting dimerization of Fok1 and cleavage of the target DNA. TALENs have advanced genome editing due to their high rate of successful and efficient genetic modification. This DNA cleavage may stimulate the natural DNA-repair machinery, leading to one of two possible repair pathways: homology-directed repair (HDR) or the non-homologous end joining (NHEJ) pathway. The TALENs may be designed to target any gene, including genes involved in a genetic disease. The TALENs may include a nuclease and a TALE DNA-binding domain that binds to the target gene. The target gene may have a mutation such as a frameshift mutation or a nonsense mutation. If the target gene has a mutation that causes a premature stop codon, the TALEN may be designed to recognize and bind a nucleotide sequence upstream or downstream from the premature stop codon. In some embodiments, the TALE DNA-binding domain may have an RVD array length between 1-30 modules, between 1-25 modules, between 1-20 modules, between 1-15 modules, between 5-30 modules, between 5-25 modules, between 5-20 modules, between 5-15 modules, between 7-25 modules, between 7-23 modules, between 7-20 modules, between 10-30 modules, between 10-25 modules, between 10-20 modules, between 10-15 modules, between 15-30 modules, between 15-25 modules, between 15-20 modules, between 15-19 modules, between 16-26 modules, between 16-41 modules, between 20-30 modules, or between 20-25 modules in length. The RVD array length may be about any of 5 modules, 8 modules, 10 modules, 11 modules, 12 modules, 13 modules, 14 modules, 15 modules, 16 modules, 17 modules, 18 modules, 19 modules, 20 modules, 22 modules, 25 modules or 30 modules.

Another example of a sequence-specific nuclease system that can be used with the methods and compositions described herein includes the Cas/CRISPR system (Wiedenheft, B. et al. Nature 482, 331-338 (2012); Jinek, M. et al. Science 337, 816-821 (2012); Mali, P. et al. Science 339, 823-826 (2013); Cong, L. et al. Science 339, 819-823 (2013)). The Cas/CRISPR (Clustered Regularly interspaced Short Palindromic Repeats) system exploits RNA-guided DNA-binding and sequence-specific cleavage of target DNA. A guide RNA (gRNA) contains about 20-25 (such as 20) nucleotides that are complementary to a target genomic DNA sequence upstream of a genomic PAM (protospacer adjacent motifs) site and a constant RNA scaffold region. In certain embodiments, the target sequence is associated with a PAM, which is a short sequence recognized by the CRISPR complex. The precise sequence and length requirements for the PAM differ depending on the CRISPR enzyme used, but PAMs are typically 2-5 bp sequences adjacent to the protospacer (that is, the target sequence). Examples of PAM sequences are known in the art, and the skilled person will be able to identify further PAM sequences for use with a given CRISPR enzyme. For example, target sites for Cas9 from S. pyogenes, with PAM sequences NGG, may be identified by searching for 5'-$N_x$-NGG-3' both on an input sequence and on the reverse-complement of the input. In certain embodiments, the genomic PAM site used herein is NGG, NNG, NAG, NGGNG, or NNAGAAW. Other PAM sequences and methods for identifying PAM sequences are known in the art, for example, as disclosed in U.S. Pat. No. 8,697,359, the disclosure of which is incorporated herein by reference for all purposes. In particular embodiments, the Streptococcus pyogenes Cas9 (SpCas9) is used and the corresponding PAM is NGG. In some aspects, different Cas9 enzymes from different bacterial strains use different PAM sequences. The Cas (CRISPR-associated) protein binds to the gRNA and the target DNA to which the gRNA binds and introduces a double-strand break in a defined location upstream of the PAM site. In one aspect, the CRISPR/Cas, Cas/CRISPR, or the CRISPR-Cas system (these terms are used interchangeably throughout this application) does not require the generation of customized proteins to target specific sequences but rather a single Cas enzyme can be programmed by a short RNA molecule to recognize a specific DNA target, i.e., the Cas enzyme can be recruited to a specific DNA target using the short RNA molecule.

In some embodiments, the sequence-specific nuclease is a type II Cas protein. In some embodiments, the sequence-specific nuclease is Cas9 (also known as Csn1 and Csx12), a homolog thereof, or a modified version thereof. In some embodiments, a combination of two or more Cas proteins can be used. In some embodiments the CRISPR enzyme is Cas9, and may be Cas9 from S. pyogenes or S. pneumoniae. The Cas enzymes are known in the art; for example, the amino acid sequence of S. pyogenes Cas9 protein may be found in the SwissProt database under accession number Q99ZW2.

In some embodiments, Cas9 is used in the methods described herein. Cas9 harbors two independent nuclease domains homologous to HNH and RuvC endonucleases, and by mutating either of the two domains, the Cas9 protein can be converted to a nickase that introduces single-strand breaks (Cong, L. et al. Science 339, 819-823 (2013)). It is specifically contemplated that the inventive methods and compositions can be used with the single- or double-strand-inducing version of Cas9, as well as with other RNA-guided DNA nucleases, such as other bacterial Cas9-like systems. The sequence-specific nuclease of the methods and compositions described herein can be engineered, chimeric, or isolated from an organism.

CRISPRs, also known as SPMRs (SPacer Interspersed Direct Repeats), constitute a family of DNA loci that are usually specific to a particular bacterial species. The CRISPR locus comprises a distinct class of interspersed short sequence repeats (SSRs) that are recognized in E. coli (Ishino et al., 1987, J. Bacteriol., 1.69:5429-5433; and Nakata et al., 1989, J. Bacteriol., 171:3553-3556), and associated genes. Similar interspersed SSRs have been identified in Haloferax mediterranei, Streptococcus pyogenes, Anabaena, and Mycobacterium tuberculosis (See, Groenen et al., 1993, Mol. Microbiol., 10:1057-1065; Hoe et al., 1999, Emerg. Infect. Dis., 5:254-263; Masepohl et al., 1996, Biochim. Biophys. Acta 1307:26-30; and Mojica et al., 1995, Mol. Microbiol., 17:85-93). The CRISPR loci typically differ from other SSRs by the structure of the repeats, which have been termed short regularly spaced repeats (SRSRs) (Janssen et al., 2002, OMICS J. Integ. Biol., 6:23-33; and Mojica et al., 2000, Mol. Microbiol., 36:244-246). In general, the repeats are short elements that occur in clusters that are regularly spaced by unique intervening sequences with a substantially constant length (Mojica et al., 2000, supra). Although the repeat sequences are highly conserved between strains, the number of interspersed repeats and the sequences of the spacer regions typically differ from strain to strain (van Embden et al., 2000, J. Bacteriol., 182:2393-2401). CRISPR loci have been identified in more than 40 prokaryotes (See e.g., Jansen et al., 2002, Mol. Microbiol., 43:1565-1575) including, but not limited to Aeropyrum, Pyrobaculum, Sulfolobus, Archaeoglobus, Halocarcula, Methanobacteriumn, Methanococcus, Methanosarcina, Methanopyrus, Pyrococcus, Picrophilus, Thernioplasnia, Corynebacterium, Mycobacterium, Streptomyces, Aquifrx, Porphvromonas, Chlorobium, Thermos, Bacillus, Listeria, Staphylococcus, Clostridium, Thermoanaerobacter, Mycoplasma, Fusobacterium, Azarcus, Chromobacterium, Neisseria, Nitrosomonas, Desulfovibrio, Geobacter, Alvrococcus, Campylobacter, Wolinella, Acinetobacter, Erwinia, Escherichia, Legionella, Methylococcus, Pasteurella, Photobacterium, Salmonella, Xanthomonas, Yersinia, Treponema, and Thermotoga.

The CRISPR system refers collectively to transcripts and other elements involved in the expression of or directing the activity of Cas genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or other sequences and transcripts from a CRISPR locus. In some embodiments, one or more elements of a CRISPR system is derived from a type I, type II, or type III CRISPR system. In some embodiments, one or more elements of a CRISPR system can be derived from a particular organism comprising an endogenous CRISPR system, such as Streptococcus pyogenes. In certain embodiments, elements of a CRISPR system promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to have complementarity, where hybridization between a target sequence and a guide sequence promotes the formation of a CRISPR complex. Full complementarity is not necessarily required, provided there is sufficient complementarity to cause hybridization and promote formation of a CRISPR complex, A target sequence may comprise any polynucleotide, such as DNA or RNA polynucleotides. In some embodiments, a target sequence is located in the nucleus or cytoplasm of a cell. In some embodiments, the target sequence may be within an organelle of a eukaryotic cell, for example, mitochondrion or chloroplast. A sequence or template that may be used for recombination into the targeted locus comprising the target sequences is referred to as an "editing template" or "editing polynucleotide" or "editing sequence". In aspects of the present disclosure, an exogenous template polynucleotide may be referred to as an editing template. In some aspects, the recombination is homologous recombination. The CRISPR-Cas systems have been used for editing, regulating and targeting genomes, for example, as disclosed in Sander and Joung, 2014 Nature Biotechnology 32(4): 347-55, the disclosure of which is incorporated herein by reference for all purposes.

An exemplary type II CRISPR system is the type II CRISPR locus from *Streptococcus pyogenes* SF370, which contains a cluster of four genes Cas9, Cas1, Cas2, and Csn1, as well as two non-coding RNA elements, tracrRNA and a characteristic array of repetitive sequences (direct repeats) interspaced by short stretches of non-repetitive sequences (spacers, about 30 bp each). In this system, targeted DNA double-strand break (DSB) is generated in four sequential steps. First, two non-coding RNAs, the pre-crRNA array and tracrRNA, are transcribed from the CRISPR locus. Second, tracrRNA hybridizes to the direct repeats of pre-crRNA, which is then processed into mature crRNAs containing individual spacer sequences. Third, the mature crRNA: tracrRNA complex directs Cas9 to the DNA target consisting of the protospacer and the corresponding PAM via heteroduplex formation between the spacer region of the crRNA and the protospacer DNA. Finally, Cas9 mediates cleavage of target DNA upstream of PAM to create a DSB within the protospacer. Additional descriptions of CRISPR and/or Cas and methods of use can be found in WO 2007025097, US 20100093617, US 20130011828, U.S. Ser. No. 13/960,796, U.S. Pat. No. 8,546,553, WO 2010011961, US 20140093941, US 20100076057, US 20110217739, WO 2010075424, WO 2013142578, WO 2013141680, US 20130326645, WO 2013169802, US 20140068797, WO 2013176772, WO 2013181440, US 20130330778, WO 2013188037, WO 2013188522, WO 2013188638, WO 2013192278, WO 2014018423, CN 103388006, WO 2014022702, US 20140090113, WO 2014039872, WO 2014065596, U.S. Pat. No. 8,697,359, and CN 103725710, the disclosures of which are incorporated herein by reference in their entireties for all purposes.

In some embodiments, the sequence-specific nuclease is an RNA-guided endonuclease (for example for the Cas/CRIPSR) system. The term "RNA-guided DNA nuclease" or "RNA-guided DNA nuclease" or "RNA-guided endonuclease," as used herein, refers to a protein that recognizes and binds to a guide RNA and a polynucleotide, e.g., a target gene, at a specific nucleotide sequence and catalyzes a single- or double-strand break in the polynucleotide. In some embodiments, a guide RNA is an RNA comprising a 5' region comprising at least one repeat from a CRISPR locus and a 3' region that is complementary to the predetermined insertion site on the chromosome. In certain embodiments, the 5' region comprises a sequence that is complementary to the predetermined insertion site on the chromosome, and the 3' region comprises at least one repeat from a CRISPR locus. In some aspects, the 3' region of the guide RNA further comprises the one or more structural sequences of crRNA and/or trRNA. The 5' region can comprise, for example, about 1, 2, 3, 4, 5, or more repeats from a CRISPR locus, and can be about any of 5, 10, 15, 20, 25, 30, or more nucleotides long. In some embodiments, the 5' region sequence that is complementary to the predetermined insertion site on the chromosome comprises between about 17 and about 24 nucleotides. In other embodiments, the 3' region can be, for example, about any of 5, 10, 15, 20, 25, 30, or more nucleotides long. In some aspects, 5' region sequence that is complementary to the predetermined inser- tion site on the chromosome can vary in length, while the 3' region sequence is fixed in length. In such embodiments where guide RNA is needed, the introduction of the sequence-specific nuclease step may also comprise introduction of the guide RNA into the cell. The guide RNA can be introduced, for example, as RNA or as a plasmid or other nucleic acid vector encoding the guide RNA. The plasmid or other nucleic acid vector may further comprise coding sequence(s) for the sequence-specific nuclease (such as Cas) and/or the exonuclease (such as UL-12). In some embodiments, the guide RNA comprises a crRNA and a tracrRNA, and the two pieces of RNA form a complex through hybridization. In some embodiments when multiple guide RNAs are used, a single tracrRNA paired with different crRNAs can be used.

Thus, for example, in some embodiments, there is provided a method of inserting a donor sequence at a predetermined insertion site on a chromosome in an eukaryotic cell, the method comprising: a) introducing into the cell a sequence-specific RNA-guided nuclease (such as Cas, for example Cas9); b) introducing into the cell a guide RNA recognizing the insertion site; c) introducing into the cell a donor construct; and d) introducing into the cell a nucleic acid sequence encoding an exonuclease (such as UL-12); wherein the donor construct is a linear nucleic acid or cleaved within the cell to produce a linear nucleic acid, wherein the linear nucleic acid comprises a 5' homology arm, the donor sequence, and a 3' homology arm, wherein the 5' homology arm is homologous to a sequence upstream of the nuclease cleavage site on the chromosome and wherein the 3' homology arm is homologous to a sequence downstream of the nuclease cleavage site on the chromosome; wherein the 5' homology arm and the 3' homology arm are proximal to the 5' and 3' ends of the linear nucleic acid, respectively, and wherein the donor sequence is inserted into the chromosome at the insertion site through homologous recombination.

In some embodiments, there is provided a method of inserting a donor sequence at a predetermined insertion site on a chromosome in an eukaryotic cell, the method comprising: a) introducing into the cell a nucleic acid sequence encoding a sequence-specific RNA-guided nuclease (such as Cas, for example Cas9); b) introducing into the cell a nucleic acid sequence encoding a guide RNA recognizing the insertion site; c) introducing into the cell a donor construct; and d) introducing into the cell a nucleic acid sequence encoding an exonuclease (such as UL-12); wherein the donor construct is a linear nucleic acid or cleaved within the cell to produce a linear nucleic acid, wherein the linear nucleic acid comprises a 5' homology arm, the donor sequence, and a 3' homology arm, wherein the 5' homology arm is homologous to a sequence upstream of the nuclease cleavage site on the chromosome and wherein the 3' homology arm is homologous to a sequence downstream of the nuclease cleavage site on the chromosome; wherein the 5' homology arm and the 3' homology arm are proximal to the 5' and 3' ends of the linear nucleic acid, respectively, and wherein the donor sequence is inserted into the chromosome at the insertion site through homologous recombination.

In some embodiments, there is provided a method of inserting a donor sequence at a predetermined insertion site on a chromosome in an eukaryotic cell, the method comprising: a) introducing into the cell a vector comprising a nucleic acid sequence encoding a sequence-specific RNA-guided nuclease (such as Cas, for example Cas9); b) introducing into the cell a vector comprising a nucleic acid sequence encoding a guide RNA recognizing the insertion site; c) introducing into the cell a donor construct; and d) introducing into the cell a DNA vector comprising a nucleic acid sequence encoding an exonuclease (such as UL-12); wherein the donor construct is a linear nucleic acid or cleaved within the cell to produce a linear nucleic acid, wherein the linear nucleic acid comprises a 5' homology arm, the donor sequence, and a 3' homology arm, wherein the 5' homology arm is homologous to a sequence upstream of the nuclease cleavage site on the chromosome and wherein the 3' homology arm is homologous to a sequence downstream of the nuclease cleavage site on the chromosome; wherein the 5' homology arm and the 3' homology arm are proximal to the 5' and 3' ends of the linear nucleic acid, respectively, and wherein the donor sequence is inserted into the chromosome at the insertion site through homologous recombination.

In some embodiments, there is provided a method of inserting a donor sequence at a predetermined insertion site on a chromosome in an eukaryotic cell, the method comprising: a) introducing into the cell a vector comprising a nucleic acid sequence encoding a sequence-specific RNA-guided nuclease (such as Cas, for example Cas9) and a guide RNA recognizing the insertion site; b) introducing into the cell a donor construct; and c) introducing into the cell a DNA vector comprising a nucleic acid sequence encoding an exonuclease (such as UL-12); wherein the donor construct is a linear nucleic acid or cleaved within the cell to produce a linear nucleic acid, wherein the linear nucleic acid comprises a 5' homology arm, the donor sequence, and a 3' homology arm, wherein the 5' homology arm is homologous to a sequence upstream of the nuclease cleavage site on the chromosome and wherein the 3' homology arm is homologous to a sequence downstream of the nuclease cleavage site on the chromosome; wherein the 5' homology arm and the 3' homology arm are proximal to the 5' and 3' ends of the linear nucleic acid, respectively, and wherein the donor sequence is inserted into the chromosome at the insertion site through homologous recombination.

In some embodiments, there is provided a method of inserting a donor sequence at a predetermined insertion site on a chromosome in an eukaryotic cell, the method comprising: a) introducing into the cell a vector comprising a nucleic acid sequence encoding a sequence-specific RNA-guided nuclease (such as Cas, for example Cas9) and a nucleic acid sequence encoding an exonuclease (such as UL-12); b) introducing into the cell a guide RNA recognizing the insertion site; and c) introducing into the cell a donor construct; wherein the donor construct is a linear nucleic acid or cleaved within the cell to produce a linear nucleic acid, wherein the linear nucleic acid comprises a 5' homology arm, the donor sequence, and a 3' homology arm, wherein the 5' homology arm is homologous to a sequence upstream of the nuclease cleavage site on the chromosome and wherein the 3' homology arm is homologous to a sequence downstream of the nuclease cleavage site on the chromosome; wherein the 5' homology arm and the 3' homology arm are proximal to the 5' and 3' ends of the linear nucleic acid, respectively, and wherein the donor sequence is inserted into the chromosome at the insertion site through homologous recombination.

In some embodiments, there is provided a method of inserting a donor sequence at a predetermined insertion site on a chromosome in an eukaryotic cell, the method comprising: a) introducing into the cell a vector comprising a nucleic acid sequence encoding a sequence-specific nuclease (such as Cas, for example Cas9), a guide RNA recognizing the insertion site, and a nucleic acid sequence encoding an exonuclease (such as UL-12); b) introducing into the cell a donor construct; wherein the donor construct is a linear nucleic acid or cleaved within the cell to produce a linear nucleic acid, wherein the linear nucleic acid comprises a 5' homology arm, the donor sequence, and a 3' homology arm, wherein the 5' homology arm is homologous to a sequence upstream of the nuclease cleavage site on the chromosome and wherein the 3' homology arm is homologous to a sequence downstream of the nuclease cleavage site on the chromosome; wherein the 5' homology arm and the 3' homology arm are proximal to the 5' and 3' ends of the linear nucleic acid, respectively, and wherein the donor sequence is inserted into the chromosome at the insertion site through homologous recombination.

In some embodiments, there is provided a method of inserting a donor sequence at a predetermined insertion site on a chromosome in an eukaryotic cell (such as a zygotic cell), the method comprising: a) injecting into the cell an mRNA sequence encoding a sequence-specific nuclease (such as Cas, for example Cas9); b) injecting into the cell a guide RNA recognizing the insertion site; c) introducing (such as injecting) into the cell a donor construct; and d) injecting into the cell an mRNA sequence encoding an exonuclease; wherein the donor construct is a linear nucleic acid or cleaved within the cell to produce a linear nucleic acid, wherein the linear nucleic acid comprises a 5' homology arm, the donor sequence, and a 3' homology arm, wherein the 5' homology arm is homologous to a sequence upstream of the nuclease cleavage site on the chromosome and wherein the 3' homology arm is homologous to a sequence downstream of the nuclease cleavage site on the chromosome; wherein the 5' homology arm and the 3' homology arm are proximal to the 5' and 3' ends of the linear nucleic acid, respectively, and wherein the donor sequence is inserted into the chromosome at the insertion site through homologous recombination. In some embodiments, the injection is carried out in vitro. In some embodiments, the injection is carried out in vivo. In some embodiments, the method further comprises transcribing in vitro a nucleic acid encoding the sequence-specific RNA-guided nuclease into mRNA. In some embodiments, the method further comprises transcribing in vitro a nucleic acid encoding the guide RNA recognizing the insertion site into mRNA. In some embodiments, the method further comprises transcribing in vitro a nucleic acid encoding the exonuclease into mRNA.

The insertion of the donor sequence can be evaluated using any methods known in the art. For example, a 5' primer corresponding to a sequence upstream of the 5' homology arm and a corresponding 3' primer corresponding to a region in the donor sequence can be designed to assess the 5'-junction of the insertion. Similarly, a 3' primer corresponding to a sequence downstream of the 3' homology arm and a corresponding 5' primer corresponding to a region in the donor sequence can be designed to assess the 3'-junction of the insertion. Other methods such as southern blot and DNA sequencing technologies can also be used.

The insertion site can be at any desired site, so long as sequence-specific nuclease can be designed to effect cleavage at such site. In some embodiments, the insertion site is at a target gene locus. In some embodiments, the insertion site is not a gene locus.

"Donor sequence" as used herein refers to a nucleic acid to be inserted into the chromosome of a host cell. In some embodiments, the donor nucleic acid is a sequence not present in the host cell. In some embodiments, the donor sequence is an endogenous sequence present at a site other than the predetermined target site. In some embodiments, the donor sequence is a coding sequence. In some embodiments, the donor sequence is a non-coding sequence. In some embodiments, the donor sequence is a mutant locus of a gene.

The size of the donor sequence can range from about 1 bp to about 100 kb. In certain embodiments, the size of the donor sequence is between about 1 bp and about 10 bp, between about 10 bp and about 50 bp, between about 50 bp and about 100 bp, between about 100 bp and about 500 bp, between about 500 bp and about 1 kb, between about 1 kb and about 10 kb, between about 10 kb and about 50 kb, between about 50 kb and about 100 kb, or more than about 100 kb.

In some embodiments, the donor sequence is an exogenous gene to be inserted into the chromosome. In some embodiments, the donor sequence is modified sequence that replaces the endogenous sequence at the target site. For example, the donor sequence may be a gene harboring a desired mutation, and can be used to replace the endogenous gene present on the chromosome. In some embodiments, the donor sequence is a regulatory element. In some embodiments, the donor sequence is a tag or a coding sequence encoding a reporter protein and/or RNA. In some embodiments, the donor sequence is inserted in frame into the coding sequence of a target gene which will allow expression of a fusion protein comprising an exogenous sequence fused to the N- or C-terminus of the target protein.

The donor construct described herein is either a linear nucleic acid or cleaved within the cell to produce a linear nucleic acid. The linear nucleic acid described herein comprises a 5' homology arm, a donor sequence, and a 3' homology arm. The 5' and 3' homology arms are homologous to a sequence upstream and downstream of the DNA cleavage site on the target chromosome, thereby allowing homologous recombination to occur.

The term "homology" or "homologous" as used herein is defined as the percentage of nucleotide residues in the homology arm that are identical to the nucleotide residues in the corresponding sequence on the target chromosome, after aligning the sequences and introducing gaps, if necessary, to achieve the maximum percent sequence identity. Alignment for purposes of determining percent nucleotide sequence homology can be achieved in various ways that are within the skill in the art, for instance, using publicly available computer software such as BLAST, BLAST-2, ALIGN, ClustalW2 or Megalign (DNASTAR) software. Those skilled in the art can determine appropriate parameters for aligning sequences, including any algorithms needed to achieve maximal alignment over the full length of the sequences being compared. In some embodiments, the homology between the 5' homology arm and the corresponding sequence on the chromosome is at least about any of 80%, 85%, 90%, 95%, 98%, 99%, or 100%. In some embodiments, the homology between the 3' homology arm and the corresponding sequence on the chromosome is at least about any of 80%, 85%, 90%, 95%, 98%, 99%, or 100%.

In one embodiment, the homology arms are more than about 30 bp in length, for example more than about any of 50 bp, 100 bp, 200 bp, 300 bp, 500 bp, 800 bp, 1 kb, 1.5 kb, 2 kb and 5 kb in length. The 5' and/or 3' homology arms can be homologous to a sequence immediately upstream and/or downstream of the DNA cleavage site. Alternatively, the 5' and/or 3' homology arms can be homologous to a sequence that is distant from the DNA cleavage site, for example a sequence that is 0 bp away from the DNA cleavage site, or partially or completely overlaps with the DNA cleavage site.

In other embodiments, the 5' and/or 3' homology arms can be homologous to a sequence that is at least about 1, 2, 5, 10, 15, 20, 25, 30, 50, 100, 200, 300, 400, or 500 bp away from the DNA cleavage site.

The 5' and 3' homology arms of the linear nucleic acid are each proximal to the 5' and 3' ends of the linear nucleic acid, respectively, i.e., no more than about 200 bp away from the 5' and 3' ends of the linear nucleic acid. In some embodiments, the 5' homology arm is no more than about any of 1, 2, 5, 10, 15, 20, 25, 30, 35, 40, 45, 50, 55, 60, 70, 80, 90, 100, 120, 140, 160, 180, or 200 bp away from the 5' end of the linear DNA. In some embodiments, the 3' homology arm is no more than about any of 1, 2, 5, 10, 15, 20, 25, 30, 35, 40, 45, 50, 55, 60, 70, 80, 90, 100, 120, 140, 160, 180, or 200 bp away from the 3' end of the linear DNA. In some aspects, the 5' and/or 3' homology arms can be immediately linked to the 5' and 3' ends of the linear DNA, respectively, or partially or completely overlap with the 5' and 3' ends of the linear DNA, respectively.

In some embodiments, the donor construct is cleaved within the cell (for example by a sequence-specific nuclease recognizing a cleavage site on the construct) to produce a linear nucleic acid described herein. For example, the donor construct may comprise flanking sequences upstream of the 5' homology arm and downstream of the 3' homology arm. Such flanking sequences in some embodiments do not exist in the genomic sequences of the host cell thus allowing cleavage to only occur on the donor construct. Sequence-specific nucleases can then be designed accordingly to effect cleavage at the flanking sequences that allows the release of the linear nucleic acid without affecting the host sequences. The flanking sequences can be, for example, about 5 to about 500 bp, including about any of 5-15, 15-30, 30-50, 50-80, 80-100, 100-150, 150-200, 200-300, 300-400, or 400-500 bp. In some embodiments, the flanking sequence is no more than about any of 10, 20, 30, 40, 50, 60, 70, 80, 90, or 100 bp. In some embodiments, the portion of the flanking sequence remaining on the linear nucleic acid after sequence-specific cleavage is about any of 10, 20, 30, 40, 50, 60, 70, 80, 90, or 100 bp. In some embodiments, the flanking sequence comprises any one of the following sequences:

```
                                        (SEQ ID NO: 3)
GGCAGAAATGGCTCCGATCGAGG (SEQ ID NO: 4)
GGGCGGGATTGATAGCGCGCGGG (SEQ ID NO: 5)
GGCAGTCGGGAACATCTCGTGGG (SEQ ID NO: 6)
GGGCGCAGTAATTCTTAGAGCGG (SEQ ID NO: 7)
GGCTAATAACTTAATCGTGGAGG (SEQ ID NO: 8)
GGTTAAGCCTTATTGGTGGTCGG (SEQ ID NO: 9)
GGAGGCCTGCTTGCAAGCATTGG (SEQ ID NO: 10)
GGTTAGGCCCTAAGCGAATACGG (SEQ ID NO: 11)
GGAGCCGAGTTGACGGTTAGCGG
```

GGGGTTCCTTCACGAGCGTCCGG (SEQ ID NO: 12)

GGTACAATGTAACGTTGCGCGGG (SEQ ID NO: 13)

GGTATTCAAGTCACTAATGTCGG (SEQ ID NO: 14)

GGAACCCCTTCCGTTCCGTCGGG (SEQ ID NO: 15)

GGTATTCACTCCTAAAGCGTCGG (SEQ ID NO: 16)

GGGATGGAACACTAGACTGCGGG (SEQ ID NO: 17)

GGTTAATCCCTCATGACCGTCGG (SEQ ID NO: 18)

GGAGCTTCAGTGTCGGTCGTTGG (SEQ ID NO: 19)

GGTTACGTGCCATATACGTTCGG (SEQ ID NO: 20)

In some embodiments, the donor construct is a circular DNA construct. The donor construct can further include certain sequences that provide structural or functional support, such as sequences of a plasmid or other vector that supports propagation of the donor construct (e.g., pUC19 vector). The donor construct can optionally also include certain selectable markers or reporters, some of which may be flanked by recombinase recognition sites for subsequent activation, inactivation, or deletion.

In some embodiments when the donor construct is cleaved within the cell to produce a linear nucleic acid, the methods described herein may further comprise introducing into the cell a second sequence-specific nuclease into the cell. The second sequence-specific nuclease recognizes cleavage sites (such as flanking sequences described herein) on the construct and lead to cleavage of the donor construct within the cell, producing a linear nucleic acid.

Thus, in some embodiments there is provided a method of inserting a donor sequence at a predetermined insertion site on a chromosome of an eukaryotic cell, comprising: a) introducing into the cell a first sequence-specific nuclease that cleaves the chromosome at the insertion site; b) introducing into the cell a donor construct (such as a circular donor construct), c) introducing into the cell a second sequence-specific nuclease that cleaves the donor construct; and d) introducing into the cell an exonuclease; wherein upon cleavage by the second sequence-specific nuclease the donor construct produces a linear nucleic acid comprising a 5' homology arm, the donor sequence, and a 3' homology arm, wherein the 5' homology arm is homologous to a sequence upstream of the nuclease cleavage site on the chromosome and wherein the 3' homology arm is homologous to a sequence downstream of the nuclease cleavage site on the chromosome; and wherein the 5' homology arm and the 3' homology arm are proximal to the 5' and 3' ends of the linear nucleic acid, respectively, and wherein the donor sequence is inserted into the chromosome at the insertion site through homologous recombination. In some embodiments, the first sequence-specific nuclease and the second sequence-specific nuclease are of the same kind (for example, both are ZFN, TALEN, or CRISPR-based nucleases). In some embodiments, the first sequence-specific nuclease and the second sequence-specific nuclease are of different kinds. In some embodiments, the first sequence-specific nuclease, the second sequence-specific nuclease, and/or the exonuclease are introduced into the cell simultaneously. In some embodiments, the first sequence-specific nuclease, the second sequence-specific nuclease, and/or the exonuclease are introduced into the cell sequentially. In some embodiments, the first sequence-specific nuclease, the second sequence-specific nuclease, and/or the exonuclease are introduced into the cell as a cDNA. In some embodiments, the first sequence-specific nuclease, the second sequence-specific nuclease, and/or the exonuclease are introduced into the cell as an mRNA. In some embodiments, the first sequence-specific nuclease, the second sequence-specific nuclease, and/or the exonuclease are introduced into the cell as a protein.

In some embodiments, the first sequence-specific nuclease and the second sequence-specific nuclease are both sequence-specific RNA-guided nucleases. In such embodiments, a single nuclease together with two different guide RNAs (one recognizing the insertion site, another recognizing the cleavage site on the donor construct) can be used. For example, in some embodiments, the method comprises: a) introducing into the cell a sequence-specific RNA-guided nuclease; b) introducing into the cell a donor construct (such as a circular donor construct); c) introducing into the cell a first guide RNA recognizing the insertion site; d) introducing into the cell a second guide RNA recognizing a cleavage site on the donor construct; and e) introducing into the cell an exonuclease; wherein upon cleavage by the sequence-specific nuclease the donor construct produces a linear nucleic acid comprising a 5' homology arm, the donor sequence, and a 3' homology arm, wherein the 5' homology arm is homologous to a sequence upstream of the nuclease cleavage site on the chromosome and wherein the 3' homology arm is homologous to a sequence downstream of the nuclease cleavage site on the chromosome; and wherein the 5' homology arm and the 3' homology arm are proximal to the 5' and 3' ends of the linear nucleic acid, respectively, and wherein the donor sequence is inserted into the chromosome at the insertion site through homologous recombination. In some embodiments, the first guide RNA and the second guide RNA are introduced into the cell via a DNA vector (and in some embodiments on the same vector). In some embodiments, the first guide RNA and the second guide RNA are introduced into the cells by injection (for example after being produced by in vitro transcription).

The present application therefore also provides methods of producing a linear nucleic acid described herein. In some embodiments, there is provided a method of producing a linear nucleic acid in an eukaryotic cell, wherein the linear nucleic acid comprises a 5' homology arm, the donor sequence, and a 3' homology arm, wherein the 5' homology arm is homologous to a sequence upstream of the nuclease cleavage site on the chromosome and wherein the 3' homology arm is homologous to a sequence downstream of the nuclease cleavage site on the chromosome; and wherein the 5' homology arm and the 3' homology arm are proximal to the 5' and 3' ends of the linear nucleic acid, respectively, comprising: a) introducing into the cell a circulated donor construct comprising the linear nucleic acid and further comprising a 5' flanking sequence upstream of the 5' homology arm and a 3' flanking sequence downstream of the 3' homology arm; and b) introducing into the cell a sequence-specific nuclease, wherein the sequence-specific nuclease cleaves the circular nucleic acid construct at the flanking sequences thereby producing the linear nucleic acid. In some embodiments, the cleavage site is at the 5' flanking sequence and/or 3' flanking sequence. In some embodiments, the linear DNA is about 200 bp to about 100 kb long. In certain embodiments, the linear DNA is between about 10 bp and about 50 bp, between about 50 bp and about 100 bp, between about 100 bp and about 150 bp, between about 150 bp and about 200 bp, between about 200 bp and about 500 bp, between about 500 bp and about 1 kb, between about 1 kb and about 10 kb, between about 10 kb and about 50 kb, between about 50 kb and about 100 kb, or more than about 100 kb in length.

Uses of the Present Methods

The methods described herein can find many uses. For example, the methods described herein can be useful for generating gene-modified cells (such as immune cells), which can be useful for cellular therapeutics.

In some embodiments, there is provided a method of generating a genetically modified animal (for example a genetically modified rodent such as mouse or rat) comprising a donor sequence inserted at a predetermined insertion site on the chromosome of the animal, comprising: a) introducing into a cell of the animal a sequence-specific nuclease that cleaves the chromosome at the insertion site; b) introducing into the cell a donor construct; c) introducing into the cell an exonuclease; wherein the donor construct is a linear nucleic acid or cleaved within the cell to produce a linear nucleic acid; and d) introducing the cell into a carrier animal to produce the genetically modified animal, wherein the donor construct is a linear nucleic acid or cleaved within the cell to produce a linear nucleic acid, wherein the linear nucleic acid comprises a 5' homology arm, the donor sequence, and a 3' homology arm, wherein the 5' homology arm is homologous to a sequence upstream of the nuclease cleavage site on the chromosome and wherein the 3' homology arm is homologous to a sequence downstream of the nuclease cleavage site on the chromosome; wherein the 5' homology arm and the 3' homology arm are proximal to the 5' and 3' ends of the linear nucleic acid, respectively, and wherein the donor sequence is inserted into the chromosome at the insertion site through homologous recombination. In some embodiments, the cell is an embryotic stem cell. In some embodiments, the cell is a zygotic cell. In some embodiments, the method further comprises breeding the genetically modified animal.

In some embodiments, the cells are cells from a blastocyst. Upon injection of the various components into the cells, chimeric animals can be developed from the injected blastocysts. The heterozygous F1 animals can be obtained by breeding between the chimera and the pure inbred animal. The homozygous animals can be obtained by intercross between the heterozygous animals In some embodiments, the method is used to generate a mutant animal having a specific mutant allele. For example, the donor sequence may contain a mutant allele, and can be inserted into the genome of the animal (for example by replacing the corresponding endogenous locus). The mutant animals can be useful for many purposes, for example serving as a research tool or a disease model. In some embodiments, the animal is modified to have a desired phenotype, such as a desired disease phenotype. Animals with various disease phenotypes that can be generated by methods described herein include, but are not limited to, animals exhibiting a phenotype in metabolic diseases, immunological diseases, neurological diseases, neurodegenerative diseases (such as Alzheimer's disease), embryonic development diseases, vascular diseases, inflammatory diseases (such as asthma and arthritis), infectious diseases, cancer, behavioral diseases, and cognitive diseases.

In some embodiments, the method described herein is used to generate a "humanized" animal, such as a humanized mouse or a humanized rat. A "humanized animal" used herein refers to an animal harboring a donor sequence of human origin. The human donor sequence can be inserted at any site on the genome. In some embodiments, the human donor sequence is inserted at the corresponding endogenous locus in the animal cell.

In some embodiments, a humanized rodent capable of producing immunoglobulin comprising a human variable domain and/or human constant domain can be generated. A rearranged or unrearranged human immunoglobulin locus containing the human immunoglobulin V, D, J and/or constant loci can be placed on the donor construct described herein and introduced into the genome of the animal cell by homologous recombination. The human immunoglobulin in some embodiments is inserted at the corresponding endogenous immunoglobulin locus in the animal cell. Through such manipulation transgenic animals capable of producing fully human antibodies, chimeric antibodies (e.g., antibodies comprising mouse variable domains and human constant domains), or reverse chimeric antibodies (e.g., antibodies comprising human variable domains and mouse constant regions), can be generated.

In some embodiments, the method described herein is used to generate a mouse model for a human disease or condition. In certain aspects, the mouse model reflects or mimics at least one aspect of the human disease or condition. In other aspects, the compositions and methods disclosed herein are used to knock-in a human gene into the mouse and replace the corresponding mouse gene, in order to generate humanized mice such as mice with humanized TNF-alpha (TNF-alpha H-mice), and mice with humanized IL-6 (IL-6 H-mice). Generation of mouse models of human diseases or conditions are disclosed in Wu et al., "Correction of a Genetic Disease in Mouse via Use of CRISPR-Cas9," *Cell Stem Cell* (2013) 13(6): 659-62, and in Yang et al., "One-Step Generation of Mice Carrying Reporter and Conditional Alleles by CRISPR/Cas-Mediated Genome Engineering," *Cell* (2013) 154(6): 1370-9, the disclosures of which are incorporated herein by reference in their entireties for all purposes.

In some embodiments, a transgenic animal having an immune cytokine reporter can be produced by inserting a sequence encoding the immune cytokine reporter at a desired insertion site on the chromosome of the animal cell through the donor constructs described herein.

In some embodiments, a transgenic mouse harboring an ROSA26 locus can be generated by inserting a sequence comprising the ROSA26 locus at a desired insertion site on the chromosome of the animal cell through the donor constructs described herein.

Also provided are cells and genetically modified animals produced by any one of the methods described herein.

Kits

Also provided herein are kits useful for any one of the methods described herein. For example, in some embodiments, there is provided a kit for inserting a donor sequence at an insertion site on a chromosome in an eukaryotic cell, comprising: a) a sequence-specific nuclease that cleaves the chromosome at the insertion site; b) a donor construct, wherein the donor construct comprises a 5' homology arm, the donor sequence, and a 3' homology arm, wherein the 5' homology arm is homologous to a sequence 5' to the insertion site on the chromosome and wherein the 3' homology arm is homologous to a sequence 3' to the insertion site on the chromosome; and c) an exonuclease, wherein the donor construct is a linear nucleic acid or can be cleaved to produce a linear nucleic acid, and wherein the 5' homology arm and the 3' homology arm are proximal to the 5' and 3' ends of the linear nucleic acid.

The kits described herein may also comprise a packaging to house the contents of the kit. The packaging optionally provides a sterile, contaminant-free environment, and can be made of any of plastic, paper, foil, glass, and the like. In some embodiments, the packaging is a glass vial. In some embodiments, the kit further comprises an instruction for carrying out any one of the methods described herein.

EXAMPLES

The following non-limiting examples further illustrate the compositions and methods of the present invention. Those skilled in the art will recognize that several embodiments are possible within the scope and spirit of this invention. The invention will now be described in greater detail by reference to the following non-limiting examples. The following examples further illustrate the invention but, of course, should not be construed as in any way limiting its scope.

Example 1. The EKI System Significantly Increases Knock-in Efficiency of EGFP-ACTB in U2OS Cells A targeting scheme is shown in FIG. 1 for expressing an EGFP-ACTB fusion protein. The targeting vector contains homology arms of ~1 kb flanking the EGFP sequence, and the sgRNA targets the ACTB allele at a position near the ACTB gene start codon ATG. After successful homologous recombination, the EGFP sequence would be inserted after the start codon of the ACTB genomic locus for expression of the EGFP-ACTB fusion protein. The sgRNA target sequence for the human ACTB gene was 5'-cgcggcgatatcat-catccatgg-3' (SEQ ID NO: 21).

The Cas9 sequence (SEQ ID NO: 22) is shown below. The bold underlined sequence is the 3×FLAG tag sequence. The italic underlined sequences are two SV40 nuclear localization sequences (NLS).

```
SEQ ID NO: 22:
5'-ATG GACTATAAGGACCACGACGGAGACTACAAGGATCATGATATTGA

TTACAAAGACGATGACGATAAG ATGCC CCAAAGAAGAAGCGGAAGGTC G

GTATCCACGGAGTCCCAGCAGCCGACAAGAAGTACAGCATCGGCCTGGAC

ATCGGCACCAACTCTGTGGGCTGGGCCGTGATCACCGACGAGTACAAGGT

GCCCAGCAAGAAATTCAAGGTGCTGGGCAACACCGACCGGCACAGCATCA

AGAAGAACCTGATCGGAGCCCTGCTGTTCGACAGCGGCGAAACAGCCGAG

GCCACCCGGCTGAAGAGAACCGCCAGAAGAAGATACACCAGACGGAAGAA

CCGGATCTGCTATCTGCAAGAGATCTTCAGCAACGAGATGGCCAAGGTGG

ACGACAGCTTCTTCCACAGACTGGAAGAGTCCTTCCTGGTGGAAGAGGAT

AAGAAGCACGAGCGGCACCCCATCTTCGGCAACATCGTGGACGAGGTGGC

CTACCACGAGAAGTACCCCACCATCTACCACCTGAGAAAGAAACTGGTGG

ACAGCACCGACAAGGCCGACCTGCGGCTGATCTATCTGGCCCTGGCCCAC

ATGATCAAGTTCCGGGGCCACTTCCTGATCGAGGGCGACCTGAACCCCGA

CAACAGCGACGTGGACAAGCTGTTCATCCAGCTGGTGCAGACCTACAACC
```

```
-continued
AGCTGTTCGAGGAAAACCCCATCAACGCCAGCGGCGTGGACGCCAAGGCC

ATCCTGTCTGCCAGACTGAGCAAGAGCAGACGGCTGGAAAATCTGATCGC

CCAGCTGCCCGGCGAGAAGAAGAATGGCCTGTTCGGAAACCTGATTGCCC

TGAGCCTGGGCCTGACCCCCAACTTCAAGAGCAACTTCGACCTGGCCGAG

GATGCCAAACTGCAGCTGAGCAAGGACACCTACGACGACGACCTGGACAA

CCTGCTGGCCCAGATCGGCGACCAGTACGCCGACCTGTTTCTGGCCGCCA

AGAACCTGTCCGACGCCATCCTGCTGAGCGACATCCTGAGAGTGAACACC

GAGATCACCAAGGCCCCCCTGAGCGCCTCTATGATCAAGAGATACGACGA

GCACCACCAGGACCTGACCCTGCTGAAAGCTCTCGTGCGGCAGCAGCTGC

CTGAGAAGTACAAAGAGATTTTCTTCGACCAGAGCAAGAACGGCTACGCC

GGCTACATTGACGGCGGAGCCAGCCAGGAAGAGTTCTACAAGTTCATCAA

GCCCATCCTGGAAAAGATGGACGGCACCGAGGAACTGCTCGTGAAGCTGA

ACAGAGAGGACCTGCTGCGGAAGCAGCGGACCTTCGACAACGGCAGCATC

CCCCACCAGATCCACCTGGGAGAGCTGCACGCCATTCTGCGGCGGCAGGA

AGATTTTTACCCATTCCTGAAGGACAACCGGGAAAAGATCGAGAAGATCC

TGACCTTCCGCATCCCCTACTACGTGGGCCCTCTGGCCAGGGGAAACAGC

AGATTCGCCTGGATGACCAGAAAGAGCGAGGAAACCATCACCCCCTGGAA

CTTCGAGGAAGTGGTGGACAAGGGCGCTTCCGCCCAGAGCTTCATCGAGC

GGATGACCAACTTCGATAAGAACCTGCCCAACGAGAAGGTGCTGCCCAAG

CACAGCCTGCTGTACGAGTACTTCACCGTGTATAACGAGCTGACCAAAGT

GAAATACGTGACCGAGGGAATGAGAAAGCCCGCCTTCCTGAGCGGCGAGC

AGAAAAAGGCCATCGTGGACCTGCTGTTCAAGACCAACCGGAAAGTGACC

GTGAAGCAGCTGAAAGAGGACTACTTCAAGAAAATCGAGTGCTTCGACTC

CGTGGAAATCTCCGGCGTGGAAGATCGGTTCAACGCCTCCCTGGGCACAT

ACCACGATCTGCTGAAAATTATCAAGGACAAGGACTTCCTGGACAATGAG

GAAAACGAGGACATTCTGGAAGATATCGTGCTGACCCTGACACTGTTTGA

GGACAGAGAGATGATCGAGGAACGGCTGAAAACCTATGCCCACCTGTTCG

ACGACAAAGTGATGAAGCAGCTGAAGCGGCGGAGATACACCGGCTGGGGC

AGGCTGAGCCGGAAGCTGATCAACGGCATCCGGGACAAGCAGTCCGGCAA

GACAATCCTGGATTTCCTGAAGTCCGACGGCTTCGCCAACAGAAACTTCA

TGCAGCTGATCCACGACGACAGCCTGACCTTTAAAGAGGACATCCAGAAA

GCCCAGGTGTCCGGCCAGGGCGATAGCCTGCACGAGCACATTGCCAATCT

GGCCGGCAGCCCCGCCATTAAGAAGGGCATCCTGCAGACAGTGAAGGTGG

TGGACGAGCTCGTGAAAGTGATGGGCCGGCACAAGCCCGAGAACATCGTG

ATCGAAATGGCCAGAGAGAACCAGACCACCCAGAAGGGACAGAAGAACAG

CCGCGAGAGAATGAAGCGGATCGAAGAGGGCATCAAAGAGCTGGGCAGCC

AGATCCTGAAAGAACACCCCGTGGAAAACACCCAGCTGCAGAACGAGAAG

CTGTACCTGTACTACCTGCAGAATGGGCGGGATATGTACGTGGACCAGGA

ACTGGACATCAACCGGCTGTCCGACTACGATGTGGACCATATCGTGCCTC

AGAGCTTTCTGAAGGACGACTCCATCGACAACAAGGTGCTGACCAGAAGC

GACAAGAACCGGGGCAAGAGCGACAACGTGCCCTCCGAAGAGGTCGTGAA
```

-continued

```
GAAGATGAAGAACTACTGGCGGCAGCTGCTGAACGCCAAGCTGATTACCC

AGAGAAAGTTCGACAATCTGACCAAGGCCGAGAGAGGCGGCCTGAGCGAA

CTGGATAAGGCCGGCTTCATCAAGAGACAGCTGGTGGAAACCCGGCAGAT

CACAAAGCACGTGGCACAGATCCTGGACTCCCGGATGAACACTAAGTACG

ACGAGAATGACAAGCTGATCCGGGAAGTGAAAGTGATCACCCTGAAGTCC

AAGCTGGTGTCCGATTTCCGGAAGGATTTCCAGTTTTACAAAGTGCGCGA

GATCAACAACTACCACCACGCCCACGACGCCTACCTGAACGCCGTCGTGG

GAACCGCCCTGATCAAAAAGTACCCTAAGCTGGAAAGCGAGTTCGTGTAC

GGCGACTACAAGGTGTACGACGTGCGGAAGATGATCGCCAAGAGCGAGCA

GGAAATCGGCAAGGCTACCGCCAAGTACTTCTTCTACAGCAACATCATGA

ACTTTTTCAAGACCGAGATTACCCTGGCCAACGGCGAGATCCGGAAGCGG

CCTCTGATCGAGACAAACGGCGAAACCGGGGAGATCGTGTGGGATAAGGG

CCGGGATTTTGCCACCGTGCGGAAAGTGCTGAGCATGCCCCAAGTGAATA

TCGTGAAAAAGACCGAGGTGCAGACAGGCGGCTTCAGCAAAGAGTCTATC

CTGCCCAAGAGGAACAGCGATAAGCTGATCGCCAGAAAGAAGGACTGGGA

CCCTAAGAAGTACGGCGGCTTCGACAGCCCCACCGTGGCCTATTCTGTGC

TGGTGGTGGCCAAAGTGGAAAAGGGCAAGTCCAAGAAACTGAAGAGTGTG

AAAGAGCTGCTGGGGATCACCATCATGGAAAGAAGCAGCTTCGAGAAGAA

TCCCATCGACTTTCTGGAAGCCAAGGGCTACAAAGAAGTGAAAAAGGACC

TGATCATCAAGCTGCCTAAGTACTCCCTGTTCGAGCTGGAAAACGGCCGG

AAGAGAATGCTGGCCTCTGCCGGCGAACTGCAGAAGGGAAACGAACTGGC

CCTGCCCTCCAAATATGTGAACTTCCTGTACCTGGCCAGCCACTATGAGA

AGCTGAAGGGCTCCCCCGAGGATAATGAGCAGAAACAGCTGTTTGTGGAA

CAGCACAAGCACTACCTGGACGAGATCATCGAGCAGATCAGCGAGTTCTC

CAAGAGAGTGATCCTGGCCGACGCTAATCTGGACAAAGTGCTGTCCGCCT

ACAACAAGCACCGGGATAAGCCCATCAGAGAGCAGGCCGAGAATATCATC

CACCTGTTTACCCTGACCAATCTGGGAGCCCCTGCCGCCTTCAAGTACTT

TGACACCACCATCGACCGGAAGAGGTACACCAGCACCAAAGAGGTGCTGG

ACGCCACCCTGATCCACCAGAGCATCACCGGCCTGTACGAGACACGGATC

GACCTGTCTCAGCTGGGAGGCGAC
```
<u>AAAAGGCCGGCGGCCACGAAAAAGGC</u>

<u>CGGCCAGGCAAAAAAGAAAAAG</u>taa-3'

The UL12 sequence (SEQ ID NO: 23) is shown below. The bold underlined sequence is the 3×FLAG tag sequence. The italic underlined sequence is a SV40 nuclear localization sequence (NLS).

SEQ ID NO: 23:
5'-ATG<u>*CCAAAGAAGAAGCGGAAGGTC*</u>GAGTCCACGGGAGGCCCAGCATG

```
TCCGCCGGGACGCACCGTGACTAAGCGTTCCTGGGCCCTGGCCGAGGACA

CCCCTCGTGGCCCCGACAGCCCCCCAAGCGCCCCCGCCCTAACAGTCTT

CCGCTGACAACCACCTTCCGTCCCCTGCCCCCCCCACCCCAGACGACGTC

AGCTGTGGACCCAAGCTCCCATTCGCCCGATAACCCCCCACGTGATCAGC
```

ACGCCACCGACACCGCAGACGAAAAGCCCCGGGCCGCGTCGCCGGCACTT

TCTGACGCCTCAGGGCCTCCGACCCCAGACATTCCGCTATCTCCTGGGGG

CACCCACGCCCGCGACCCGGACGCCGATCCCGACTCCCCGGACCTTGACT

CTATGTGGTCGGCGTCGGTGATCCCCAACGCGCTGCCCTCCCATATACTA

GCCGAGACGTTCGAGCGCCACCTGCGCGGGTTGCTGCGCGGCGTCCGCGC

CCCCCTGGCCATCGGTCCCCTCTGGGCCCGCCTGGATTATCTGTGTTCCC

TGGCCGTGGTCCTCGAGGAGGCGGGTATGGTGGACCGCGGACTCGGCCGG

CACCTATGGCGCCTGACGCGCCGCGGGCCCCCGCCGCCGCGGACGCCGT

GGCGCCCCGGCCCCTCATGGGGTTTTACGAGGCGGCCACGCAAAACCAGG

CCGACTGCCAGCTATGGGCCCTGCTCCGGCGGGGCCTCACGACCGCATCC

ACCCTCCGCTGGGGCCCCCAGGGTCCGTGTTTCTCGCCCCAGTGGCTGAA

GCACAACGCCAGCCTGCGGCCGGATGTACAGTCTTCGGCGGTGATGTTCG

GGCGGGTGAACGAGCCGACGGCCCGAAGCCTGCTGTTTCGCTACTGCGTG

GGCCGCGCGGACGACGGCGGCGAGGCCGGCGCCGACACGCGGCGCTTTAT

CTTCCACGAACCCGGCGACCTCGCCGAAGAGAACGTGCATACGTGTGGGG

TCCTCATGGACGGTCACACGGGGATGGTCGGGGCGTCCCTGGATATTCTC

GTCTGTCCTCGGGACACTCACGGCTACCTGGCCCCAGTCCCCAAGACCCC

CCTGGCCTTTTACGAGGTCAAATGCCGGGCCAAGTACGCTTTCGACCCCA

TGGACCCCAGCGACCCCACGGCCTCCGCGTACGAGGACTTGATGGCACAC

CGGTCCCCGGAGGCGTTCCGGGCATTTATCCGGTCGATCCCGAAGCCCAG

CGTGCGATACTTCGCGCCCGGGCGCGTCCCCGGCCCGGAGGAGGCTCTCG

TCACGCAAGACCAGGCCTGGTCAGAGGCCCACGCCTCGGGCGAAAAAGG

CGGTGCTCCGCCGCGGATCGGGCCTTGGTGGAGTTAAATAGCGGCGTTGT

CTCGGAGGTGCTTCTGTTTGGCGCCCCCGACCTCGGACGCCAAACCATCT

CCCCCGTGTCCTGGAGCTCCGGGGATCTGGTCCGCCGCGAGCCCGTCTTC

GCGAACCCCCGTCACCCGAACTTTAAGCAGATCTTGGTGCAGGGCTACGT

GCTCGACAGCCACTTCCCCGACTGCCCCCCCCACCCGCATCTGGTGACGT

TTATCGGCAGGCACCGCACCAGCGCGGAGGAGGGCGTAACGTTCCGCCTG

GAGGACGGCGCCGGGGCTCTCGGGGCCGCAGGACCCAGCAAGGCGTCCAT

TCTCCCGAACCAGGCCGTTCCGATCGCCCTGATCATTACCCCCGTCCGCA

TCGATCCGGAGATCTATAAGGCCATCCAGCGAAGCAGCCGCCTGGCGTTC

GACGACACGCTCGCCGAGCTATGGGCCTCTCGTTCTCCGGGGCCCGGCCC

TGCTGCTGCCGAAACAACGTCCTCATCACCGACGACGGGGAGGTCGTCTC

GC<u>GACTATAAGGACCACGACGGAGACTACAAGGATCATGATATTGATTAC</u>

<u>AAAGACGATGACGATAAG</u>TGA-3'

The following plasmids were constructed: Cas9/sgRNA-hACTB; Cas9/sgRNA-LS14; Targeting vector TV-LS14-hACTB; and pcDNA3.1 Hygro(+)—UL12.

The constructed plasmids were transfected into U2OS cells using a Neon (Invitrogen) transfection system by electroporation.

The ACTB gene encodes β-actin, which is a component of the cytoskeleton. Three days after transfection, green fluorescence indicating the filamentous structure of the cytoskeleton was observed by fluorescent microscopy (FIG. 2).

Figure 3:
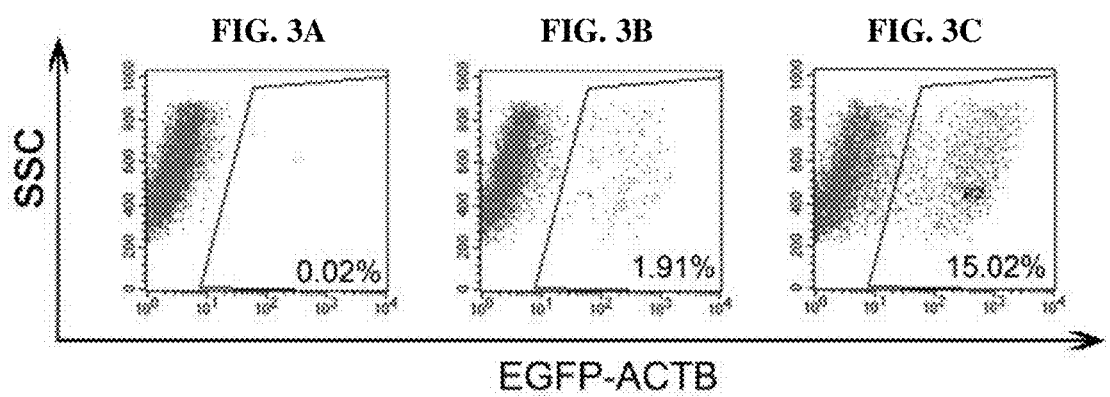

Flow cytometry analysis indicated that the efficiency of conventional CRISPR/Cas9-mediated knock-in of EGFP was only around 1.91%. In contrast, the EKI system achieved a knock-in efficiency of 15.02% (FIGS. 3A-3C).

Figure 4:
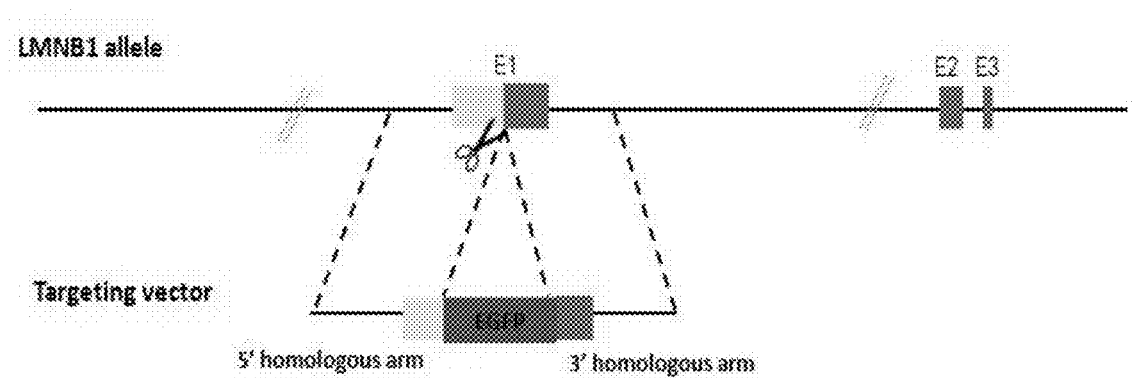
FIG. 4 depicts a targeting scheme for knocking in EGFP-LMNB1 in the C6 cell line.

Example 2. The EKI System Significantly Increases Knock-in Efficiency of EGFP-LMNB1 in C6 Cells A targeting scheme is shown in FIG. 4 for expressing an EGFP-LMNB1 fusion protein. The targeting vector contains homology arms of ~1 kb flanking the EGFP sequence, and the sgRNA targets the LMNB1 allele at a position near the LMNB1 gene start codon ATG. After successful homologous recombination, the EGFP sequence would be inserted after the start codon of the LMNB1 genomic locus for expression of the EGFP-LMNB1 fusion protein. The sgRNA target sequence for the human LMNB1 gene was 5'-gctgtctccgccgcccgccatgg-3' (SEQ ID NO: 24). The sgRNA target sequence for the rat LMNB1 gene was 5'-gggggtcgcggtcgccatggcgg-3' (SEQ ID NO: 25).

The following plasmids were constructed: Cas9/sgRNA-LMNB1; Cas9/sgRNA-LS14; Targeting vector TV-LS14-LMNB1; and pcDNA3.1 Hygro(+)—UL12.

The constructed plasmids were transfected into C6 cells using a Neon (Invitrogen) transfection system by electroporation.

The LMNB1 gene encodes lamin B1, which is a component of the nuclear lamina. Three days after transfection, green fluorescence indicating the nuclear membrane structure was observed by fluorescent microscopy (FIG. 5).

Flow cytometry analysis indicated that the efficiency of conventional CRISPR/Cas9-mediated knock-in of EGFP was only around 0.19%. In contrast, the EKI system achieved a knock-in efficiency of 3.6% (FIGS. 6A-6C).

In another experiment, TurboGFP was used instead of EGFP for expressing a TurboGFP-LMNB1 fusion protein in C6 cells, using the targeting scheme shown in FIG. 4 (data not shown).

Example 3. The EKI System Achieves Double Knock-in of EGFP-ACTB and mCherry-LMNB1 in U2OS Cells A targeting scheme is shown in FIGS. 7A-7B for expressing an EGFP-ACTB fusion protein and an mCherry-LMNB1 fusion protein after knock-in of the EGFP and mCherry sequences into the endogenous ACTB and LMNB1 gene loci, respectively. The targeting vectors contain homology arms of ~1 kb flanking the EGFP and mCherry sequences, respectively. In addition, the sgRNAs target the ACTB allele and the LMNB1 allele at positions near their start codons ATG. After successful homologous recombination, the EGFP sequence would be inserted after the start codon of the ACTB genomic locus for expression of the EGFP-ACTB fusion protein, and the mCherry sequence would be inserted after the start codon of the LMNB1 genomic locus for expression of the mCherry-LMNB1 fusion protein.

The following plasmids were constructed: Cas9/sgRNA-ACTB; Cas9/sgRNA-LMNB1; Cas9/sgRNA-LS14; Targeting vector TV-LS14-ACTB; Targeting vector TV-LS14-LMNB1; and pcDNA3.1 Hygro(+)—UL12.

Figure 8:
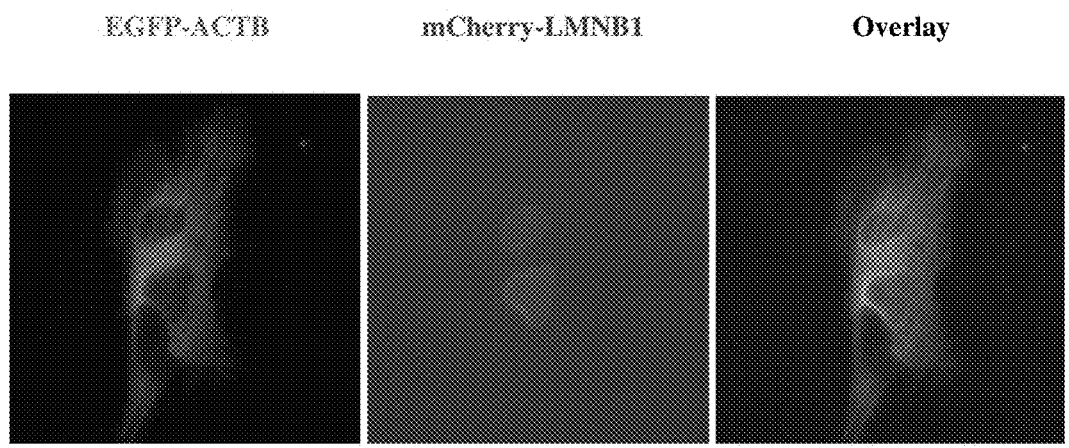
FIG. 8 shows fluorescent microscopic images indicating successful double knock-in and expression of the EGFP-ACTB and mCherry-LMNB1 fusion proteins in the same U2OS cell mediated by the EKI system.

The constructed plasmids were transfected into U2OS cells using a Neon (Invitrogen) transfection system by electroporation. Three days after transfection, green fluorescence indicating the filamentous structure of the cytoskeleton and red fluorescence indicating the nuclear membrane structure were observed by fluorescent microscopy (FIG. 8).

Figure 9:
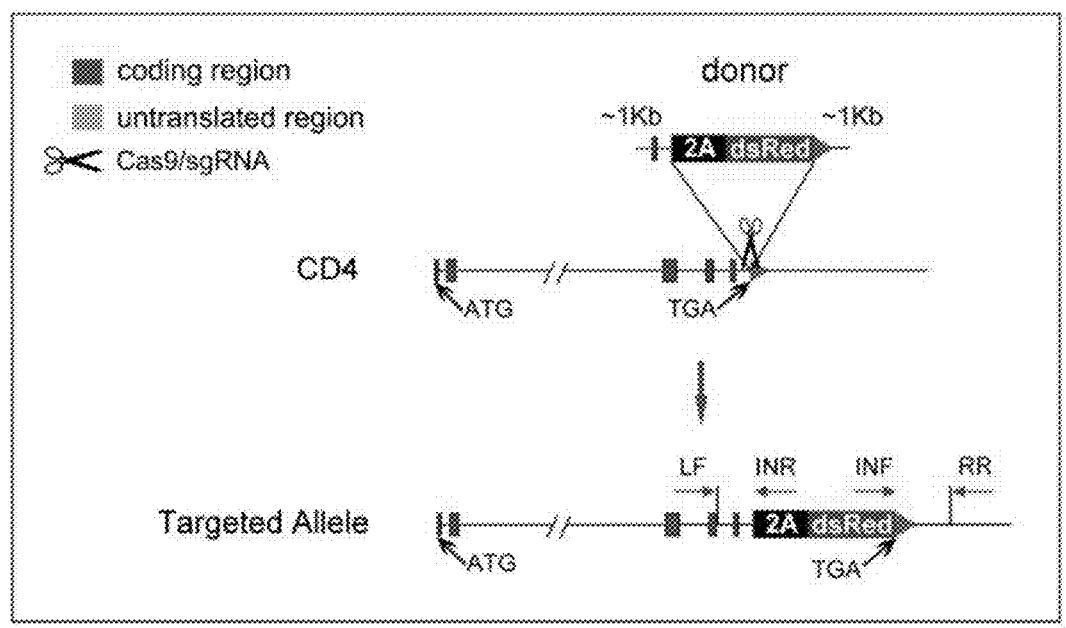
FIG. 9 depicts a targeting scheme for generating CD4-2A-dsRed knock-in rats.

Example 4. Using the EKI System to Efficiently Generate CD4-2A-dsRed Knock-in Rats A targeting scheme is shown in FIG. 9 for generating CD4-2A-dsRed knock-in rats. The targeting vector contains homology arms of ~1 kb flanking the 2A-dsRed sequence, and the sgRNA targets the endogenous rat CD4 allele at a position near the termination codon. After successful homologous recombination, the 2A-dsRed sequence inserted near the termination codon of the CD4 genomic locus would be expressed as the CD4-2A-dsRed fusion protein. CD4 positive cells of the knock-in rat would express the 2A-dsRed red fluorescent protein. The sgRNA target sequence for the rat CD4 gene was 5'-gaaaagccacaatctcatatgagg-3' (SEQ ID NO: 26). The sgRNA target sequence for LS14 was 5'-ggtattcactcctaaagcgtcgg-3' (SEQ ID NO: 27).

An exemplary targeting vector is shown in the 5' to 3' direction: CCGACGCTTTAGGAGTGAATACC (SEQ ID NO: 28, LS14 sequence)—Left Homology Arm-2A-dsRed-Right Homology Arm—CCGACGCTTTAGGAGTGAATACC (SEQ ID NO: 29, LS14 sequence).

A U6-sgRNA backbone sequence (SEQ ID NO: 30) can be used. The underlined sequence is the U6 promoter sequence, the bolded sequence is replaced by a target sequence when making a construct, and the italicized sequence is the structural sequence of the sgRNA.

SEQ ID NO: 30:
<u>GAGGGCCTATTTCCCATGATTCCTTCATATTTGCATATACGATACAAGGC</u>

<u>TGTTAGAGAGATAATTGGAATTAATTTGACTGTAAACACAAAGATATTAG</u>

<u>TACAAAATACGTGACGTAGAAAGTAATAATTTCTTGGGTAGTTTGCAGTT</u>

<u>TTAAAATTATGTTTTAAAATGGACTATCATATGCTTACCGTAACTTGAAA</u>

<u>GTATTTCGATTTCTTGGCTTTATATATCTTGTGGAAAGGACGAAACACC</u>N

NNNNNNNNNN*GTTTTAGAGCTAGAAATAGCAAGTTAAAATAAGGCTAGTCC*

*GTTATCAACTTGAAAAAGTGGCACCGAGTCGGTGCTTTTT*

The T7-sgRNA backbone sequence (SEQ ID NO: 31) is shown below. The underlined sequence is the T7 promoter sequence, the bolded sequence is replaced by a target sequence when making a construct, and the italicized sequence is the structural sequence of the sgRNA.

SEQ ID NO: 31:
<u>TAATACGACTCACTATAGG</u>NNNNNNNNNNN*GTTTTAGAGCTAGAAATAGCA*

*AGTTAAAATAAGGCTAGTCCGTTATCAACTTGAAAAAGTGGCACCGAGTC*

*GGTGCTTTT*

The following plasmids were constructed: Cas9/sgRNA-CD4; Cas9/sgRNA-LS14; Targeting vector TV-LS14-CD4; pcDNA3.1 Hygro(+)—UL12; T7-Cas9; T7-sgRNA-CD4; and T7-sgRNA-LS14.

The constructed plasmids were transcribed in vitro to obtain UL12 mRNA, Cas9 mRNA, and sgRNAs for CD4 and LS14. UL12 mRNA, Cas9 mRNA, sgRNA-CD4, sgRNA-LS14, and TV-LS14-CD4 were then injected into fertilized eggs of rats. The injected fertilized eggs were then transplanted into pseudopregnant rats.

Figure 10:
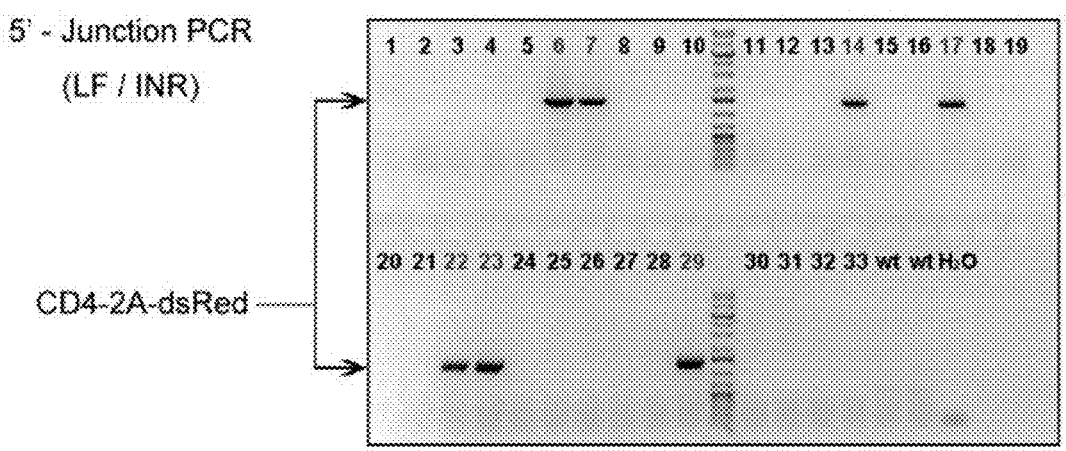
FIG. 10 depicts genotyping results of CD4-2A-dsRed knock-in rats of the F0 generation, using 5'-junction PCR reaction.

33 rats of the F0 generation were born and genotyped. Primers LF and INR were used in the 5'-junction PCR reaction (FIG. 9). The forward primer LF is localized distal to the left homology arm, and the reverse primer INR is localized within the 2A-dsRed region. 7 of the 33 F0 rats were tested positive for the knock-in (FIG. 10).

Figure 11:
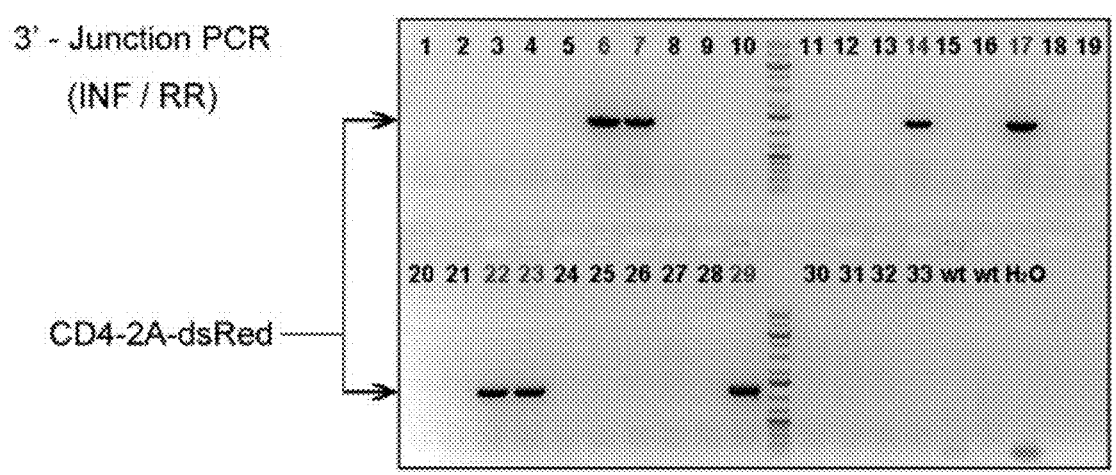
FIG. 11 depicts genotyping results of CD4-2A-dsRed knock-in rats of the F0 generation, using 3'-junction PCR reaction.

Primers INF and RR were used in the 3'-junction PCR reaction (FIG. 9). The forward primer INF is localized within the 2A-dsRed region, and the reverse primer RR is localized distal to the right homology arm. 7 of the 33 F0 rats were tested positive for the knock-in (FIG. 11).

Thus, the 5'-junction PCR reaction and the 3'-junction PCR reaction yielded the same results, and F0 rats numbered #6, #7, #14, #17, #22, #23, and #29 were tested positive for the knock-in by both PCR assays. The positive rate is 7/33 (21.2%).

Figure 12A:
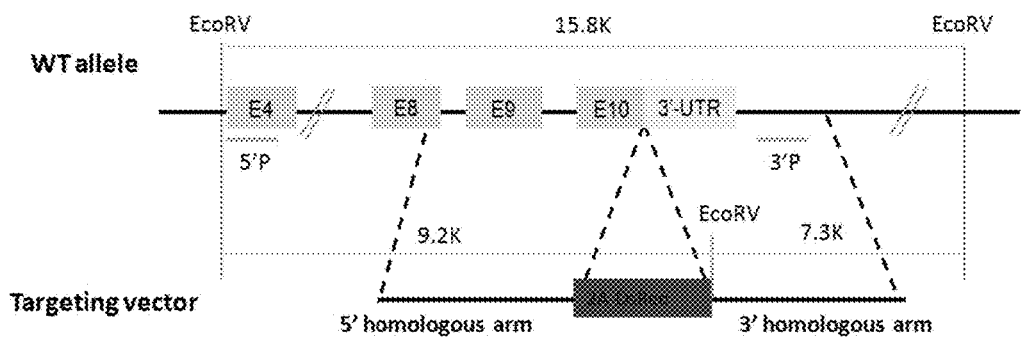
FIGS. 12A AND 12B depict southern blot results for the CD4-2A-dsRed knock-in rats.
Figure 12B:
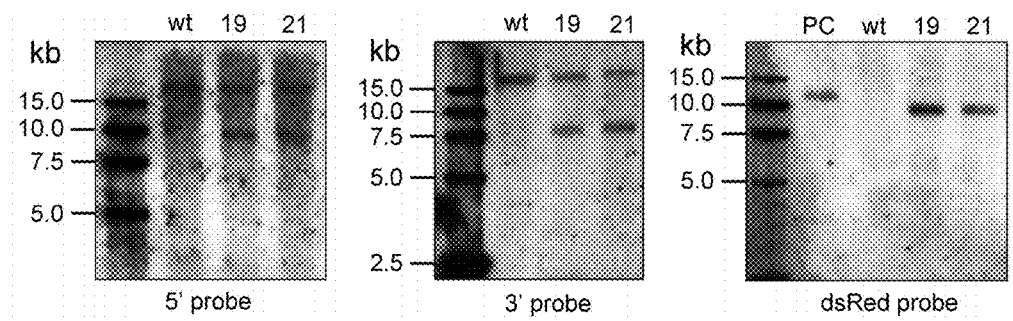

FIGS. 12A-12B show southern blot results for the knock-in rat, further indicating insertion of the donor sequence at the predetermined sites. The two F1 rats (#19 and #21) tested with southern blots were the offspring of the #22 F0 rat in FIG. 10 and FIG. 11.

Example 5. Using the EKI System to Generate Knock-in of TH-GFP in H9 Cells

This example illustrates the generation of a TH-GFP knock-in in H9 human embryonic stem cells using the EKI system.

The human TH gene encodes tyrosine hydroxylase (also known as tyrosine 3-monooxygenase or tyrosinase), an enzyme that catalyzes the amino acid L-tyrosine to L-3,4-dihydroxyphenylalanine (L-DOPA) conversion. L-DOPA is a precursor for Dopamine. TH is expressed in the central nervous system, peripheral sympathetic neurons and the adrenal medulla, and is used as a dopaminergic neuron marker.

Figure 13:
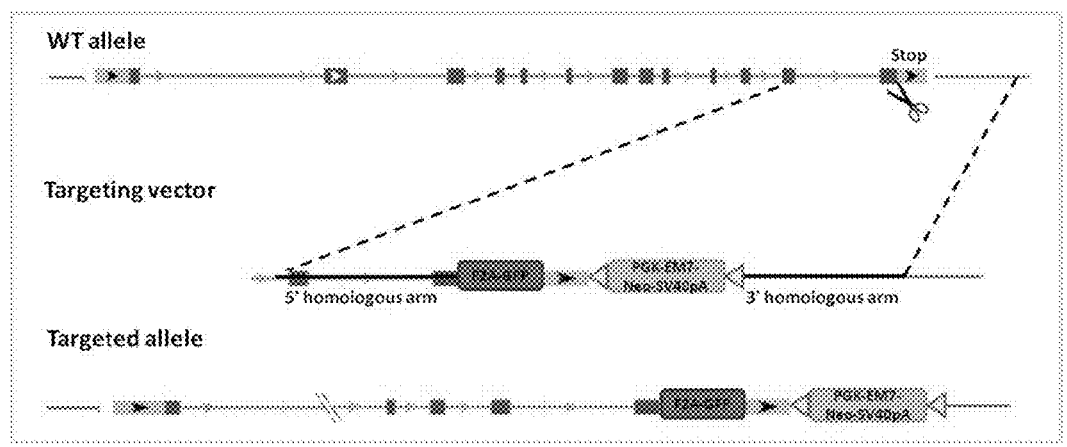
FIG. 13 depicts a targeting scheme for knocking in TH-GFP in the H9 cell line.

A targeting scheme is shown in FIG. 13 for generating a TH-GFP knock-in H9 cell line. The targeting vector contains homology arms of ~1 kb upstream of the F2A-GFP cassette and downstream of the PGK-EM7-Neo-SV40 polyA cassette. The sgRNA targets the TH allele at a position near its stop codon. After successful homologous recombination, the F2A-GFP cassette and the PGK-EM7-Neo-SV40 polyA cassette would be placed immediately before the stop codon and after the 3'UTR of the TH gene, respectively, for the expression of a TH-GFP fusion protein. The sgRNA target sequence for the human TH gene was 5'-ggacgccgtgcac-ctagccaa tgg-3' (SEQ ID NO: 44).

The following plasmids were constructed: Cas9/sgRNA-TH; Cas9/sgRNA-LS14; Targeting vector TV-LS14-TH; and pcDNA3.1 Neo(+)—UL12.

The constructed plasmids were transfected into H9 cells using a Neon (Invitrogen) transfection system by electroporation. $2\times10^6$ H9 cells, and 2.5 µg each of Cas9/sgRNA-TH, Cas9/sgRNA-LS14, TV-LS14-TH, and pcDNA3.1 Neo (+)—UL12 were used. Drug-resistant colonies were picked and expanded after 7-10 days of G418 selection.

Figure 14:
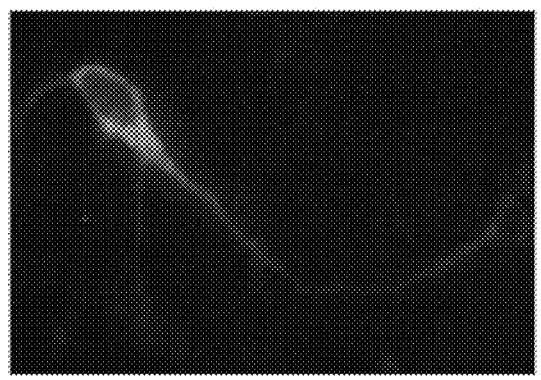
FIG. 14 shows a fluorescent microscopic image indicating the expression of the TH-GFP fusion protein in H9 cells after knocking in using the EKI system.

The green fluorescence from GFP can serve as a marker of the TH gene activity, which was found to express when H9 cells differentiated into dopaminergic neurons (see FIG. 14). This H9-TH-GFP cell line can be used to support research in many areas including dopaminergic neuron differentiation from human embryonic stem cells.

The knock-in of TH-GFP in H9 cells was genotyped in three independent cell lines using primers listed in Table 1, reaction components listed in Table 2, and the PCR cycling condition listed in Table 3.

TABLE 1

Primers used for H9-TH-GFP genotyping

| PCR Product | Primer | Sequence (5'-3') | Tm (° C.) | Product size (bp) |
|---|---|---|---|---|
| 5'PCR | hTH-5'-F | AGTGGAGTCAGTGATGCCATTGGCCTC (SEQ ID NO: 32) | 65 | 1362 |
|  | hTH-5'-R | GCCTTTGGTGCTCTTCATCTTGTTGG (SEQ ID NO: 33) | 61 |  |
| 3'PCR | hTH-3'-F | TACCCGTGATATTGCTGAAGAGCTTG (SEQ ID NO: 34) | 60 | 1751 |
|  | hTH-3'-R | TTTGGTAGTGGGCACCAGCTATCTG (SEQ ID NO: 35) | 61 |  |

TABLE 2

| PCR reaction components | |
|---|---|
| $H_2O$ | 17.75 µl |
| KOD buffer (10x) | 3 µl |
| dNTP (2 mM) | 3 µl |
| DMSO (0.5%) | 1.5 µl |
| $MgSO_4$ (25 mM) | 1.5 µl |
| Forward Primer (10 µM) | 0.75 µl |
| Reverse Primeer (10 µM) | 0.75 µl |
| Genomic DNA (100~200 ng/µl) | 1 µl |
| KOD-plus | 0.75 µl |
| Total | 30 µl |

TABLE 3

| PCR cycling condition | | |
|---|---|---|
| 94° C. | 5 min | |
| 94° C. | 30 sec | |
| 67° C. (−0.7° C./cycle) | 30 sec | 15 cycles |
| 68° C. | 1 min/kb | |
| 94° C. | 30 sec | |
| 57° C. | 30 sec | 25 cycles |
| 68° C. | 1 min/kb | |
| 68° C. | 10 min | |
| 4° C. | Hold | |

Figure 15:
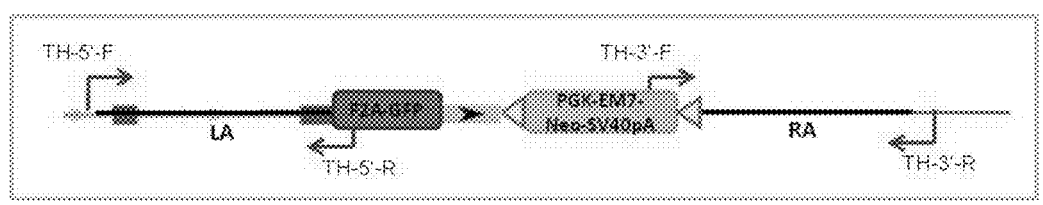
FIG. 15 shows the locations of the genotyping primers for TH-GFP knock-in in H9 cells. LA: left homology arm. RA: right homology arm.

Primers TH-5'-F and TH-5'-R were used in the 5'-junction PCR reaction (FIG. 15). The forward primer TH-5'-F is localized distal to the left homology arm, and the reverse primer TH-5'-R is localized at the F2A-GFP cassette. All three cell lines were tested positive for the knock-in (FIG. 16A).

Primers TH-3'-F and TH-3'-R were used in the 3'-junction PCR reaction (FIG. 15). The forward primer TH-3'-F is localized at the PGK-EM7-Neo-SV40 polyA cassette, and the reverse primer TH-3'-R is localized distal to the right homology arm. All three cell lines were tested positive for the knock-in (FIG. 16B).

Thus, 5'-junction PCR and 3'-junction PCR yielded the same results, and cell lines numbered #1, #2 and #3 were all tested positive for the knock-in by both PCR assays.

including reprogramming and human embryonic stem cell self-renewal and differentiation.

The knock-in of OCT4-EGFP in H9 cells was genotyped in 15 independent cell lines using primers listed in Table 4, reaction components listed in Table 2, and the PCR cycling condition listed in Table 3.

TABLE 4

Primers used for H9-OCT4-EGFP genotyping

| PCR Product | Primer | Sequence (5'-3') | Product size (bp) |
|---|---|---|---|
| 5' PCR | OCT4-5'-F | GGTATTCAGCCAAACGACCATCTGCCG (SEQ ID NO: 36) | 1344 |
|  | OCT4-5'-R | AGTCGTGCTGCTTCATGTGGTCG (SEQ ID NO: 37) |  |
| 3' PCR | OCT4-3'-F | TGACACGTGCTACGAGATTTCGATTC (SEQ ID NO: 38) | 1354 |
|  | OCT4-3'-R | ACAGGCTTCACCTGTACTGTCAGGGCA (SEQ ID NO: 39) |  |
| Full Length | OCT4-5'-F | GGTATTCAGCCAAACGACCATCTGCCG (SEQ ID NO: 36) | 3831 |
|  | OCT4-3'-R | ACAGGCTTCACCTGTACTGTCAGGGCA (SEQ ID NO: 39) |  |

Figure 17:
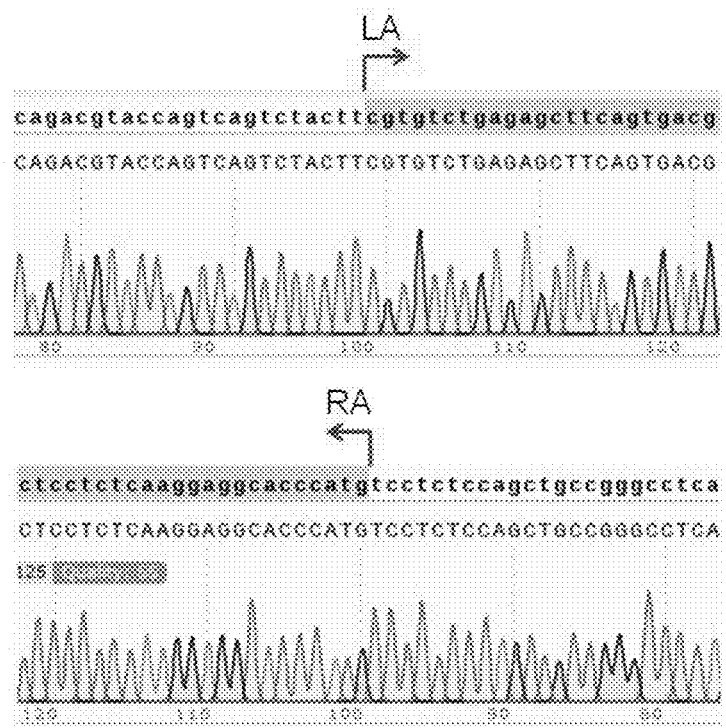
FIG. 17 shows the sequencing results of the PCR products from H9-TH-GFP cell line #1 in FIGS. 16A-16B. Shown in the chromatogram are sequences of CAGACGTACCA-GTCAGTCTACTTCGTGTCTGAGAGCTTCAGTGACG (SEQ ID NO: 40) and CTCCTCTCAAGGAGGCACCCAT-GTCCTCTCCAGCTGCCGGGCCTCA (SEQ ID NO: 41).

FIG. 17 shows the sequencing results of the PCR products from cell line #1, which confirmed that the cell line was correctly targeted at the TH locus.

Figure 18:
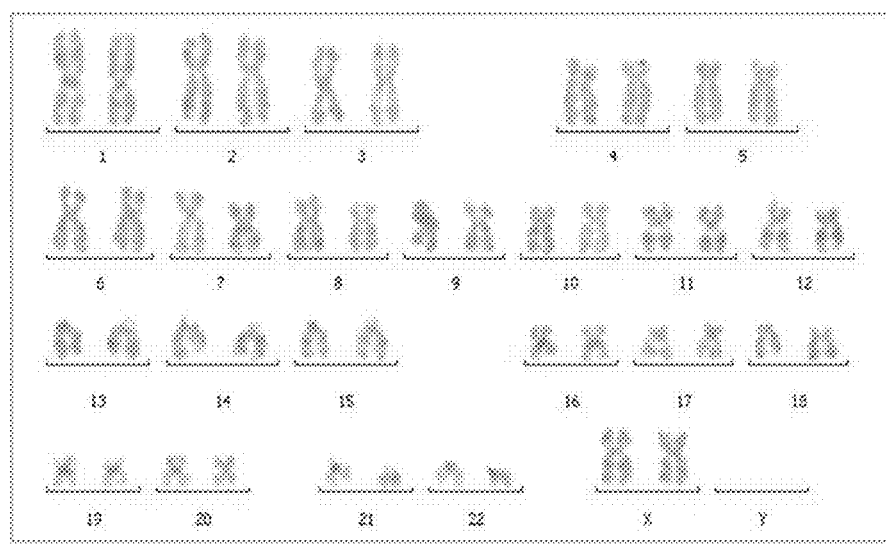
FIG. 18 shows the karyotype of H9-TH-GFP cell line #1 from FIGS. 16A-16B.

FIG. 18 shows that the tested cell line #1 has normal human karyotype.

Example 6. Using the EKI System to Generate Knock-in of OCT4-EGFP in H9 Cells This example illustrates the generation of an OCT4-EGFP knock-in in H9 human embryonic stem cells using the EKI system.

OCT4 (octamer-binding transcription factor 4; also known as POU5F1: POU domain, class 5, transcription factor 1), encoded by the POU5F1 gene in human, is a transcription factor that binds to the octamer motif (5'-ATTTGCAT-3'). It plays a critical role in embryonic development and stem cell self-renewal and pluripotency. OCT4 is expressed in human embryonic stem cells, germ cells, and adult stem cells. Aberrant expression of this gene in adult cells is associated with tumorigenesis.

Figure 19:
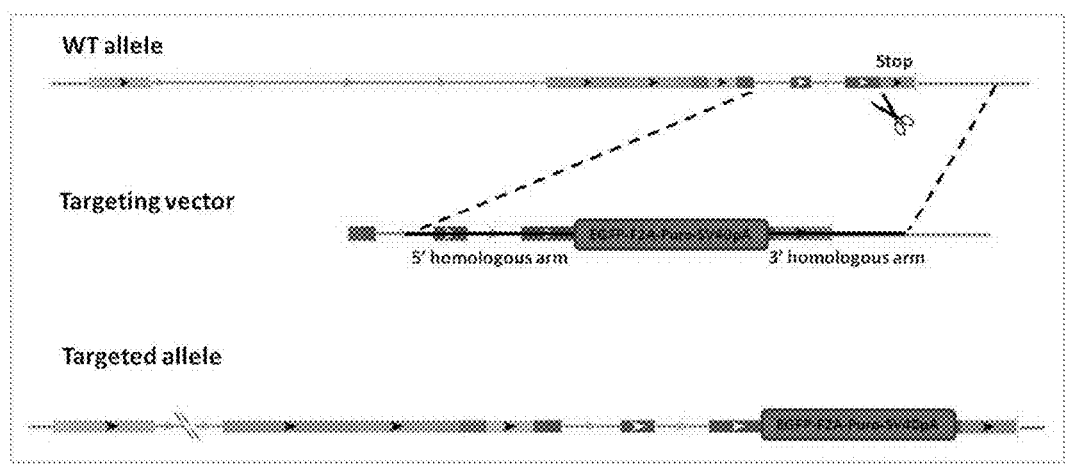
FIG. 19 depicts a targeting scheme for knocking in OCT4-EGFP in the H9 cell line.

A targeting scheme is shown in FIG. 19 for generating an OCT4-EGFP knock-in H9 cell line. The targeting vector contains homology arms of ~1 kb flanking the EGFP-F2A-Puro-SV40-polyA signal sequence cassette. The sgRNA targets the OCT4 allele at a position near its stop codon. After successful homologous recombination, the EGFP-F2A-Puro-SV40-polyA signal sequence cassette would be placed immediately before the stop codon of the OCT4 gene, for the expression of an OCT4-EGFP fusion protein. The sgRNA target sequence for the human OCT4 gene was 5'-tctcccatgcattcaaactgagg-3' (SEQ ID NO: 45).

The following plasmids were constructed: Cas9/sgRNA-OCT4; Cas9/sgRNA-LS14; Targeting vector TV-LS14-OCT4; and pcDNA3.1 Puro(+)—UL12.

The constructed plasmids were transfected into H9 cells using a Neon (Invitrogen) transfection system by electroporation. 2×10$^6$ H9 cells, and 2.5 μg each of Cas9/sgRNA-OCT4, Cas9/sgRNA-LS14, TV-LS14-OCT4, and pcDNA3.1 Puro(+)—UL12 were used. Drug-resistant colonies were picked and expanded after 7-10 days of Puromycin selection.

Figure 20:
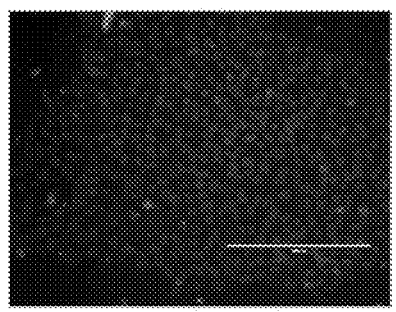
FIG. 20 shows a fluorescent microscopic image indicating the expression of the OCT4-EGFP fusion protein in H9 cells after knocking in using the EKI system.
Figure 21:
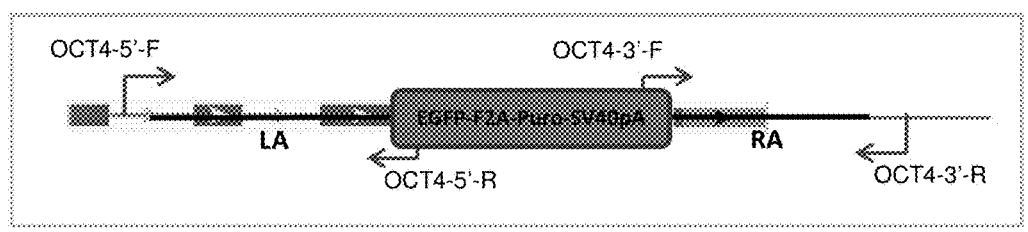
FIG. 21 shows the locations of the genotyping primers for OCT4-EGFP knock-in in H9 cells. LA: left homology arm. RA: right homology arm.

The green fluorescence from EGFP can serve as a marker of the OCT4 gene activity, which was found to express in pluripotent stem cells (see FIG. 20). This H9-OCT4-EGFP cell line can be used to support research in many areas Primers OCT4-5'-F and OCT4-5'-R were used in the 5'-junction PCR reaction (FIG. 21). The forward primer OCT4-5'-F is localized distal to the left homology arm, and the reverse primer OCT4-5'-R is localized at the EGFP-F2A-Puro-SV40-polyA signal sequence cassette. All 15 cell lines were tested positive for the knock-in (FIG. 22A).

Primers OCT4-3'-F and OCT4-3'-R were used in the 3'-junction PCR reaction (FIG. 21). The forward primer OCT4-3'-F is localized at the EGFP-F2A-Puro-SV40-polyA signal sequence cassette, and the reverse primer OCT4-3'-R is localized distal to the right homology arm. Cell lines numbered #1, #2, #4, #6, #7, #10, #11 and #12 were tested positive for the knock-in (FIG. 22B).

Full length PCR reaction was further tested with primers OCT4-5'-F and OCT4-3'-R (FIG. 21). Cell lines numbered #1, #3, #4, #5, #6, #7, #10, #11 and #13 were tested positive for the knock-in (FIG. 22C).

Figure 23:
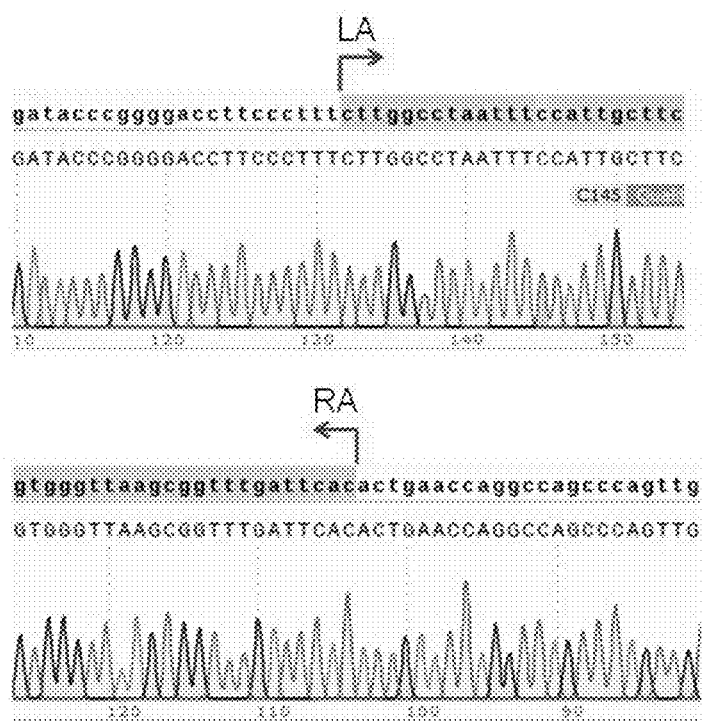
FIG. 23 shows the sequencing results of the PCR products from H9-OCT4-EGFP cell line #6 in FIGS. 22A-22C. Shown in the chromatogram are sequences of GATAC-CCGGGGACCTTCCCTTTCTTGGCCTAATTTCCATT-GCTTC (SEQ ID NO: 42) and GTGGGTTAAGCGGTTT-GATTCACACTGAACCAGGCCAGCCCAGTTG (SEQ ID NO: 43).

FIG. 23 shows the sequencing results of the PCR products from cell line #6, which confirmed that the cell line was correctly targeted at the OCT4 locus.

Figure 24:
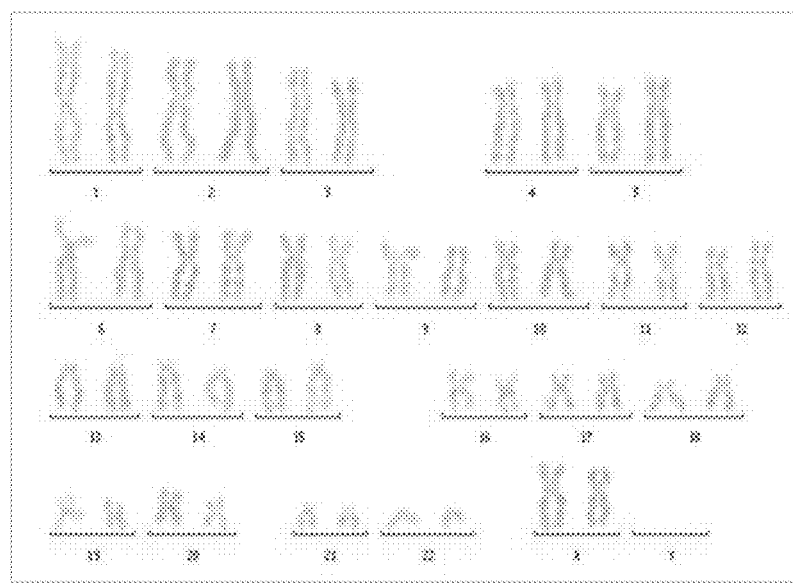
FIG. 24 shows the karyotype of H9-OCT4-EGFP cell line #6 in FIGS. 22A-22C.

FIG. 24 shows that the tested cell line #6 has normal human karyotype.

REFERENCES

Iacovitti L, Wei X, Cai J, Kostuk E W, Lin R, Gorodinsky A, Roman P, Kusek G, Das S S, Dufour A, Martinez T N, Dave K D. 2014. The hTH-GFP reporter rat model for the study of Parkinson's disease. PLoS One 9(12):e113151. [PubMed: 25462571]

Hockemeyer D, Wang H, Kiani S, Lai C S, Gao Q, Cassady J P, Cost G J, Zhang L, Santiago Y, Miller J C, Zeitler B, Cherone J M, Meng X, Hinkley S J, Rebar E J, Gregory P D, Urnov F D, Jaenisch R. 2011. Genetic engineering of human pluripotent cells using TALE nucleases. Nat. Biotechnol 29(8):731-4. [PubMed: 21738127]

Yu J, Vodyanik M A, Smuga-Otto K, Antosiewicz-Bourget J, Frane J L, Tian S, Nie J, Jonsdottir G A, Ruotti V, Stewart R, Slukvin I I, Thomson J A. 2007. Induced pluripotent stem cell lines derived from human somatic cells. Science 318(5858):1917-20. [PubMed: 18029452]

Boyer L A, Lee T I, Cole M F, Johnstone S E, Levine S S, Zucker J P, Guenther M G, Kumar R M, Murray H L, Jenner R G, Gifford D K, Melton D A, Jaenisch R, Young R A. 2005. Core transcriptional regulatory circuitry in human embryonic stem cells. Cell 122(6):947-56. [PubMed: 16153702]

What is claimed is:

1. A method of inserting a donor sequence at a predetermined insertion site on a chromosome in a eukaryotic cell, comprising:
   a) introducing into the cell a sequence-specific RNA-guided nuclease that cleaves the chromosome at the insertion site;
   b) introducing into the cell a donor construct; and
   c) introducing into the cell an exonuclease UL12;
   wherein the donor construct is a linear nucleic acid or cleaved within the cell to produce a linear nucleic acid,
   wherein the linear nucleic acid comprises a 5' homology arm, the donor sequence, and a 3' homology arm, wherein the 5' homology arm is homologous to a sequence upstream of the nuclease cleavage site on the chromosome and wherein the 3' homology arm is homologous to a sequence downstream of the nuclease cleavage site on the chromosome;
   wherein the 5' homology arm and the 3' homology arm are proximal to the 5' and 3' ends of the linear nucleic acid, respectively, and
   wherein the donor sequence is inserted into the chromosome at the insertion site through homologous recombination.

2. The method of claim 1, wherein the RNA-guided nuclease is Cas.

3. The method of claim 2, wherein the RNA-guided nuclease is Cas9.

4. The method of claim 1, further comprising introducing into the cell a guide RNA (gRNA) recognizing the insertion site.

5. The method of claim 1, wherein the RNA-guided nuclease is introduced into the cell as a protein, mRNA, or cDNA.

6. The method of claim 1, wherein the sequence homology between the 5' homology arm and the sequence 5' to the insertion site is at least 80%.

7. The method of claim 1, wherein the sequence homology between the 3' homology arm and the sequence 3' to the insertion site is at least 80%.

8. The method of claim 1, wherein the 5' homology arm and the 3' homology arm are at least 50 bp.

9. The method of claim 1, wherein the donor construct is a linear nucleic acid.

10. The method of claim 1, wherein the donor construct is circular when introduced into the cell and is cleaved within the cell to produce a linear nucleic acid.

11. The method of claim 10, wherein the donor construct further comprises a 5' flanking sequence upstream of the 5' homology arm and a 3' flanking sequence downstream of the 3' homology arm.

12. The method of claim 11, wherein the 5' flanking sequence or the 3' flanking sequence is about 1 to about 500 bp.

13. The method of claim 11, wherein the method further comprises introducing into the cell a second sequence-specific nuclease that cleaves the donor construct at one or both of the flanking sequences, thereby producing the linear nucleic acid.

14. The method of claim 11, wherein the sequence-specific nuclease is an RNA-guided nuclease, and wherein the method further comprises introducing into the cell a second guide RNA recognizing one or both of the flanking sequences.

15. The method of claim 1, wherein the eukaryotic cell is a mammalian cell.

16. The method of claim 15, wherein the mammalian cell is a zygote or a pluripotent stem cell.

17. The method of claim 15, wherein the mammalian cell is a tumor cell or an immortal cell.

18. A method of generating a genetically modified non-human animal comprising a donor sequence inserted at a predetermined insertion site on the chromosome of the animal, comprising:
   a) generating a cell with the donor sequence inserted at the predetermined insertion site on the chromosome according to the method of claim 1; and
   b) introducing the cell into a carrier animal to produce the genetically modified non-human animal.

19. The method of claim 18, wherein the genetically modified animal is a rodent.

20. The method of claim 18, wherein the cell is a zygote or a pluripotent stem cell.

* * * * *